(12) United States Patent
Crawford et al.

(10) Patent No.: US 12,318,153 B2
(45) Date of Patent: *Jun. 3, 2025

(54) SURGICAL ROBOT PLATFORM

(71) Applicant: GLOBUS MEDICAL, INC., Audubon, PA (US)

(72) Inventors: Neil R. Crawford, Chandler, AZ (US); Nicholas Theodore, Paradise Valley, AZ (US); Mitchell A. Foster, Scottsdale, AZ (US)

(73) Assignee: Globus Medical, Inc., Audubon, PA (US)

( * ) Notice: Subject to any disclaimer, the term of this patent is extended or adjusted under 35 U.S.C. 154(b) by 1267 days.

This patent is subject to a terminal disclaimer.

(21) Appl. No.: 17/071,307

(22) Filed: Oct. 15, 2020

(65) Prior Publication Data
US 2021/0022814 A1 Jan. 28, 2021

Related U.S. Application Data

(63) Continuation of application No. 15/648,621, filed on Jul. 13, 2017, now Pat. No. 10,835,326, which is a
(Continued)

(51) Int. Cl.
*A61B 34/30* (2016.01)
*A61B 5/06* (2006.01)
(Continued)

(52) U.S. Cl.
CPC .............. *A61B 34/30* (2016.02); *A61B 5/061* (2013.01); *A61B 5/062* (2013.01); *A61B 5/066* (2013.01);
(Continued)

(58) Field of Classification Search
CPC ......... A61B 34/30; A61B 5/066; A61B 10/02; A61B 10/0233; A61B 10/0275;
(Continued)

(56) References Cited

U.S. PATENT DOCUMENTS 10,835,326 B2 * 11/2020 Crawford ............... A61B 90/98
2004/0024311 A1 2/2004 Quaid
(Continued)

FOREIGN PATENT DOCUMENTS

JP 2008538184 A 10/2008

*Primary Examiner* — Katherine L Fernandez

(57) ABSTRACT

A medical robot system, including a robot coupled to an effectuator element with the robot configured for controlled movement and positioning. The system may include a transmitter configured to emit one or more signals, and the transmitter is coupled to an instrument coupled to the effectuator element. The system may further include a motor assembly coupled to the robot and a plurality of receivers configured to receive the one or more signals emitted by the transmitter. A control unit is coupled to the motor assembly and the plurality of receivers, and the control unit is configured to supply one or more instruction signals to the motor assembly. The instruction signals can be configured to cause the motor assembly to selectively move the effectuator element.

7 Claims, 42 Drawing Sheets

Related U.S. Application Data continuation of application No. 15/609,322, filed on May 31, 2017, which is a continuation of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | | |
|---|---|---|
| *A61B 10/02* | (2006.01) | |
| *A61B 17/02* | (2006.01) | |
| *A61B 17/16* | (2006.01) | |
| *A61B 17/17* | (2006.01) | |
| *A61B 17/70* | (2006.01) | |
| *A61B 17/88* | (2006.01) | |
| *A61B 34/00* | (2016.01) | |
| *A61B 34/10* | (2016.01) | |
| *A61B 34/20* | (2016.01) | |
| *A61B 34/32* | (2016.01) | |
| *A61B 46/20* | (2016.01) | |
| *A61B 50/13* | (2016.01) | |
| *A61B 90/00* | (2016.01) | |
| *A61B 90/14* | (2016.01) | |
| *A61B 90/96* | (2016.01) | |
| *A61B 90/98* | (2016.01) | |
| *A61M 5/172* | (2006.01) | |
| *A61N 1/05* | (2006.01) | |
| *B25J 9/10* | (2006.01) | |
| *A61B 17/00* | (2006.01) | |
| *A61B 90/11* | (2016.01) | |

(52) U.S. Cl.
CPC .......... *A61B 10/02* (2013.01); *A61B 10/0233* (2013.01); *A61B 10/0275* (2013.01); *A61B 17/025* (2013.01); *A61B 17/1615* (2013.01); *A61B 17/1671* (2013.01); *A61B 17/1703* (2013.01); *A61B 17/1757* (2013.01); *A61B 17/7082* (2013.01); *A61B 17/8866* (2013.01); *A61B 34/10* (2016.02); *A61B 34/20* (2016.02); *A61B 34/25* (2016.02); *A61B 34/32* (2016.02); *A61B 34/70* (2016.02); *A61B 34/74* (2016.02); *A61B 34/76* (2016.02); *A61B 46/20* (2016.02); *A61B 50/13* (2016.02); *A61B 90/14* (2016.02); *A61B 90/37* (2016.02); *A61B 90/39* (2016.02); *A61B 90/96* (2016.02); *A61B 90/98* (2016.02); *A61M 5/172* (2013.01); *A61N 1/0529* (2013.01); *B25J 9/1065* (2013.01); *A61B 5/064* (2013.01); *A61B 2010/0208* (2013.01); *A61B 2017/00119* (2013.01); *A61B 2017/00203* (2013.01); *A61B 2017/00207* (2013.01); *A61B 2017/00876* (2013.01); *A61B 2017/0256* (2013.01); *A61B 17/17* (2013.01); *A61B 2034/107* (2016.02); *A61B 2034/2051* (2016.02); *A61B 2034/2055* (2016.02); *A61B 2034/2059* (2016.02); *A61B 2034/2072* (2016.02); *A61B 2034/301* (2016.02); *A61B 2034/741* (2016.02); *A61B 2034/742* (2016.02); *A61B 2034/743* (2016.02); *A61B 2034/744* (2016.02); *A61B 2090/034* (2016.02); *A61B 2090/064* (2016.02); *A61B 2090/0811* (2016.02); *A61B 90/11* (2016.02); *A61B 2090/365* (2016.02); *A61B 2090/374* (2016.02); *A61B 2090/3762* (2016.02); *A61B 2090/3764* (2016.02); *A61B 2090/378* (2016.02); *A61B 2090/3937* (2016.02); *A61B 2090/3941* (2016.02); *A61B 2090/3945* (2016.02); *A61B 2090/395* (2016.02); *A61B 2090/3966* (2016.02); *A61B 2090/3975* (2016.02); *A61B 2090/3979* (2016.02); *A61B 2090/3983* (2016.02)

(58) Field of Classification Search
CPC .............. A61B 17/025; A61B 17/1615; A61B 17/1671; A61B 17/1703; A61B 17/1757; A61B 17/7082; A61B 17/8866; A61B 34/10; A61B 34/20; A61B 34/25; A61B 34/32; A61B 34/70; A61B 34/74; A61B 34/76; A61B 46/20; A61B 50/13; A61B 90/14; A61B 90/37; A61B 90/39; A61B 90/11; A61B 2010/0208; A61B 2017/00119; A61B 2017/00203; A61B 2017/00207; A61B 2017/0256; A61B 2034/107; A61B 2034/2051; A61B 2034/2055; A61B 2034/2059; A61B 2034/2072; A61B 2034/301; A61B 2034/741; A61B 2034/742; A61B 2034/743; A61B 2034/744; A61B 2090/034; A61B 2090/064; A61B 2090/365; A61B 2090/374; A61B 2090/3762; A61B 2090/3764; A61B 2090/378; A61B 2090/3937; A61B 2090/3941; A61B 2090/3945; A61B 2090/395; A61B 2090/3966; A61B 2090/3975; A61B 2090/3979; A61M 5/172; A61N 1/0529

See application file for complete search history.

(56) References Cited

U.S. PATENT DOCUMENTS

| | | | |
|---|---|---|---|
| 2006/0142657 A1* | 6/2006 | Quaid | A61B 90/37 600/424 |
| 2012/0226145 A1* | 9/2012 | Chang | A61B 34/30 600/424 |
| 2015/0127154 A1* | 5/2015 | Passot | G06N 3/008 901/3 |

* cited by examiner

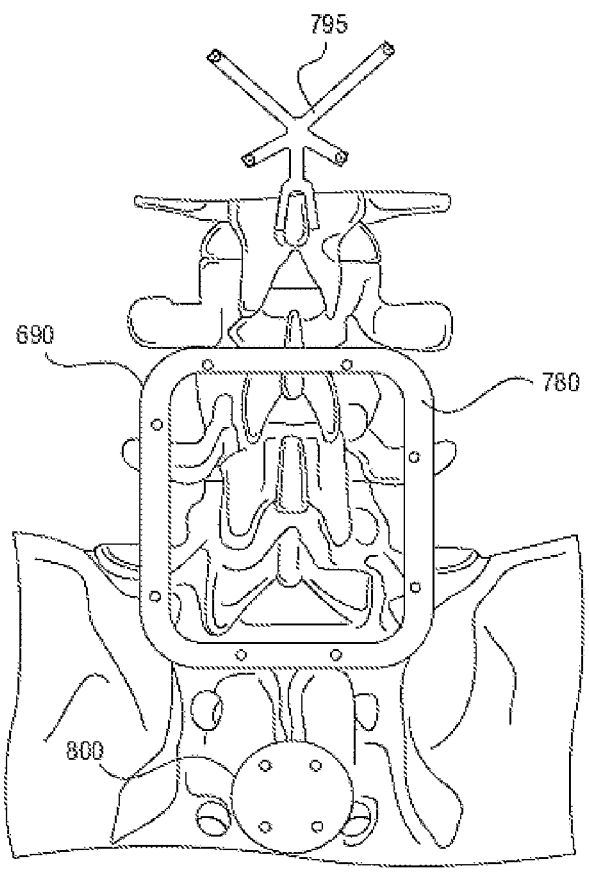
FIG. 16E
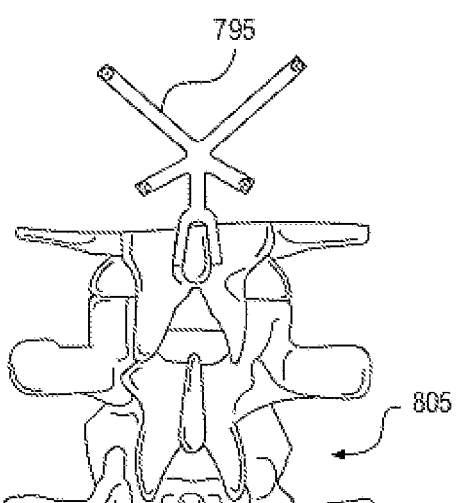
FIG. 16F
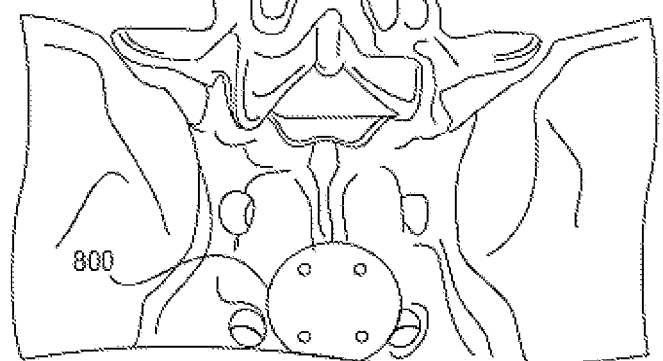

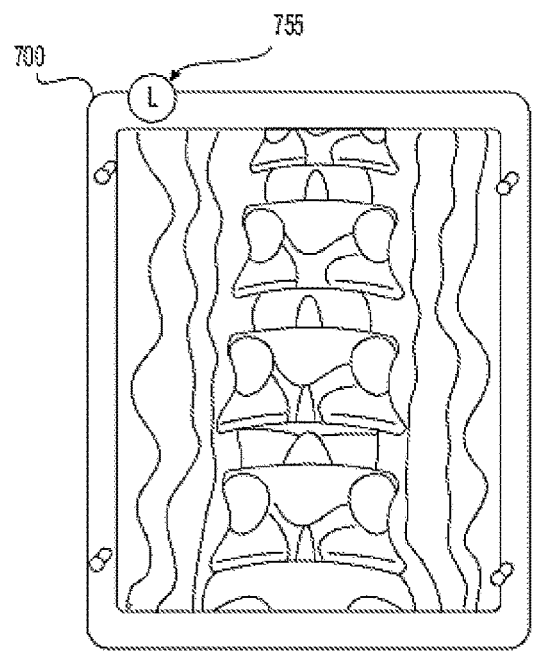 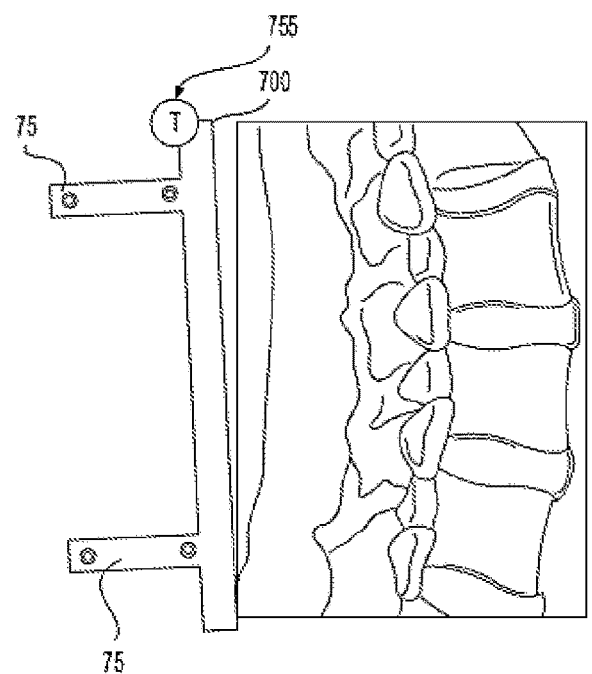
FIG. 22A          FIG. 22B
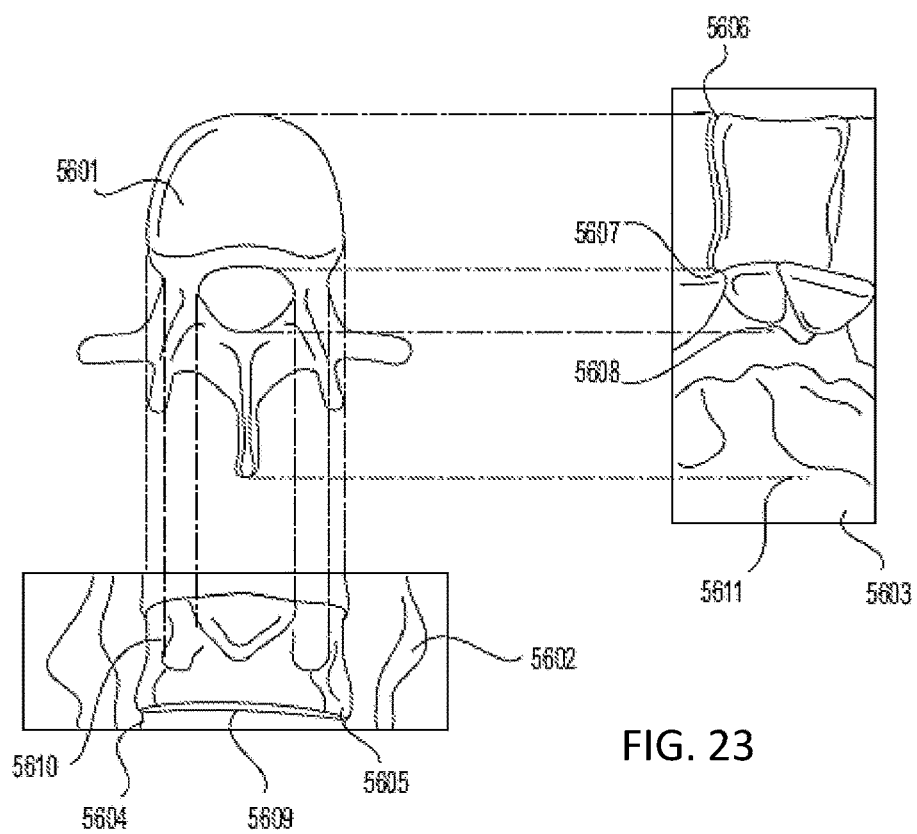
FIG. 23

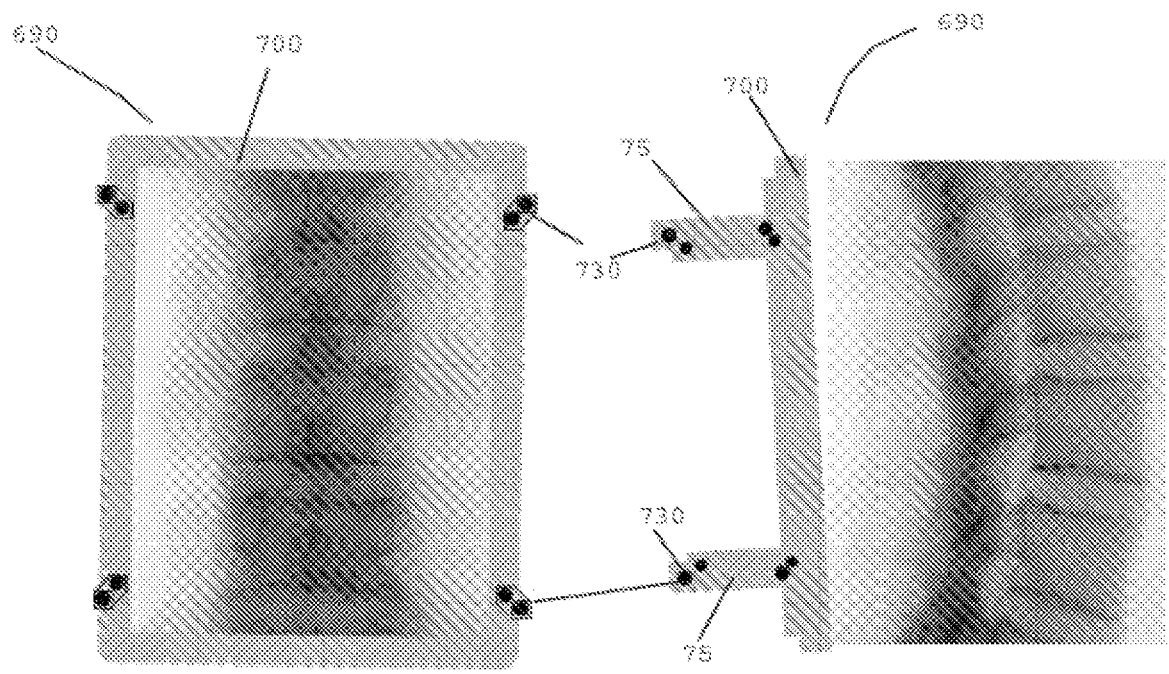
FIG. 25A  FIG. 25B
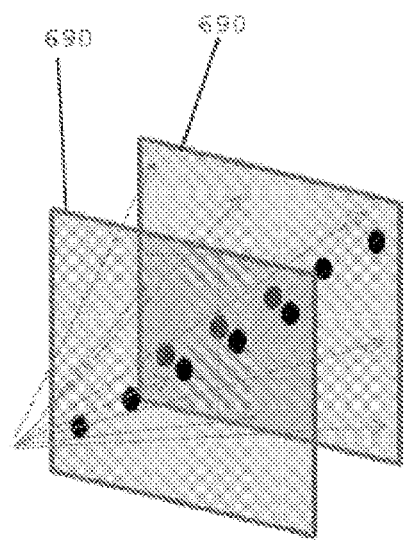 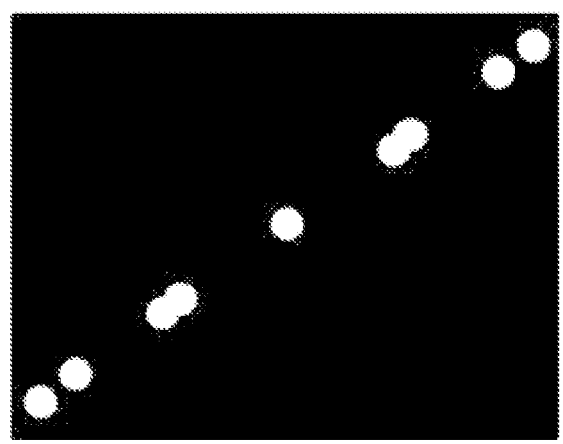
FIG. 26A  FIG. 26B

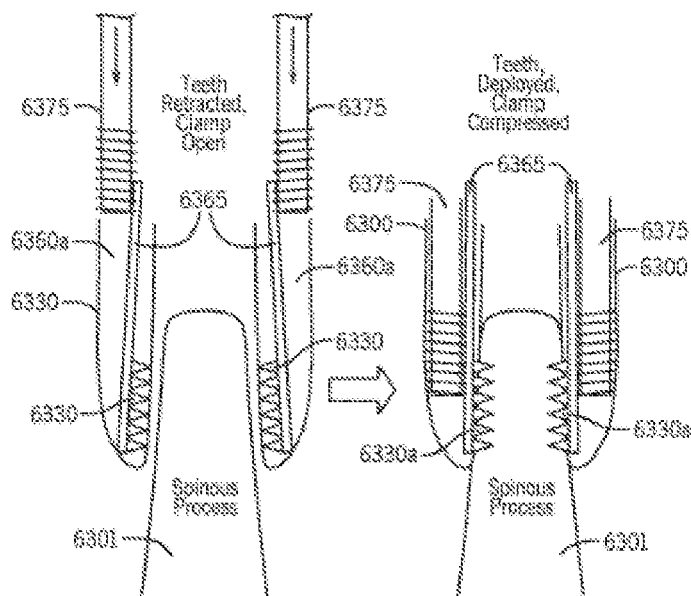
FIG. 32
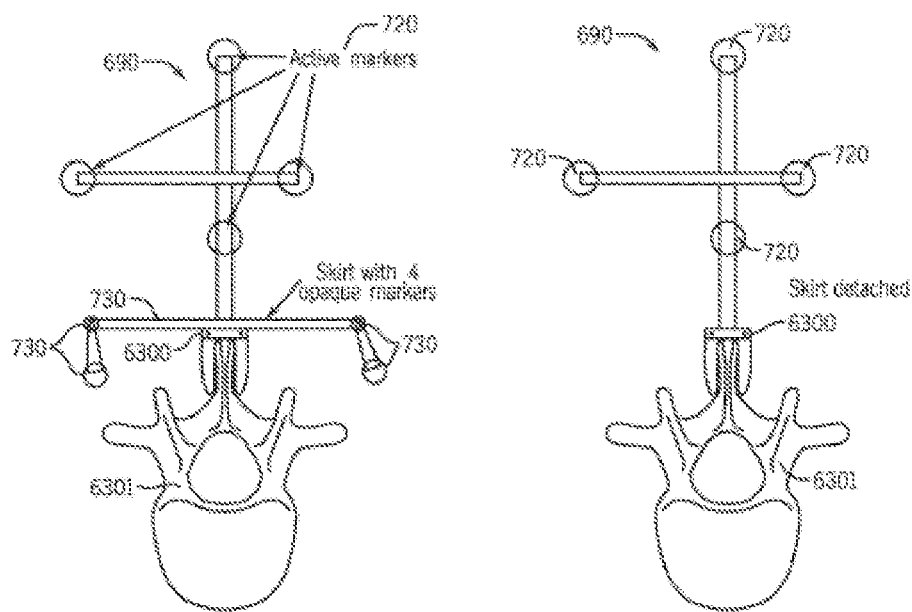
FIG. 33A
FIG. 33B

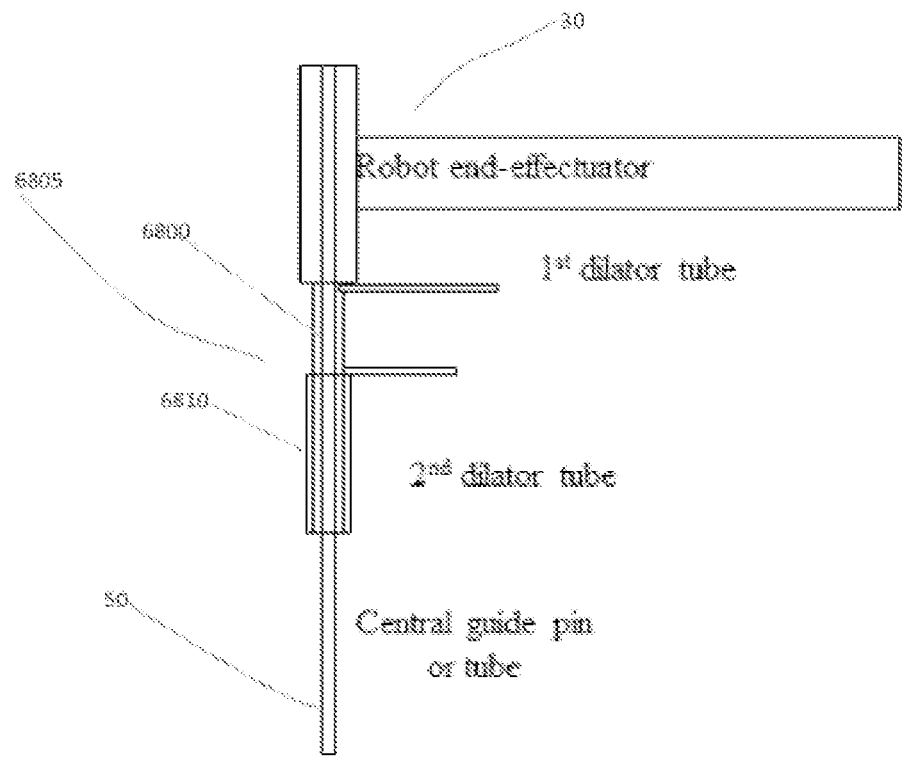
FIG. 35
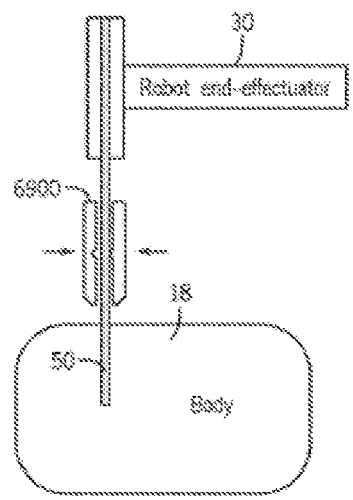 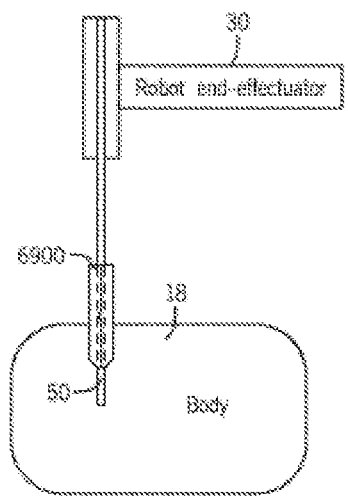 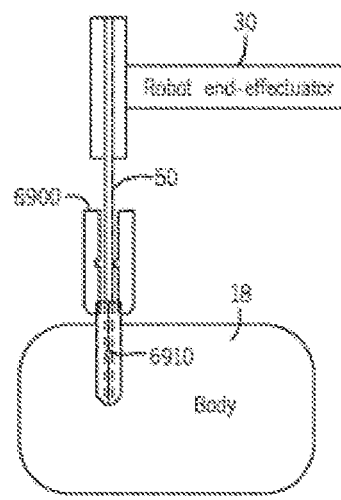
FIG. 36A          FIG. 36B          FIG. 36C

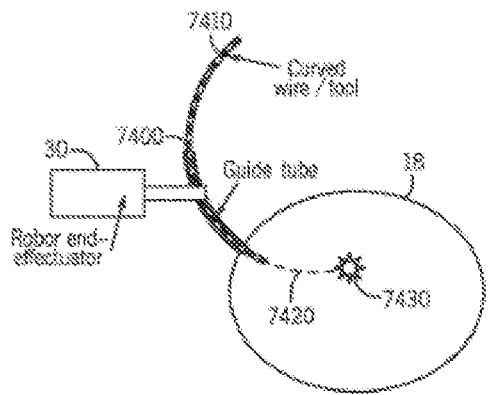 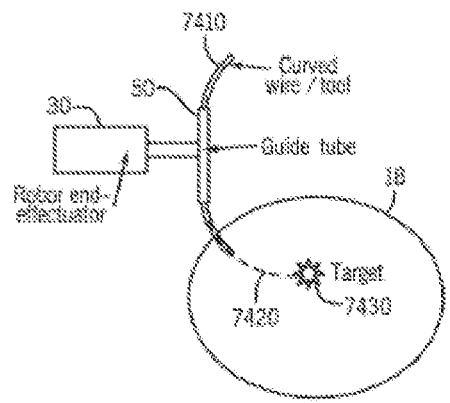
FIG. 38A  FIG. 38B
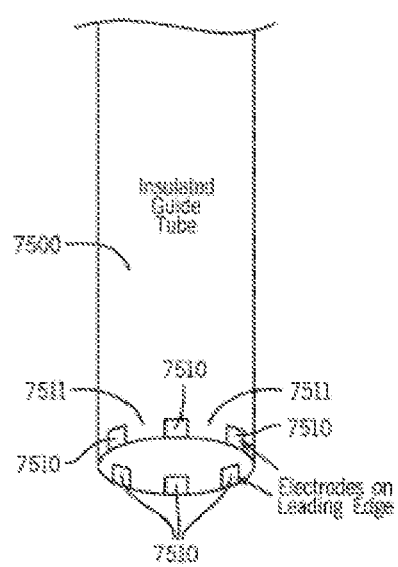
FIG. 39

SURGICAL ROBOT PLATFORM

RELATED APPLICATIONS

This application is a continuation of U.S. patent application Ser. No. 15/648,621, filed on Jul. 13, 2017 which is a continuation of U.S. patent application Ser. No. 15/609,322 filed on May 31, 2017, which is a continuation of U.S. patent application Ser. No. 13/924,505 filed on Jun. 21, 2013, all of which are incorporated herein by reference in its entirety for all purposes. Application Ser. No. 13/924,505 claims priority to U.S. Provisional Pat. App. No. 61/662,702 filed Jun. 21, 2012 and U.S. Provisional Pat. App. No. 61/800,527 filed Mar. 15, 2013, which are incorporated herein by reference in their entireties for all purposes.

BACKGROUND

Various medical procedures require the precise localization of a three-dimensional position of a surgical instrument within the body in order to effect optimized treatment. Limited robotic assistance for surgical procedures is currently available. One of the characteristics of many of the current robots used in surgical applications which make them error prone is that they use an articular arm based on a series of rotational joints. The use of an articular system may create difficulties in arriving at an accurately targeted location because the level of any error is increased over each joint in the articular system.

SUMMARY

Some embodiments of the invention provide a surgical robot (and optionally an imaging system) that utilizes a Cartesian positioning system that allows movement of a surgical instrument to be individually controlled in an x-axis, y-axis and z-axis. In some embodiments, the surgical robot can include a base, a robot arm coupled to and configured for articulation relative to the base, as well as an end-effectuator coupled to a distal end of the robot arm. The effectuator element can include the surgical instrument or can be configured for operative coupling to the surgical instrument. Some embodiments of the invention allow the roll, pitch and yaw rotation of the end-effectuator and/or surgical instrument to be controlled without creating movement along the x-axis, y-axis, or z-axis.

DESCRIPTION OF THE DRAWINGS

FIGS. 16A-16F depict illustrations of targeting fixtures in accordance with one embodiment of the invention.

FIGS. 22A-22B illustrates expected images on anteroposterior and lateral x-rays of the spine with a well aligned fluoroscopy (x-ray) machine showing a feature on the targeting fixture designed to eliminate ambiguity about directionality in accordance with one embodiment of the invention.

FIG. 23 illustrates an axial view of a spine showing how a cartoonish axial approximation of the spine can be constructed based on lateral and anteroposterior x-rays in accordance with one embodiment of the invention.

FIGS. 25A-25B illustrates expected images on anteroposterior and lateral x-rays of the spine with a well aligned fluoroscopy (x-ray) machine when parallax is present in accordance with one embodiment of the invention.

FIG. 26A illustrates two parallel plates with identically positioned radio-opaque markers in accordance with one embodiment of the invention.

FIG. 26B illustrates resulting expected x-ray demonstrating how marker overlay is affected due to parallax using the two parallel plates as shown in FIG. 26A in accordance with one embodiment of the invention.

FIGS. 31-32 illustrate embodiments of clamping piece actuation on a spinous process in accordance with some embodiments of the invention.

FIGS. 33A-33B illustrate a clamping piece modified with a targeting fixture including a temporary marker skirt and with the temporary marker skirt detached, respectively, in accordance with at least one embodiment of the invention.

FIG. 35 shows end-effectuator 30 that includes nested dilators in accordance with at least one embodiment of the invention.

FIGS. 36A-36C illustrates various embodiments of an end-effectuator including cylindrical dilator tubes in accordance with at least one embodiment of the invention.

FIGS. 38A-38B illustrate a robot end-effectuator coupled with a curved guide tube and a straight guide tube, respectively, for use with a curved or straight wire or tool in accordance with at least one embodiment of the invention.

FIG. 39 illustrates a guide tube in accordance with at least one embodiment of the invention.

DETAILED DESCRIPTION

Figure 1:
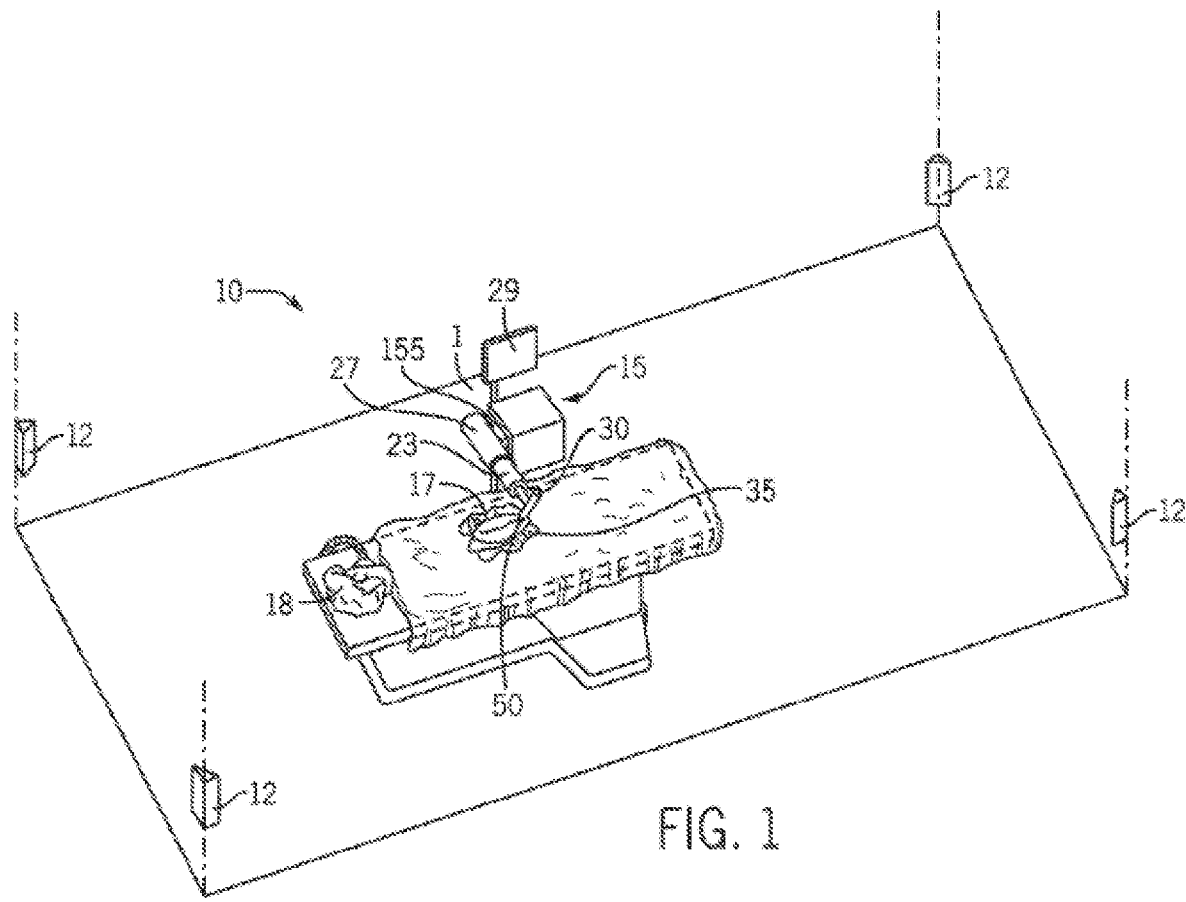
FIG. 1 is a partial perspective view of a room in which a medical procedure is taking place by using a surgical robot.
Figure 2A:
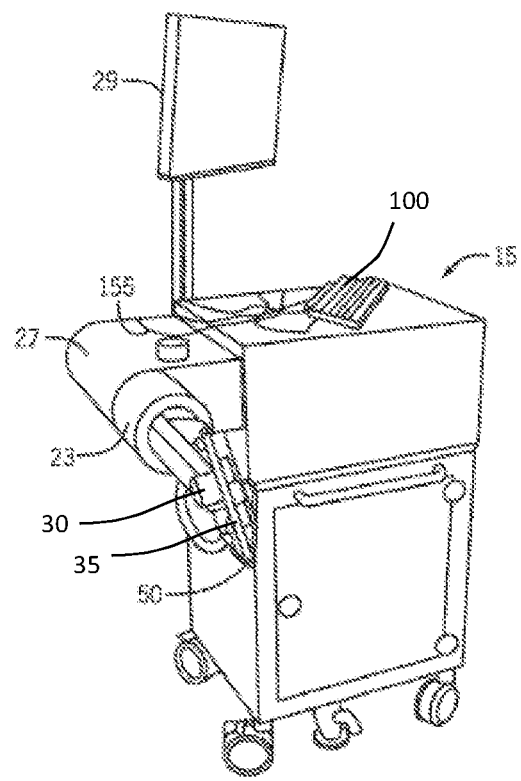
FIGS. 2A-2B display a surgical robot in accordance with one embodiment of the invention.

Referring now to FIGS. 1 and 2A, some embodiments include a surgical robot system 1 is disclosed in a room 10 where a medical procedure is occurring. In some embodiments, the surgical robot system 1 can comprise a surgical robot 15 and one or more positioning sensors 12. In this aspect, the surgical robot 15 can comprise a display means 29, and a housing 27. In some embodiments a display can be attached to the surgical robot 15, whereas in other embodiments, a display means 29 can be detached from surgical robot 15, either within surgical room 10 or in a remote location. In some embodiments, the housing 27 can comprise a robot arm 23, and an end-effectuator 30 coupled to the robot arm 23 controlled by at least one motor. For example, in some embodiments, the surgical robot system 1 can include a motor assembly 155 comprising at least one motor. In some embodiments, the end-effectuator 30 can comprise a surgical instrument 35. In other embodiments, the end-effectuator 30 can be coupled to the surgical instrument 35. As used herein, the term "end-effectuator" is used interchangeably with the terms "end-effectuator," "effectuator element," and "effectuator element." In some embodiments, the end-effectuator 30 can comprise any known structure for effecting the movement of the surgical instrument 35 in a desired manner.

In some embodiments, prior to performance of an invasive procedure, a three-dimensional ("3D") image scan can be taken of a desired surgical area of the patient 18 and sent to a computer platform in communication with surgical robot 15. In some embodiments, a physician can then program a desired point of insertion and trajectory for surgical instrument 35 to reach a desired anatomical target within or upon the body of patient 18. In some embodiments, the desired point of insertion and trajectory can be planned on the 3D image scan, which in some embodiments, can be displayed on display means 29. In some embodiments, a physician can plan the trajectory and desired insertion point (if any) on a computed tomography scan (hereinafter referred to as "CT scan") of a patient 18. In some embodiments, the CT scan can be an isocentric C-arm type scan, an O-arm type scan, or intraoperative CT scan as is known in the art. However, in some embodiments, any known 3D image scan can be used in accordance with the embodiments of the invention described herein.

In some embodiments, the surgical robot system 1 can comprise a control device (for example a computer 100 having a processor and a memory coupled to the processor). In some embodiments, the processor of the control device 100 can be configured to perform time of flight calculations as described herein. In one embodiment, the end-effectuator 30 can be a tubular element (for example a guide tube 50) that is positioned at a desired location with respect to, for example, a patient's 18 spine to facilitate the performance of a spinal surgery. In some embodiments, the guide tube 50 can be aligned with the z axis 70 defined by a corresponding robot motor or, for example, can be disposed at a selected angle relative to the z-axis 70. In either case, the processor of the control device (i.e. the computer 100) can be configured to account for the orientation of the tubular element. In some embodiments, the memory of the control device (computer 100 for example) can store software for performing the calculations and/or analyses required to perform many of the surgical method steps set forth herein.

Figure 2B:
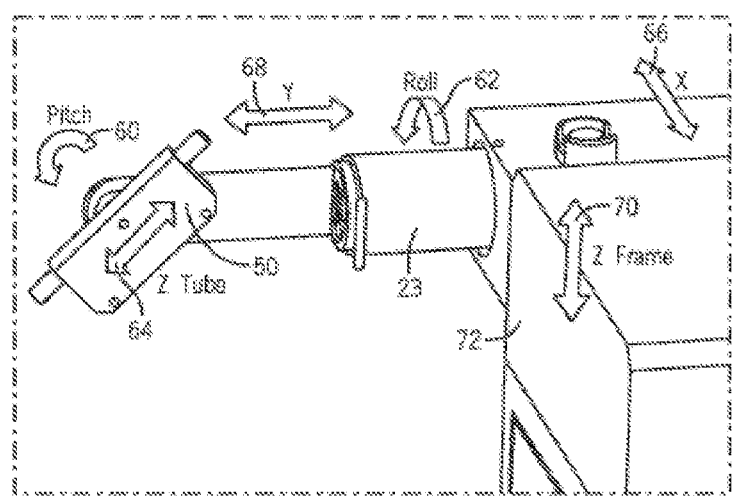

Another embodiment of the disclosed surgical robot system 1 involves the utilization of a robot 15 that is capable of moving the end-effectuator 30 along x-, y-, and z-axes (see 66, 68, 70 in FIG. 2B). In this embodiment, the x-axis 66 can be orthogonal to the y-axis 68 and z-axis 70, the y-axis 68 can be orthogonal to the x-axis 66 and z-axis 70, and the z-axis 70 can be orthogonal to the x-axis 66 and the y-axis 68. In some embodiments, the robot 15 can be configured to effect movement of the end-effectuator 30 along one axis independently of the other axes. For example, in some embodiments, the robot 15 can cause the end-effectuator 30 to move a given distance along the x-axis 66 without causing any significant movement of the end-effectuator 30 along the y-axis 68 or z-axis 70.

In some further embodiments, the end-effectuator 30 can be configured for selective rotation about one or more of the x-axis 66, y-axis 68, and z-axis 70 (such that one or more of the Cardanic Euler Angles (e.g., roll, pitch, and/or yaw) associated with the end-effectuator 30 can be selectively controlled). In some embodiments, during operation, the end-effectuator 30 and/or surgical instrument 35 can be aligned with a selected orientation axis (labeled "Z Tube" in FIG. 2B) that can be selectively varied and monitored by an agent (for example computer 100) that can operate the surgical robot system 1. In some embodiments, selective control of the axial rotation and orientation of the end-effectuator 30 can permit performance of medical procedures with significantly improved accuracy compared to conventional robots that utilize, for example, a six degree of freedom robot arm 23 comprising only rotational axes.

In some embodiments, as shown in FIG. 1, the robot arm 23 that can be positioned above the body of the patient 18, with the end-effectuator 30 selectively angled relative to the z-axis toward the body of the patient 18. In this aspect, in some embodiments, the robotic surgical system 1 can comprise systems for stabilizing the robotic arm 23, the end-effectuator 30, and/or the surgical instrument 35 at their respective positions in the event of power failure. In some embodiments, the robotic arm 23, end-effectuator 30, and/or surgical instrument 35 can comprise a conventional worm-drive mechanism (not shown) coupled to the robotic arm 23, configured to effect movement of the robotic arm along the z-axis 70. In some embodiments, the system for stabilizing the robotic arm 23, end-effectuator 30, and/or surgical instrument 35 can comprise a counterbalance coupled to the robotic arm 23. In another embodiment, the means for maintaining the robotic arm 23, end-effectuator 30, and/or surgical instrument 35 can comprise a conventional brake mechanism (not shown) that is coupled to at least a portion of the robotic arm 23, such as, for example, the end-effectuator 30, and that is configured for activation in response to a loss of power or "power off" condition of the surgical robot 15.

Referring to FIG. 1, in some embodiments, the surgical robot system 1 can comprise a plurality of positioning sensors 12 configured to receive RF signals from the at least one conventional RF transmitter (not shown) located within room 10. In some embodiments, the computer (not shown in FIG. 1) is also in communication with surgical robot 15. In some embodiments, the position of surgical instrument 35 can be dynamically updated so that surgical robot 15 is aware of the location of surgical instrument 35 at all times during the procedure. Consequently, in some embodiments, the surgical robot 15 can move the surgical instrument 35 to the desired position quickly, with minimal damage to patient 18, and without any further assistance from a physician (unless the physician so desires). In some further embodiments, the surgical robot 15 can be configured to correct the path of surgical instrument 35 if the surgical instrument 35 strays from the selected, preplanned trajectory.

In some embodiments, the surgical robot 15 can be configured to permit stoppage, modification, and/or manual control of the movement of the end-effectuator 30 and/or surgical instrument 35. Thus, in use, in some embodiments, an agent (e.g., a physician or other user) that can operate the system 1 has the option to stop, modify, or manually control the autonomous movement of end-effectuator 30 and/or surgical instrument 35. Further, in some embodiments, tolerance controls can be preprogrammed into the surgical robot 15 and/or processor of the computer platform (such that the movement of the end-effectuator 30 and/or surgical instrument 35 is adjusted in response to specified conditions being met). For example, in some embodiments, if the surgical robot 15 cannot detect the position of surgical instrument 35 because of a malfunction in the at least one RF transmitter, then the surgical robot 15 can be configured to stop movement of end-effectuator 30 and/or surgical instrument 35. In some embodiments, if surgical robot 15 detects a resistance, such as a force resistance or a torque resistance above a tolerance level, then the surgical robot 15 can be configured to stop movement of end-effectuator 30 and/or surgical instrument 35.

In some embodiments, the computer 100 for use in the system can be located within surgical robot 15, or, alternatively, in another location within surgical room 10 or in a remote location. In some embodiments, the computer 100 can be positioned in operative communication with positioning sensors 12 and surgical robot 15.

In some further embodiments, the surgical robot 15 can also be used with existing conventional guidance systems. Thus, alternative conventional guidance systems beyond those specifically disclosed herein are within the scope and spirit of the invention. For instance, a conventional optical tracking system for tracking the location of the surgical device, or a commercially available infrared optical tracking system, such as Optotrak® (Optotrak® is a registered trademark of Northern Digital Inc. Northern Digital, Waterloo, Ontario, Canada), can be used to track the patient 18 movement and the robot's base 25 location and/or intermediate axis location, and used with the surgical robot system 1. In some embodiments in which the surgical robot system 1 comprises a conventional infrared optical tracking system, the surgical robot system 1 can comprise conventional optical markers attached to selected locations on the end-effectuator 30 and/or the surgical instrument 35 that are configured to emit or reflect light. In some embodiments, the light emitted from and/or reflected by the markers can be read by cameras (for example with cameras 8200 shown in FIG. 48) and/or optical sensors and the location of the object can be calculated through triangulation methods (such as stereo-photogrammetry).

As described earlier, the end-effectuator 30 can comprise a surgical instrument 35, whereas in other embodiments, the end-effectuator 30 can be coupled to the surgical instrument 35. In some embodiments, arm 23 can be connected to the end-effectuator 30, with surgical instrument 35 being removably attached to the end-effectuator 30.

In some embodiments, the surgical robot 15 is moveable in a plurality of axes (for instance x-axis 66, y-axis 68, and z-axis 70) in order to improve the ability to accurately and precisely reach a target location. Some embodiments include a robot 15 that moves on a Cartesian positioning system; that is, movements in different axes can occur relatively independently of one another instead of at the end of a series of joints.

Figure 3:
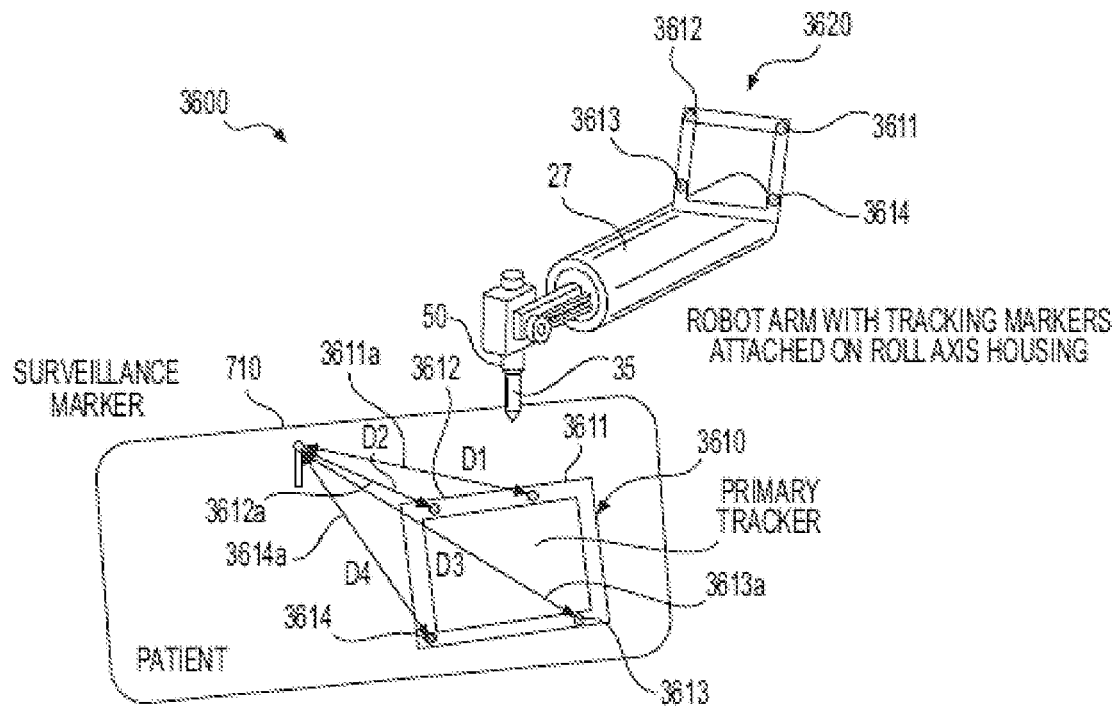
FIG. 3 illustrates a surgical robot system having a surveillance marker in accordance with one or more embodiments described herein.

FIG. 3 illustrates an example embodiment 3600 of surgical robot system 1 that utilizes a surveillance marker 710 in accordance with one or more aspects of the invention. As illustrated, the example embodiment 3600 comprises a 4-marker tracker array 3610 attached to the patient 18 and having a surveillance marker, and a 4-marker tracker array 3620 on the robot 15. In some embodiments, during usage, it may possible that a tracker array, or tracker (3610 in FIG. 3), on a patient 18 inadvertently shifts. For example, a conventional clamp positioned on a patient's 18 spinous process 2310 where the tracker 3610 is attached can be bumped by the surgeon's arm and move (i.e., bend or translate) to a new position relative to the spinous process 2310. Alternatively, a tracker 3610 that is mounted to the skin of the patient 18 can move gradually with the skin, as the skin settles or stretches over time. In this instance, the accuracy of the robot 15 movement can be lost because the tracker 3610 can reference bony anatomy from a medical image that no longer is in the same position relative to the tracker as it had been during the medical image scan. To overcome such problems, some embodiments of the invention provide a surveillance marker 710 as illustrated in FIG. 3. As shown, in some embodiments, the surveillance marker 710 can be embodied or can comprise one or more markers 710 rigidly affixed to a patient 18 in a location different than the location in which a primary tracker array 3610 is affixed; for example, a different spinous process 2310, on the skin, or on a small post drilled into the ilium. Accordingly, in some embodiments, the surveillance marker 710 can be located on the same rigid body as the primary tracker array 3610 but at a different location on the rigid body.

In one embodiment, in response to placement of the surveillance marker 710, execution of a control software application (e.g., robotic guidance software) can permit an agent (e.g., a surgeon, a nurse, a diagnostician) to select "set surveillance marker". At this time, the vector (3D) distances between the surveillance marker 710, and each of the markers 3611, 3612, 3613, and 3614 on the primary tracker array 3610 can be acquired and retained in computer 100 memory (such as a memory of a computing device executing the control software application). In an embodiment in which a 4-marker tracker array 3610 is utilized (FIG. 3), four distances 3611a, 3612a, 3613a, and 3614a can be acquired and retained, representing the distances between the surveillance marker 710 and markers 3611, 3612, 3613, and 3614. In such embodiment, at each frame of real-time data during a procedure, the surgical robot system 1 disclosed herein can calculate updated distances between each of the markers 3611, 3612, 3613, and 3614 on the primary tracker array 3610 and the surveillance marker 710. The system 1 can then compare the updated distances or a metric thereof (for example, the sum of the magnitude of each distance) to the available values (for example, values retained in the computer 100 memory). In some embodiments, in view that the surveillance marker 710 and tracker array 3610 can be on the same rigid body, the updated distances and/or the metric thereof (such as their sum) can remain substantially fixed unless one or more of the tracker array 3610 or the surveillance marker 710 shifts. In some embodiments, in response to a shift of the tracker array 3610 or the surveillance marker 710, or both, a notification can be issued to alert an agent of a loss in movement accuracy. In some embodiments, if the surveillance marker 710 offset exceeds a pre-set amount, operation of the surgical robot system 1 can be halted. In some embodiments, in response to a user intentionally shifting the tracker array 3610 or the surveillance marker 710 to a new position, execution of the control software application can permit overwriting a set of one or more stored distances with new values for comparison to subsequent frames.

In some embodiments, as illustrated in FIG. 3, embodiment 3600 of surgical robot system 1 utilizes a surveillance marker 710, a 4-marker tracker array 3610 attached to the patient 18, and a 4-marker tracker array 3620 on the robot 15. It should be appreciated that in some embodiments, the 4-marker tracker array 3620 on the robot 15 can experience an unintentional shift in a manner similar to that for the 4-marker array tracker 3610 on the patient 18. Consequently, in certain embodiments, a surveillance marker (not shown) can be attached to a different position on the robot 15 arm than the robot's 4-marker tracker array 3620 to control, at least in part, such unintentional shift. In some embodiments, a surveillance marker on the robot 15 may provide lesser efficiencies than a surveillance marker 710 on the patient 18 in view that the robot 15 arm can be manufactured with negligible or minimal likelihood of the robot's tracker array 3620 or surveillance marker (not shown) shifting. In addition or in the alternative, other embodiments can include means for registering whether the tracker 3620 has shifted can be contemplated for the robot's tracker array 3620. For instance, in some embodiments, the means for registering may not include a surveillance marker, but may comprise the extant robot 15 tracking system and one or more of the available conventional encoders. In some embodiments, the system 1 and encoder(s) can compare movement registered from the tracker 3620 to movement registered from counts of encoders (not shown) on each robot 15 axis. For example, in some embodiments where the robot's tracker array 3620 is mounted on the housing 27 that rotates with the roll 62 axis (which can be farther away from the base 25 than the z-axis 70, x-axis 66, y-axis 68, and roll 62 axis) then changes in z-axis 70, x-axis 66, y-axis 68, and roll 62 axis encoder counts can provide highly predictable changes in the position of the robot's tracker array 3620 in the coordinate systems of the tracking system and robot 15. In some embodiments, the predicted movement based on encoder counts and tracked 3D position of the tracker array 3620 after application of known counts can be compared and, if the values differ substantially (or values are above a predetermined threshold), the agent can be alerted to the existence of that an operational issue or malfunction. The operational issue can originate from one or more of a malfunction in the registration of counts (i.e., electromechanical problem), malfunction in registration of the tracker's markers 3621, 3622, 3623, 3624 (for example, outside of tracking system's optimum volume), or shift in the position of the tracker 3620 on the robot's 15 surface during the move.

It should be appreciated that other techniques (for example, methods, systems, and combinations thereof, or the like) can be implemented in order to respond to operational issues that may prevent tracking of the movement of a robot 15 in the surgical robot system 1. In one embodiment, marker reconstruction can be implemented for steadier tracking. In some embodiments, marker reconstruction can maintain the robot end-effectuator 30 steady even if an agent partially blocks markers during operation of the disclosed surgical robot system 1.

Figure 4:
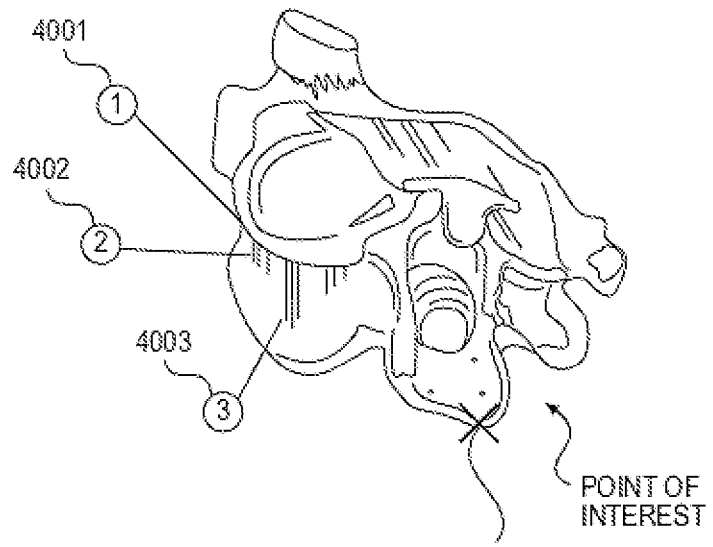
FIG. 4 illustrates an example of a methodology for tracking a visual point on a rigid body using an array of three attached markers in accordance with one embodiment of the invention.

As described herein, in some embodiments, at least some features of tracking movement of the robot's end-effectuator 30 can comprise tracking a virtual point on a rigid body utilizing an array of one or more markers 720, such tracking comprising one or more sequences of translations and rotations. As an illustration, an example methodology for tracking a visual point on a rigid body using an array of three attached markers is described in greater detail herein, such methodology can be utilized to implement marker reconstruction technique in accordance with one or more aspects of the invention. FIG. 4, for example, illustrates an example of a methodology for tracking a visual point 4010 on a rigid body using an array of three attached markers 4001, 4002, 4003. In some embodiments, the method includes contemplating a reference data-frame. In some embodiments, the reference data-frame can be associated with a set of reproducible conditions for the relative positions of the markers 4001, 4002, 4003, but not necessarily defined locations.

Figure 5:
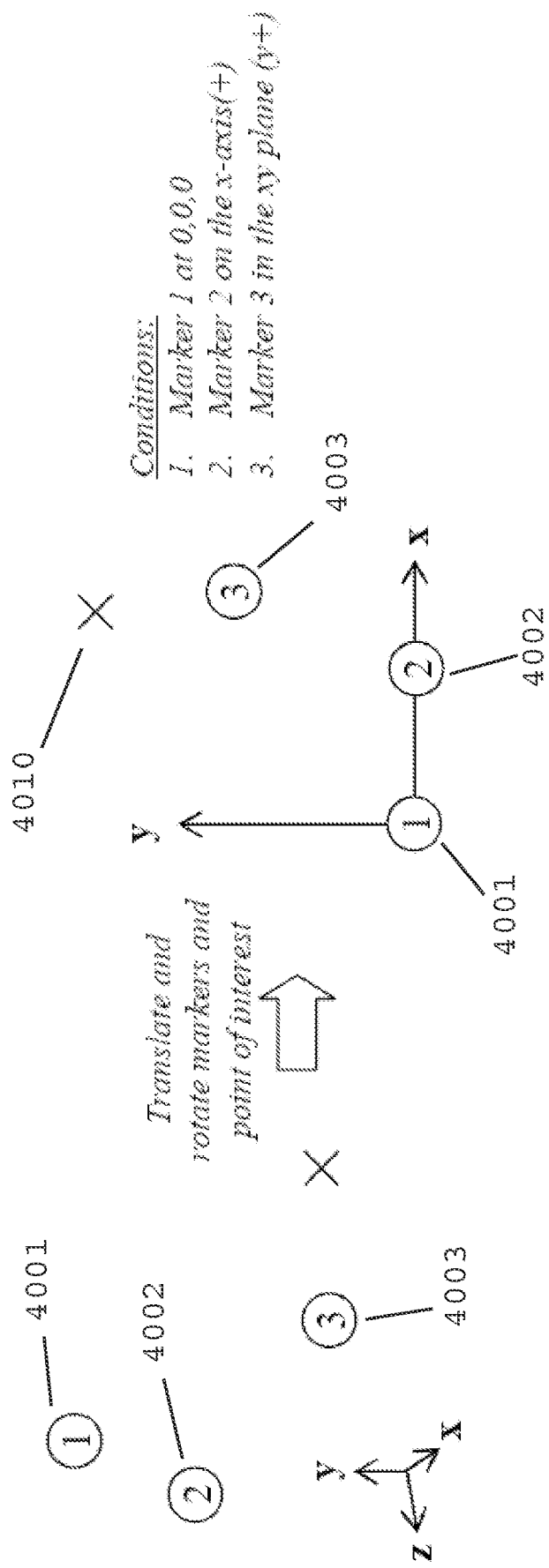
FIG. 5 illustrates a procedure for monitoring the location of a point of interest relative to three markers based on images received form the methodology illustrated in FIG. 4.

FIG. 5 illustrates a procedure for monitoring the location of a point of interest 4010 relative to three markers 4001, 4001, 4003 based on images received form the methodology illustrated in FIG. 4 in accordance with some embodiments of the invention. As shown, the method includes translation and rotating the markers 4001, 4002, 4003 and point of interest 4010 with the conditions as shown. In some embodiments, the method can include saving the x-axis, y-axis, and z-axis coordinates of the point of interest 4010 in this reference frame for future use. In some embodiments, for each subsequent data-frame the method can include the steps of; 1) transform the markers 4001, 4002, 4003 using the conditions defined for the reference frame (keeping track of the rotations and translations), 2) add the point of interest 4010 (which was saved after establishing the reference frame) and 3) transform the point of interest 4010 back to the current location of the markers 4001, 4002, 4003 using inverses of the saved translations and rotations from step 1. In some embodiments, upon or after completing step 1 above, the actual proximity of the markers 4001, 4002, 4003 to their original reference data-frame is dictated by marker noise and rigid body rigidity. In some embodiments, the markers will never overlay perfectly with their counterparts that were stored when establishing the reference frame. In some embodiments, the disclosed method can permit the markers 4001, 4002, 4003 to get as close as possible to their original relative spacing.

Figure 6A:
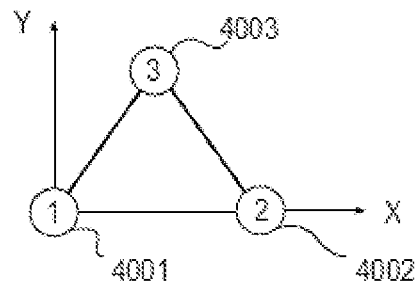
FIGS. 6A-6F illustrates examples of tracking methodology based on an array of three attached markers in accordance with one embodiment of the invention.
Figure 6D:
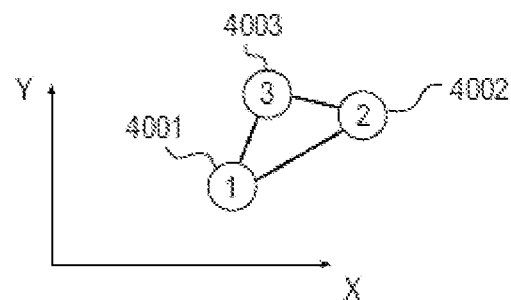
Figure 6B:
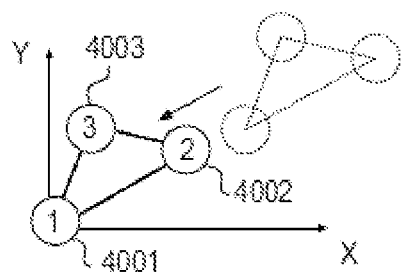
Figure 6E:
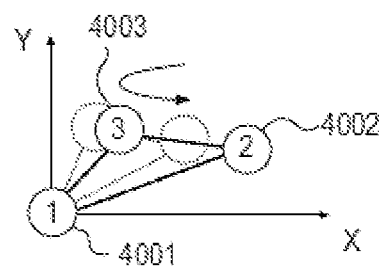
Figure 6C:
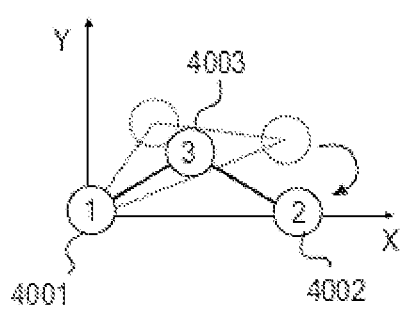
Figure 6F:
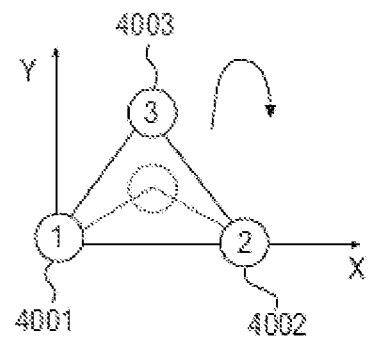

FIGS. 6A-6F illustrate examples of tracking methodology based on an array of three attached markers 4001, 4002, and 4003 in accordance with some embodiments of the invention. In some embodiments, the goal can be marker 4001 on the origin, marker 4002 on the positive x-axis, and marker 4003 in the x-y plan in a positive y direction (shown in FIG. 6A). Assuming a starting configuration as shown in FIG. 6B, in some embodiments, the method can include translating the rigid body so that marker 4001 is at the origin as shown in FIG. 6C. In some embodiments, the method can then include rotation about the y-axis so that marker 4002 is in the x-y plane (i.e., z=0) (see FIG. 6D). In some embodiments, the method can then include rotating the z-axis so that marker 4002 is at y=0, x coordinate positive (as shown in FIG. 6E). Finally, in some embodiments, the method can include rotating about the x-axis so that marker 4003 is at z=0, y coordinate positive. In some embodiments, a record of the translations and rotations can be retained in order to utilize the negative values to transform position(s) back after adding the point of interest. In some embodiments, when translating the rigid body so that the marker 4001 moves to the origin, the vector to add to each marker's position vector is simply the negative 4001 position vector. In some embodiments, to determine the values of θ to plug into the rotation matrices in steps 2, 3, and 4, use the arctangent. For example, rotate marker 4002 about the y-axis to z=0 where:

$$M2 = \begin{bmatrix} 4 \\ 5 \\ 6 \end{bmatrix}$$

Figure 7:
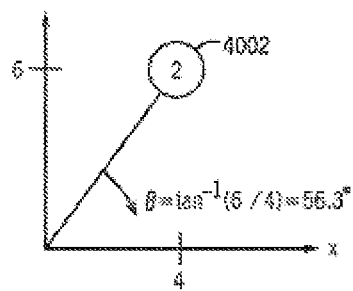
FIG. 7 illustrates an example of a two dimensional representation for rotation about the Y-axis in accordance with one embodiment of the invention.

FIG. 7 illustrates an example of a two dimensional representation for rotation about the y-axis in accordance with some embodiments of the invention. As shown, FIG. 7 illustrates one embodiment showing a two-dimensional representation looking down the axis about which rotation occurs (e.g., y-axis is going into the page). In this example, a position rotation of θ=56.3° about the y-axis is needed to bring 4002 to z=0. It should be appreciated that the appropriate direction (+ or −) of the rotation angle to plug into the rotation matrix can be confusing. In some embodiments, it is beneficial to draw the plane of the rotation with the rotation axis coming out of the plane contained in the page surface (for example, the right-hand rule can provide a suitable orientation), then a counterclockwise rotation is positive and a clockwise rotation is negative. In the foregoing example, the axis was going into the page surface, thus a clockwise rotation was positive.

Figure 8A:
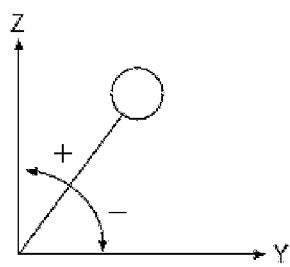
FIG. 8A-8C illustrate alternative representations of a two dimensional representation for rotation about an X-axis in accordance with one embodiment of the invention.
Figure 8B:
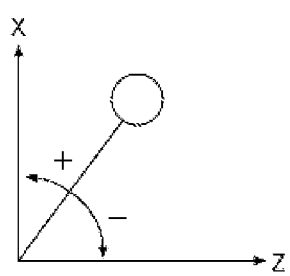
Figure 8C:
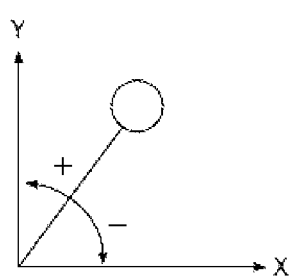

FIGS. 8A-8C illustrates an alternative representation of two dimensional representations for rotations about the axis, depicting how each plane can be drawn for counterclockwise positive and clockwise negative in accordance with some embodiments of the invention. As shown, FIG. 8A illustrates an alternative representation of a two dimensional representation for rotation about an X-axis. FIG. 8B illustrates an alternative representation of a two dimensional representation for rotation about a Y-axis. FIG. 8C illustrates an alternative representation of a two dimensional representation for rotation about a Z-axis In some embodiments, to rotate the rigid body about the y-axis so that 4002 is in the x-y plane (z=0):

$$\theta_y = +\tan^{-1}\left(\frac{4002_z}{4002_x}\right)$$

In some embodiments, to rotate the rigid body about the z-axis so that 4002 is at y=0, $$\theta_z = -\tan^{-1}\left(\frac{4002_y}{4002_x}\right)$$

In some embodiments, to rotate the rigid body about the x-axis so that 4003 is at z=0:

$$\theta_x = -\tan^{-1}\left(\frac{4003_z}{4003_y}\right)$$

Figure 9:
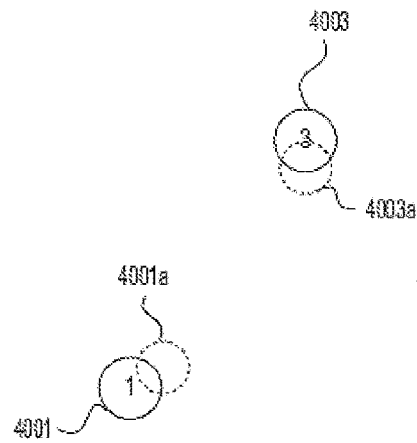
FIG. 9 provides a depiction of a noise within a frame of data.

As described herein, the example method to transform markers 4001, 4002, 4003 as close as possible to the reference frame can comprise; 1) translate the rigid body so that 4001 is at the origin (0,0,0), and 2) rotate about the y-axis so that 4002 is in the x-y plane (i.e., z=0), and 3) rotate about the z-axis so that 4002 is at y=0, x coordinate positive, and 4). rotate about the x-axis so that 4003 is at z=0, y coordinate positive. In other embodiments, a method to reach the same reference can comprise: 1) translate the rigid body so that 4001 is at the origin (0,0,0), and 2) rotate about the x-axis so that 4002 is in the x-y plane (i.e., z=0), and 3) rotate about the z-axis so that 4002 is at y=0, x coordinate positive, 4) rotate about the x-axis so that 4003 is at z=0, y coordinate positive. It should be appreciated that there are other possible methods and related actions, both in the reference frame chosen and in how the rigid body is manipulated to get it there. The described method is simple, but does not treat markers equally. The reference frame requires 4001 to be restricted the most (forced to a point), 4002 less (forced to a line), and 4003 the least (forced to a plane). As a result, errors from noise in markers are manifested asymmetrically. For example, consider a case where in a certain frame of data, noise causes each of the three markers to appear farther outward than they actually are or were (represented by 4001a, 4002a, and 4003a) when the reference frame was stored (as depicted in FIG. 9.)

Figure 10:
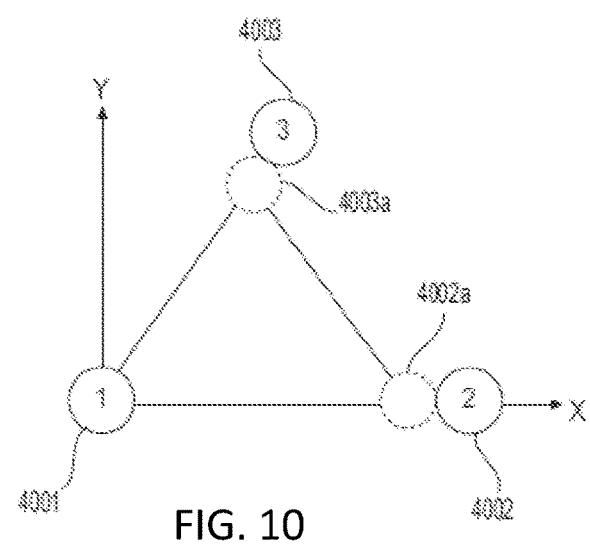
FIG. 10 illustrates the depiction of a noise within a frame of data as shown in FIG. 9 with a stored point of interest.

In some embodiments, when the transformations are done to align the apparent markers "as close as possible" to their stored reference position, they will be offset. For example, when the stored point of interest is added, it will be misplaced in a direction on which marker was chosen as 4001 in the algorithm (see 4003, 4003a and 4002, 4002a for example in FIG. 10).

Some embodiments provide additional or alternative methods for tracking points of interest that can involve more symmetrical ways of overlaying the actual marker positions with the stored reference positions. For example, in some embodiments, for three markers 4001, 4002, 4003, a two-dimensional fitting method typically utilized in zoology can be implemented. (See, e.g., Sneath P. H. A., "Trend-surface analysis of transformation grids," J. Zoology 151, 65-122 (1967)). The method can include a least squares fitting algorithm for establishing a reference frame and transforming markers to lie as close as possible to the reference. In this case, the reference frame is the same as described earlier except that the common mean point (hereinafter referred to as "CMP") is at the origin instead of marker 4001. In some embodiments, the CMP after forcing the markers into the x-y plane is defined in the following equation (and can be represented in FIG. 11):

$$CMP = \begin{bmatrix} \bar{x} \\ \bar{y} \\ 0 \end{bmatrix} = \begin{bmatrix} (M1_x + M2_x + M3_x)/3 \\ (M1_y + M2_y + M3_y)/3 \\ 0 \end{bmatrix}$$

In some embodiments, for the markers to be centered around CMP, the markers can be translated by subtracting the CMP from 4001, 4002, and 4003. It should be noted that the point of interest being tracked is not included in determining $CMP_{ref}$.

In some embodiments, the method to transform markers as close as possible to this reference frame can comprise; 1) translating the rigid body so that 4001 is at the origin (0,0,0), and 2) rotating about the y-axis so that 4002 is in the x-y plane (i.e., z=0), and 3) rotating about the z-axis so that 4002 is at y=0, x coordinate positive into the x-ray plane, and 4) rotating about the x-axis so that 4003 is at z=0, y coordinate positive, and finally 5) calculate the CMP for the markers 4001, 4002, 4003 and translating the rigid body so that the CMP is at the origin (i.e., subtract the CMP from each point transformed). In some embodiments, steps 1-5 are done for the original set of markers for which the position of the point of interest was known and for the new set for which you are adding the point of interest. A further step can be included for the new set, for example, 6) rotate about the z-axis to best overlay the stored reference markers. In some embodiments, the rotation angle θ is found using the formula from Sneath:

$$\tan\theta = \frac{\Sigma x_{pos2} y_{ref} - \Sigma x_{ref} y_{pos2}}{\Sigma x_{ref} x_{pos2} + \Sigma y_{ref} y_{pos2}}$$

In some embodiments, if M1, M2, M3 denote the stored reference markers and M'1, M'2, M'3 denote the position being tracked in this data-frame, the equation can be written:

$$\tan^{-1} = \begin{bmatrix} (M'1_x M1_y + M'2_x M2_y + M'3_x M3_y) - \\ (M1_x M'1_y + M2_x M'2_y + M3_x M'3_y) \\ \hline (M1_x M'1_x + M2_x M'2_x + M3_x M'3_x) + \\ (M1_y M'1_y + M2_y M'2_y + M3_y M'3_y) \end{bmatrix}$$

It should be noted that this rotation angle can be small (e.g., smaller than about 1). In some embodiments, after the markers 4001, 4002, 4003 are overlaid, some embodiments of the invention can include adding the point of interest then transforming the point of interest back to its true present location in the current frame of data. In some embodiments, to transform back, negative values saved from the forward transformation steps 1-6 as discussed above can be utilized. That is, for instance, go from step 6 to step 5 by rotating by negative θ, go from step 5 to step 4 by adding the CMP, etc.)

Figure 11:
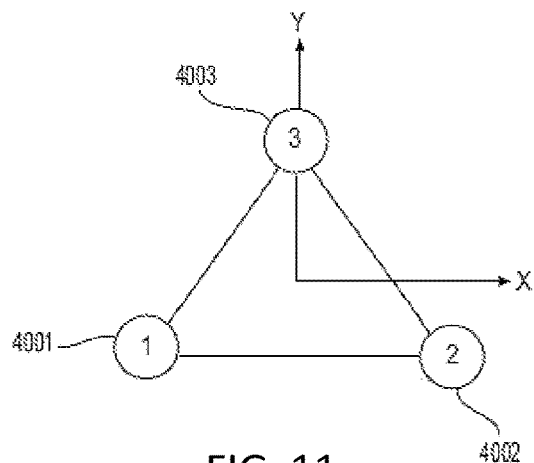
FIG. 11 illustrates a depiction of results of applying a least squares fitting algorithm for establishing a reference frame and transforming markers in accordance with one embodiment of the invention.
Figure 12:
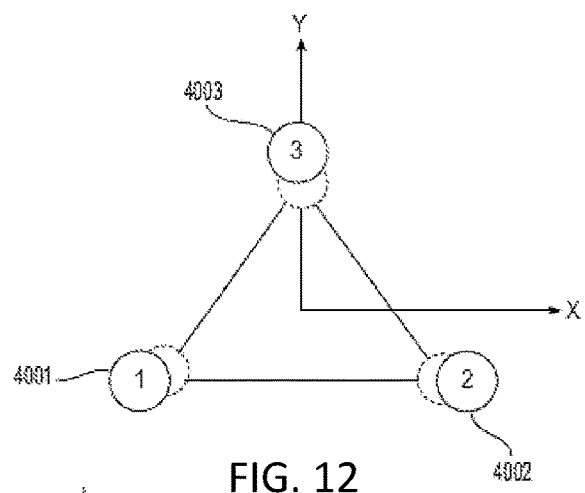
FIG. 12 illustrates a depiction of results of applying a least squares fitting algorithm for establishing a reference frame and transforming markers as shown in FIG. 11 including noise.

In some embodiments, using this least-squares algorithm, noise is manifested more symmetrically and the point of interest will probably be calculated to be closer to its actual location. This can be illustrated in FIG. 12, which illustrates a depiction of results of applying a least squares fitting algorithm for establishing a reference frame and transforming markers 4001, 4002, 4003 as shown in FIG. 11 including noise. Regardless of which method is used, it can be beneficial to monitor the error between the marker locations at a given frame of data and the reference marker locations. In some embodiments, the method can include calculating and sum the vector distances of each marker and report the value in mm.

Figure 13:
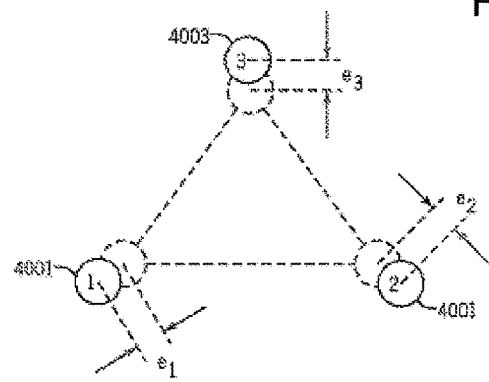
FIG. 13 illustrates a depiction of error calculation for reference frame markers in accordance with one embodiment of the invention.

FIG. 13 for example illustrates a depiction of error calculation for reference frame markers in accordance with some embodiments of the invention. In some embodiments, by continuously displaying this error value, the agent can be alerted if markers 4001, 4002, 4003 have become partially obscured, or if a marker 4001, 4002, 4003 is no longer securely or rigidly attached to the rigid body. In some embodiments, when performing a best fit on more than 3 markers, they cannot be forced into a plane, and therefore the problem becomes much more difficult. In some embodiments, one solution is to inspect all or nearly all possible triangles formed by groups of 3 markers 4001, 4002, 4003 and evaluate which one gives the least standard deviation of the angles of the vertices. See Chèze L, Fregly B. J., Dimnet J: Technical note: A solidification procedure to facilitate kinematic analyses based on video system data," Journal of Biomechanics 28(7), 879-884 (1995). In some other embodiments, the method can include calculating a least squares fit of the vertices of the geometric shape, requiring iteration to perform matrix decomposition (i.e., Newton-Raphson method). For example, see Veldpaus F E, Woltring H J, Dortmans L J M G, 'A least-squares algorithm for the equiform transformation from spatial marker co-ordinates', Journal of Biomechanics 21(1), 45-54 (1988).

In some embodiments, when tracking 3D movement of a rigid body (for example, a robot 15 end-effectuator 30 or a targeted bone) using an array of 3 tracking markers 4001, 4002, 4003 that are rigidly attached to the rigid body, one example method for quantifying motion can include determining the transformations (translation and rotations) for the movement from a first (neutral) position (defined here as "A") to second (current frame) position (herein referred to as "B"). In some embodiments, it may be convenient to describe the rotations as a three by three orientation matrix (direction cosines) of the rigid body in the position B, and to treat the three translation values as a 3×1 vector containing the x, y, z coordinates of the origin of the position A coordinate system transformed to position B. In some embodiments, the direction cosine matrix is a 3×3 matrix, the columns of which contain unit vectors that originally were aligned with the x, y, and z axes, respectively, of the neutral coordinate system. In some embodiments, to build a direction cosine matrix, a 3×3 matrix, A, can be defined in a manner that its columns are unit vectors, i, j, and k, aligned with the x, y, and z axes, respectively:

$$A = \begin{bmatrix} i_x & j_x & k_x \\ i_y & j_y & k_y \\ i_z & j_z & k_z \end{bmatrix} = \begin{bmatrix} 1 & 0 & 0 \\ 0 & 1 & 0 \\ 0 & 0 & 1 \end{bmatrix}$$

Upon or after rotations of the coordinate system occur, in some embodiments, the new matrix (which is the direction cosine matrix, A') is as follows, where the unit vectors i', j', and k' represent the new orientations of the unit vectors that were initially aligned with the coordinate axes:

$$A' = \begin{bmatrix} i'_x & j'_x & k'_x \\ i'_y & j'_y & k'_y \\ i'_z & j'_z & k'_z \end{bmatrix}$$

In some embodiments, to determine the direction cosines and translation vector, the origin and unit vectors can be treated as aligned with the coordinate axes as four tracked points of interest in the manner described herein. For example, if the origin (o) and three unit vectors (i, j, k) are aligned with the coordinate axes, they are treated as virtual tracked points of interest with coordinates of:

$$o = \begin{bmatrix} 0 \\ 0 \\ 0 \end{bmatrix} \to i = \begin{bmatrix} 1 \\ 0 \\ 0 \end{bmatrix} \to j = \begin{bmatrix} 0 \\ 1 \\ 0 \end{bmatrix} \to k = \begin{bmatrix} 0 \\ 0 \\ 1 \end{bmatrix}$$

In some embodiments, these points of interest can provide the direction cosines and translation for the movement when moved along with the three markers from position A to position B. In some embodiments, it may be convenient to implement (for example execute) the method for moving the virtual points to these four points placed into a 3×4 matrix, P.

In some embodiments, the matrix is as follows in position A:

$$P = \begin{bmatrix} o_x & i_x & j_x & k_x \\ o_y & i_y & j_y & k_y \\ o_z & i_z & j_z & k_z \end{bmatrix} = \begin{bmatrix} 0 & 1 & 0 & 0 \\ 0 & 0 & 1 & 0 \\ 0 & 0 & 0 & 1 \end{bmatrix}$$

In some embodiments, the matrix is as follows in position B:

$$P' = \begin{bmatrix} a_x & b_x & c_x & d_x \\ a_y & b_y & c_y & d_y \\ a_z & b_z & c_z & d_z \end{bmatrix} = \begin{bmatrix} o'_x & i'_x + o'_x & j'_x + o'_x & k'_x + o'_x \\ o'_y & i'_y + o'_y & j'_y + o'_y & k'_y + o'_y \\ o'_z & i'_z + o'_z & j'_z + o'_z & k'_z + o'_z \end{bmatrix}$$

In some embodiments, after movement, the direction cosine matrix is $$A' = \begin{bmatrix} i'_x & j'_x & k'_x \\ i'_y & j'_y & k'_y \\ i'_z & j'_z & k'_z \end{bmatrix} = \begin{bmatrix} b_x - a_x & c_x - a_x & d_x - a_x \\ b_y - a_y & c_y - a_y & d_y - a_y \\ b_z - a_z & c_z - a_z & d_z - a_z \end{bmatrix}$$

Figure 14:
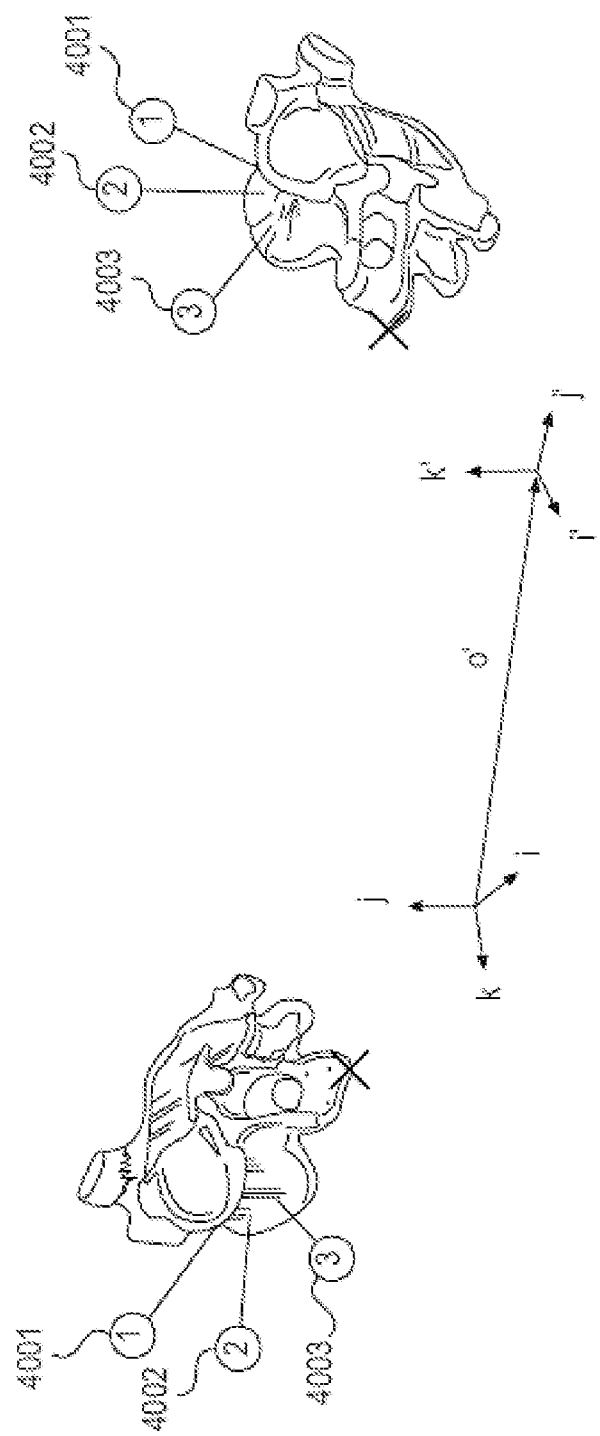
FIG. 14 illustrates a graphical representation of methods of tracking three dimensional movement of a rigid body.

In some embodiments, the vector o' represents the new position of the origin. In some embodiments, after moving the three markers 4001, 4002, 4003 from position A to position B, and bringing the four points (as a 3×4 matrix) along with the three markers 4001, 4002, 4003, the translation of the origin is described by the first column. Further, in some embodiments, the new angular orientation of the axes can be obtained by subtracting the origin from the $2^{nd}$, $3^{rd}$, and $4^{th}$ columns. These methods should be readily apparent from the following graphic representation in FIG. 14, which illustrates a graphical representation of methods of tracking three dimensional movement of a rigid body.

In some embodiments, if more than three markers 4001, 4002, 4003 are utilized for tracking the movement of a rigid body, the same method can be implemented repeatedly for as many triads of markers as are present. For example, in a scenario in which four markers, M1, M2, M3, and M4, are attached to the rigid body, there can be four triads: those formed by {M1, M2, M3}, {M1, M2, M4}, {M1, M3, M4}, and {M2, M3, M4}. In some embodiments, each of these triads can be used independently in the method described hereinbefore in order to calculate the rigid body motion. In some embodiments, the final values of the translations and rotations can then be the average of the values determined using the four triads. In some embodiments, in the alternative or in addition, other methods for achieving a best fit when using more than 3 markers may be used.

In some embodiments, when tracking with four markers, in a scenario in which one of the four markers becomes obscured, it can be desirable to switch to tracking the rigid body with the remaining three markers instead of four. However, this change in tracking modality can cause a sudden variation in the results of one or more calculations utilized for tracking. In some embodiments, the variation can occur because the solution from the one remaining triad may be substantially different than the average of 4 triads. In some embodiments, if using the tracked position of the rigid body in a feedback loop to control the position of a robot 15 end-effectuator, the sudden variation in results of the calculation can be manifested as a physical sudden shift in the position of the robot 15 end-effectuator 30. In some embodiments, this behavior is undesirable because the robot 15 is intended to hold a guide tube 50 steady with very high accuracy.

Some embodiments include an example method for addressing the issue of sudden variation that occurs when one of the four markers M1, M2, M3, M4 is blocked, thereby causing the position to be calculated from a single triad instead of the average of four triads, can include reconstructing the blocked marker as a virtual marker. In some embodiments, to implement such reconstructing step with high accuracy, the most recent frame of data in which all four markers M1, M2, M3, M4 are visible can be retained substantially continuously or nearly continuously (for example in a memory of a computing device implementing the subject example method). In some embodiments, if all four markers M1, M2, M3, M4 are in view, the x-axis, y-axis, and z-axis coordinates of each of the four markers M1, M2, M3, and M4 are stored in computer 100 memory. It should be appreciated that in some embodiments, it may be unnecessary to log all or substantially all frames and is sufficient to overwrite the same memory block with the most recent marker coordinates from a full visible frame. Then, in some embodiments, at a frame of data in which one of the four markers M1, M2, M3, and M4 is lost, the lost marker's position can be calculated based on the remaining triad, using the example method described herein for remaining three markers. That is, the triad (the three visible markers) is transformed to a reference. The stored set of markers is then transformed to the same reference using the corresponding triad with the fourth marker now acting as a virtual landmark. The recovered position of the lost fourth marker can then be transformed back to the current position in space using the inverse of the transformations that took it to the reference position. In some embodiments, after the lost marker's position is reconstructed, calculation of the rigid body movement can be performed as before, based on the average of the fourth triads, or other best fit method for transforming the rigid body from position A to position B.

In some embodiments, an extension to the methods for reconstructing markers 720 is to use multiple ambiguous synchronized lines of sight via multiple cameras 8200 tracking the same markers 720. For example, two or more cameras 8200 (such as Optotrak® or Polaris®) could be set up from different perspectives focused on the tracking markers 720 on the targeting fixture 690 or robot 15. In some embodiments, one camera unit could be placed at the foot of a patient's bed, and another could be attached to the robot 15. In some embodiments, another camera unit could be mounted to the ceiling. In some embodiments, when all cameras 8200 substantially simultaneously view the markers 720, coordinates could be transformed to a common coordinate system, and the position of any of the markers 720 would be considered to be the average (mean) of that marker's three dimensional position from all cameras used. In some embodiments, even with extremely accurate cameras, an average is needed because with system noise, the coordinates as perceived from different cameras would not be exactly equal. However, when one line of sight is obscured, the lines of sight from other cameras 8200 (where markers 720 can still be viewed) could be used to track the robot 15 and targeting fixture 690. In some embodiments, to mitigate twitching movements of the robot 15 when one line of sight is lost, it is possible that the marker 720 positions from the obscured line of sight could be reconstructed using methods as previously described based on an assumed fixed relationship between the last stored positions of the markers 720 relative to the unobstructed lines of sight. Further, in some embodiments, at every frame, the position of a marker 720 from camera 1 relative to its position from camera 2 would be stored; then if camera 1 is obstructed, and until the line of sight is restored, this relative position is recalled from computer memory (for example in memory of a computer platform) and a reconstruction of the marker 720 from camera 1 would be inserted based on the recorded position of the marker from camera 2. In some embodiments, the method could compensate for temporary obstructions of line of sight such as a person standing or walking in front of one camera unit.

In certain embodiments, when a marker M1, M2, M3, M4 is lost but is successfully reconstructed in accordance with one or more aspect described herein, the marker that has been reconstructed can be rendered in a display device. In one example implementation, circles representing each marker can be rendered graphically, coloring the circles for markers M1, M2, M3, M4 that are successfully tracked in green, markers M1, M2, M3, M4 that are successfully reconstructed in blue, and markers M1, M2, M3, M4 that cannot be tracked or reconstructed in red. It should be appreciated that such warning for the agent can serve to indicate that conditions are not optimal for tracking and that it is prudent to make an effort for all four tracking markers to be made fully visible, for example, by repositioning the cameras or standing in a different position where the marker is not blocked. Other formats and/or indicia can be utilized to render a virtual marker and/or distinguish such marker from successfully tracked markers. In some embodiments, it is possible to extend the method described herein to situations relying on more than four markers. For example, in embodiments in which five markers are utilized on one rigid body, and one of the five markers is blocked, it is possible to reconstruct the blocked marker from the average of the four remaining triads or from another method for best fit of the 4 remaining markers on the stored last visible position of all 5 markers. In some embodiments, once reconstructed, the average position of the rigid body is calculated from the average of the 10 possible triads, {M1,M2,M3}, {M1,M2,M4}, {M1,M2,M5}, {M1,M3,M4}, {M1,M3,M5}, {M1,M4,M5}, {M2,M3,M4}, {M2,M3,M5}, {M2,M4,M5}, and {M3,M4,M5} or from another method for best fit of 5 markers from position A to position B.

Figure 15:
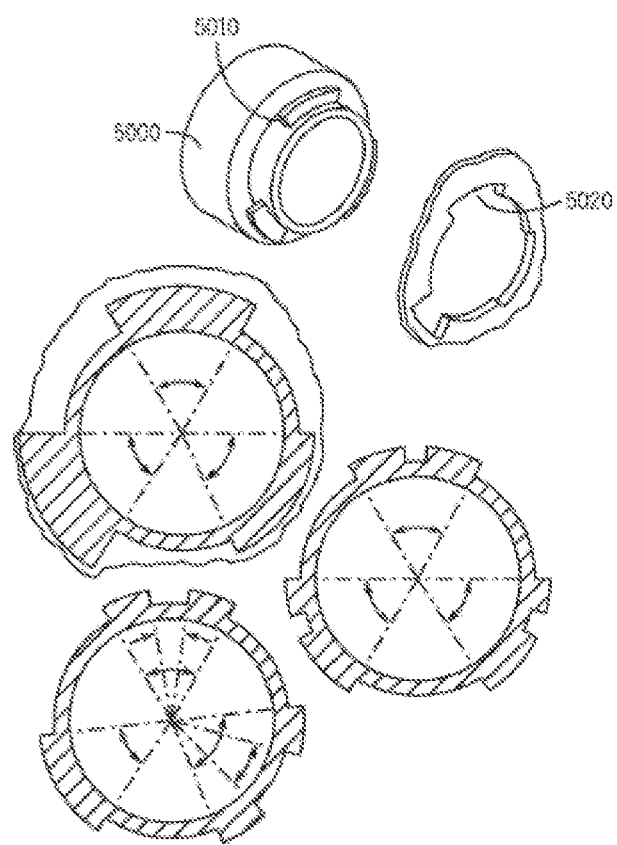
FIG. 15 shows a perspective view illustrating a bayonet mount used to removably couple the surgical instrument to the end-effectuator in accordance with one embodiment of the invention.

As discussed above, in some embodiments, the end-effectuator 30 can be operatively coupled to the surgical instrument 35. This operative coupling can be accomplished in a wide variety of manners using a wide variety of structures. In some embodiments, a bayonet mount 5000 is used to removably couple the surgical instrument 35 to the end-effectuator 30 as shown in FIG. 15. For example, FIG. 15 shows a perspective view illustrating a bayonet mount 5000 used to removably couple the surgical instrument 35 to the end-effectuator 30. In some embodiments, the bayonet mount 5000 securely holds the surgical instrument 35 in place with respect to the end-effectuator 30, enabling repeatable and predictable location of operational edges or tips of the surgical instrument 35.

In some embodiments, the bayonet mount 5000 can include ramps 5010 which allow identification of the surgical instrument 35 and ensure compatible connections as well. In some embodiments, the ramps 5010 can be sized consistently or differently around a circumference of the bayonet mount 5000 coupled to or integral with the surgical instrument 35. In some embodiments, the differently sized ramps 5010 can engage complementary slots 5020 coupled to or integral with the end-effectuator 30 as shown in FIG. 15.

In some embodiments, different surgical instruments 35 can include different ramps 5010 and complementary slots 5020 to uniquely identify the particular surgical instrument 35 being installed. Additionally, in some embodiments, the different ramps 5010 and slots 5020 configurations can help ensure that only the correct surgical instruments 35 are installed for a particular procedure.

In some embodiments, conventional axial projections (such as those shown in U.S. Pat. No. 6,949,189 which is incorporated herein as needed to show details of the interface) can be mounted to or adjacent the ramps 5010 in order to provide automatic identification of the surgical instruments 35. In some embodiments, other additional structures can be mounted to or adjacent the ramps 5010 in order to provide automatic identification of the surgical instruments 35. In some embodiments, the axial projections can contact microswitches or a wide variety of other conventional proximity sensors in order to communicate the identity of the particular surgical instrument 35 to the computing device or other desired user interface. Alternatively, in some other embodiments of the invention, the identity of the particular surgical instrument 35 can be entered manually into the computing device or other desired user interface.

Figure 16A:
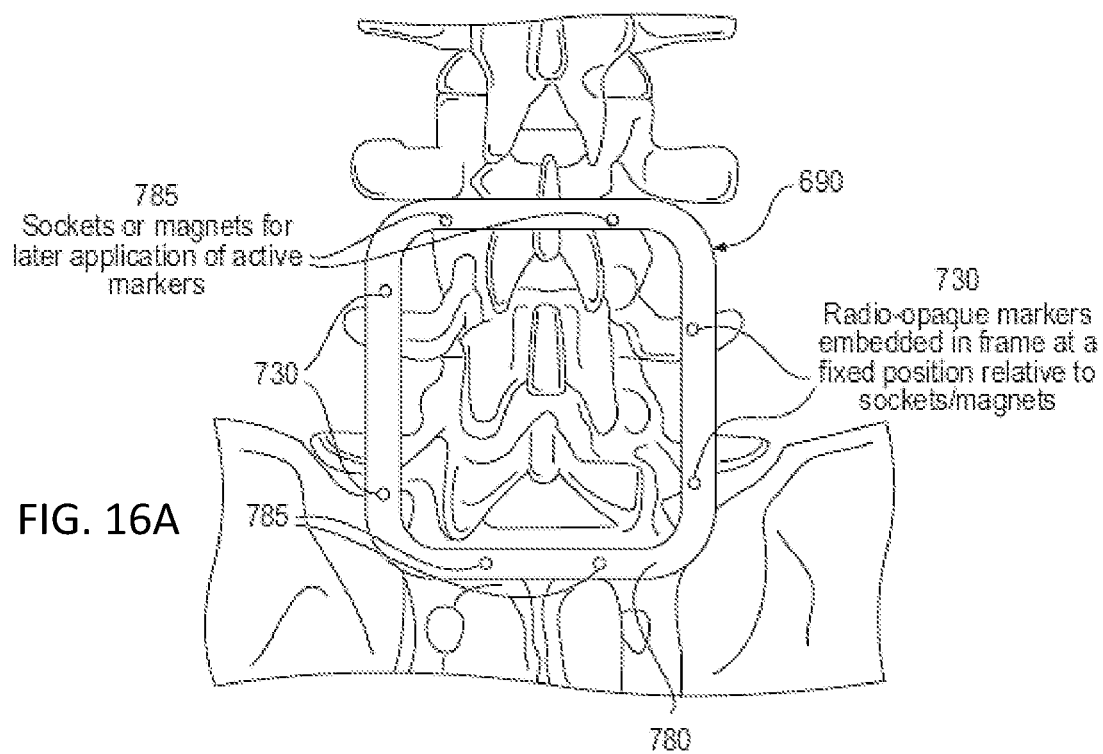
Figure 16B:
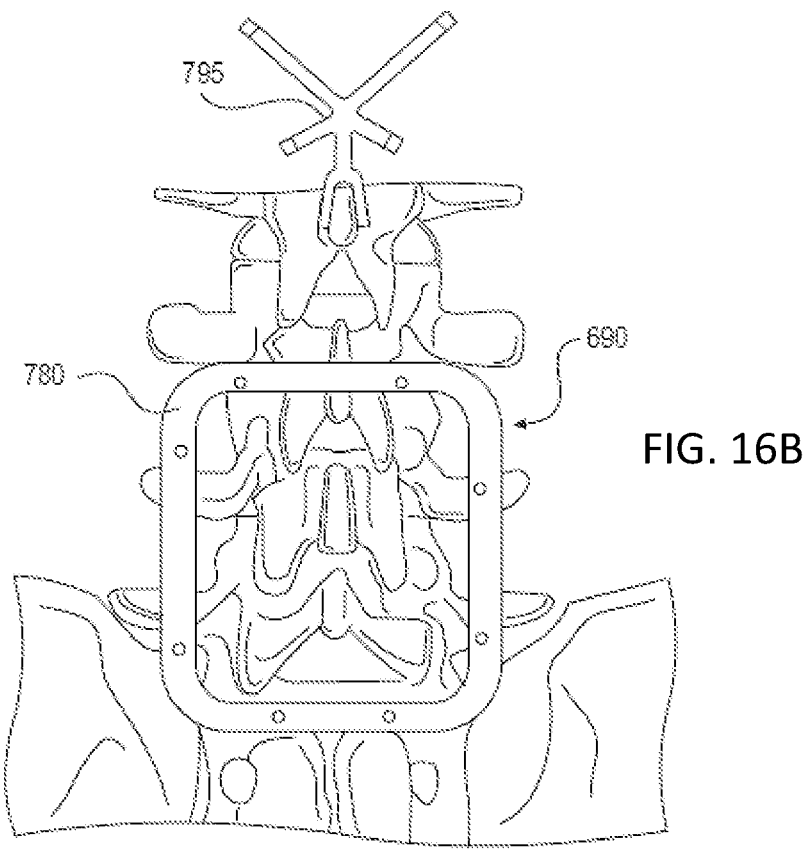
Figure 16C:
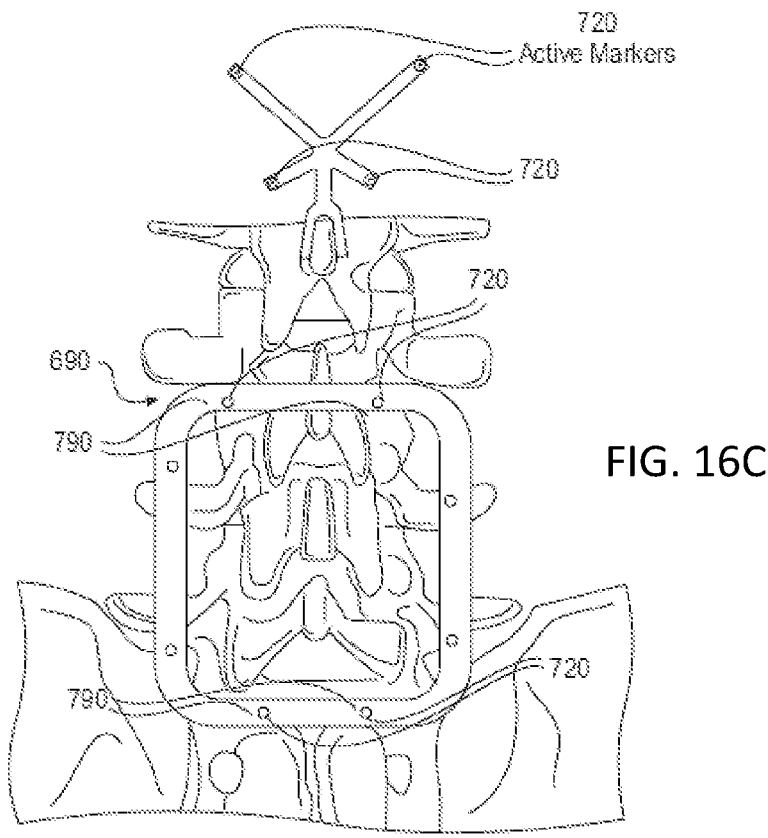
Figure 16D:
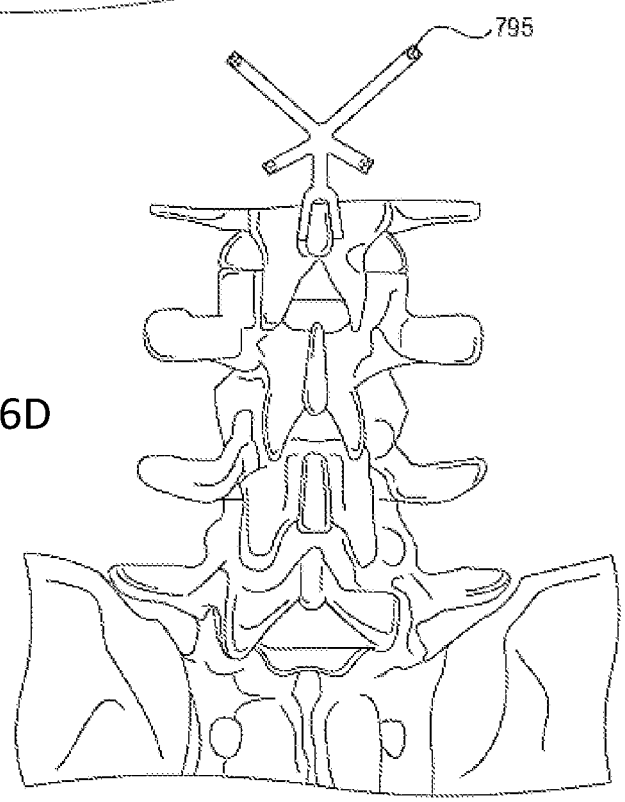

In some embodiments, instead of a targeting fixture 690 consisting of a combination of radio-opaque 730 and active markers 720, it is possible to register the targeting fixture 690 through an intermediate calibration. For example, in some embodiments, an example of such a calibration method could include attaching a temporary rigid plate 780 that contains radio-opaque markers 730, open mounts 785 (such as snaps, magnets, Velcro, or other features) to which active markers 720 can later be attached in a known position. For example, see FIGS. 16A-F which depict illustrations of targeting fixtures 690 coupled to a spine portion 19 of a patient 18 in accordance with one embodiment of the invention). The method can then include scanning the subject (using for example CT, MRI, etc.), followed by attaching a percutaneous tracker 795 such as those described earlier or other array of 3 or more active markers 720 rigidly affixed to the anatomy 19 as for example in FIG. 16B, and then attaching active markers 720 to the temporary plate 780 in the known positions dictated by the snaps, magnets, velcro, etc., as illustrated in FIG. 16C. In some embodiments, a further step can include activating the cameras 8200 to read the position of the tracker 795 rigidly affixed to the anatomy 19 at the same time as the active markers 720 on the temporary plate 780. This step establishes the position of the active markers 720 on the temporary plate 780 relative to the radio-opaque markers 730 on the temporary plate 780 as well as the positions of the active markers 720 on the tracker 795 relative to the active markers 720 on the temporary plate 780, and therefore establishes the position of the anatomy relative to the active markers 720 on the tracker 795. The temporary plate 780 can be removed (as illustrated in FIG. 16D), including the active markers 720 and radio-opaque markers 730. These markers are no longer needed because registration has been performed relative to the active markers on the rigidly affixed tracker 795.

In some alternative embodiments, variants of the order of the above described steps may also be used. For instance, the active markers 720 could already be attached at the time of the scan. This method has advantage that the radio-opaque markers 730 can be positioned close to the anatomy of interest without concern about how they are attached to the tracker 795 with active markers 720. However, it has the disadvantage that an extra step is required in the registration process. In some embodiments, a variant of this method can also be used for improved accuracy in which two trackers of active markers 720 are attached above and below the region of interest. For example, a tracker rostral to the region of interest (shown as 795) could be a spinous process 2310 clamp in the upper lumbar spine and a tracker caudal to the region of interest (shown as 800) could be a rigid array of active markers 720 screwed into the sacrum (see for example FIG. 16E). After calibration, the temporary plate 780 is removed and the area between the two trackers (within the region 805) is registered (see for example FIG. 16F).

Some embodiments can include methods for transferring registration. For example, a registration performed to establish the transformations in order to transpose from a medical image coordinate system (such as the CT-scanned spine) to the coordinate system of the cameras, can later be transferred to a different reference. In the example described in the above related to FIGS. 16A-16F, a temporary fixture 780 with radio-opaque markers 730 and active markers 720 is placed on the patient 18 and registered. Then, a different fixture 795 is attached to the patient with active markers 720 only. Then the cameras (for example, camera 8200) are activated, and the active markers 720 on the temporary plate 780 are viewed simultaneously with the active markers 720 on the new tracking fixture 795. The necessary transformations to get from the temporary markers (those on the temporary plate 780) to the new markers (i.e. the markers on fixture 795) are established, after which the temporary plate 780 can be removed. In other words, the registration was transferred to a new reference (fixture 795). In some embodiments, it should be possible to repeat this transferal any number of times. Importantly, in some embodiments, one registration can also be duplicated and transferred to multiple references. In some embodiments, transferal of registration to multiple references would provide a means for tracking relative motion of two rigid bodies. For example, a temporary targeting fixture may be used to register the anatomy to the cameras 8200. Then, two new targeting fixtures may be placed on separate bones that are both included in the medical image used for registration. If the registration from the temporary targeting fixture is transferred to both of the new targeting fixtures, both of these bones may be tracked simultaneously, and the position of the robot end effectuator 30 or any other tracked probe or tool relative to both bones can be visualized. If one bone then moves relative to the other, the end effectuator's position would be located differently relative to the two trackers and the two medical images (for example, see FIGS. 17B-17D showing the two trackers 796 and 797 positioned on a portion of spine 19).

In some embodiments, after registration is transferred to both trackers 796, 797, the robot end effectuator 30 may be perceived by both trackers 796, 797 to be positioned as shown. In some embodiments, it is possible that one of the bones to which a tracker is mounted moves relative to the other, as shown in exaggerated fashion in FIG. 17C. In some embodiments, if the end effectuator 30 is considered fixed, the perception by the tracking system and software would be that the spine 19 was positioned in two possible relative locations, depending on which tracker is followed (see for example, the representation in FIG. 17D). Therefore, in some embodiments, by overlaying representations of both medical images, it becomes possible to visualize the relative movement of the bones on which the trackers 796, 797 are attached. For example, instead of displaying the re-sliced medical image on the screen and showing the position of the robot end effectuator 30 relative to that image, two re-sliced medical images could be overlapped (each allowing some transparency) and simultaneously displayed, showing one position where the robot end effectuator currently is positioned relative to both images (see FIGS. 17E-17F). However, the duplication of bones would make the representation cluttered, and therefore in some embodiments, it can be possible to automatically or manually segment the medical image such that only bones that do not move relative to a particular tracker 796, 797 are represented on the image (shown in FIG. 17E with the bones 19a highlighted as in relation to bone regions meaningful to tracker 796 with regions 19b faded, and FIG. 17F with the bones 19a highlighted in relation to bone regions meaningful to tracker 797, with regions 19b faded). Segmenting would mean hiding, fading, or cropping out the portion of the 3D medical image volume that the user does not want to see (represented as the faded regions 19b in FIGS. 17E and 17F).

In some embodiments, segmentation could involve identifying bordering walls on the 3D image volume or bordering curves on 2D slices comprising the medical image. In some embodiments, by segmenting simple six-sided volumes, enough separation of critical elements could be visualized for the task. In some embodiments, bones on the slice from a CT scans depicted in FIGS. 17G and 17H are shown with segmentation into region 20a, corresponding to the bone regions 19a referred to in FIGS. 17E and 17F, and 20b, corresponding to region 19b. In some embodiments, the regions 20a and 20b can be represented in different shades of color (for example, blue for 20a and yellow for 20b). Furthermore, as shown, the segmentation as displayed is depicted to proceed in and out of the page to include the entire CT volume. Moreover, although it goes right through the disc space, this segmentation cuts through one spinous process 2310 in the image in FIG. 17G, and does not follow the facet joint articulations to segment independently moving bones, as shown in a different slice represented in FIG. 17H. However, the re-sliced images of these overlapped volumes should still be useful when placing, for example, pedicle screws since the pedicles are properly segmented in the images.

An example of transferal of registration to multiple trackers includes conventional pedicle screw placement followed by compression or distraction of the vertebrae. For example, if pedicle screws are being placed at lumbar vertebrae L4 and L5, a tracker could be placed on L3 and registered. In some embodiments, conventional pedicle screws could then be placed at L4 and L5, with extensions coming off of each screw head remaining after placement. In some embodiments, two new trackers (for example, trackers substantially similar to 796, 797) could then be attached to the extensions on the screw heads, one at L4 and one at L5. Then, the registration could be transferred to both of these new trackers and a tracker at L3 could be removed or thereafter ignored. In some embodiments, if the medical image is segmented so that L4 and rostral anatomy is shown relative to the tracker on L4 (while L5 and caudal anatomy is shown relative to the tracker on L5), then it can be possible to see how the L4 and L5 vertebrae move relative to one another, as compressive or distractive forces are applied across that joint. In some embodiments, such compression or distraction might be applied by the surgeon when preparing the disc space for an inter-body spacer, or inserting the spacer, or when compressing the vertebrae together using a surgical tool after the inter-body spacer is in place, and before locking the pedicle screw interconnecting rod.

Figure 17A:
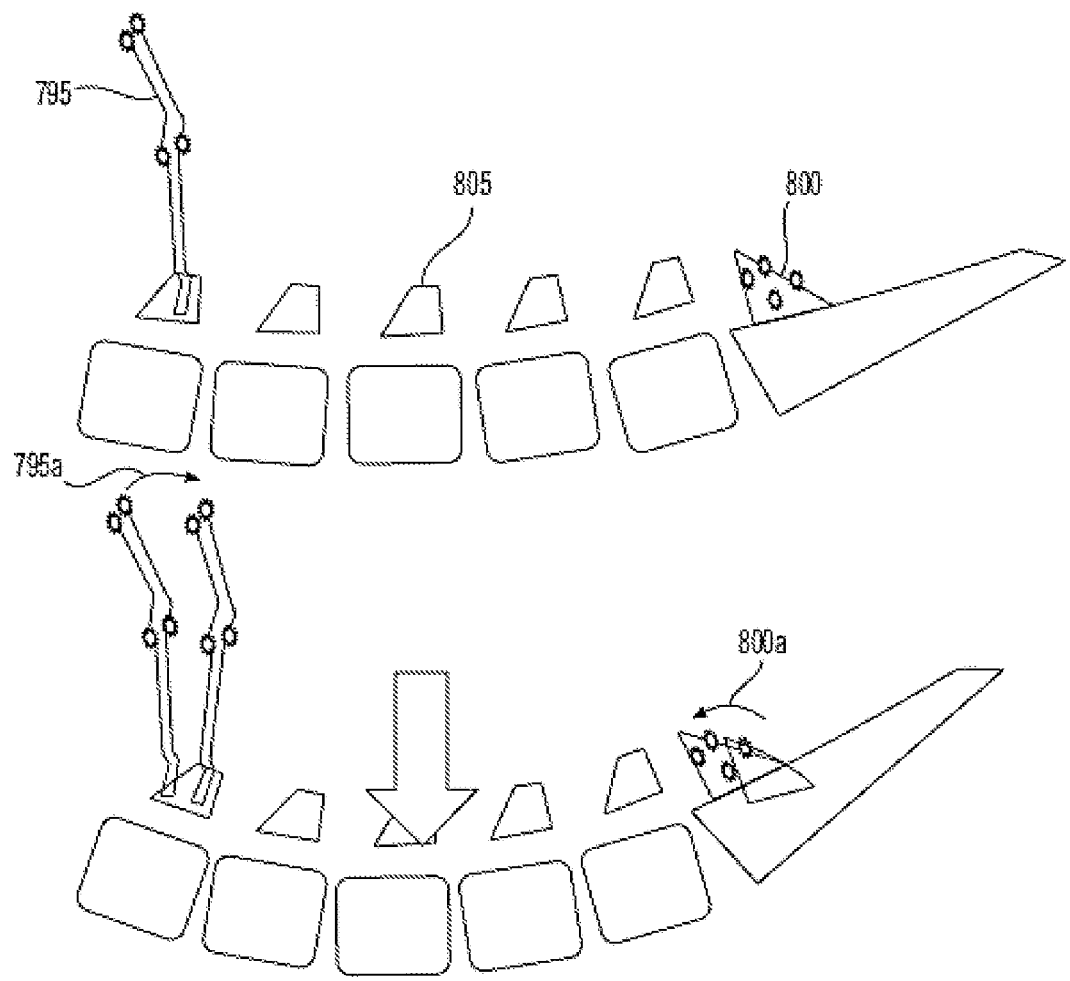
FIG. 17A shows an example illustration of one portion of a spine with markers in accordance with one embodiment of the invention.
Figure 17B:
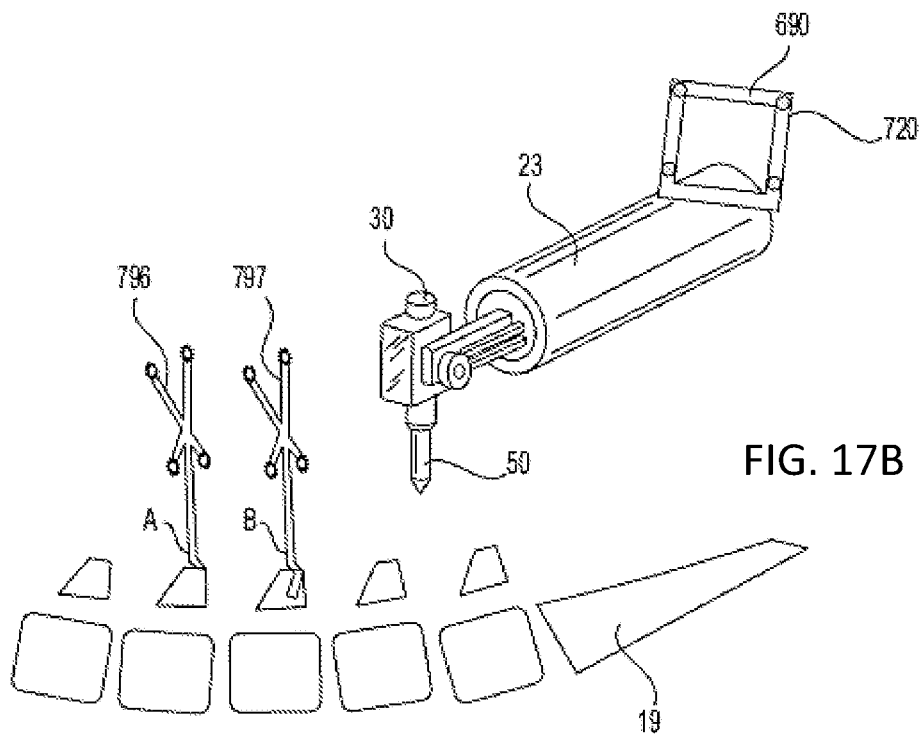
FIGS. 17B-17D show various illustrations of one portion of a spine with two independent trackers with markers in accordance with one embodiment of the invention.
Figure 17C:
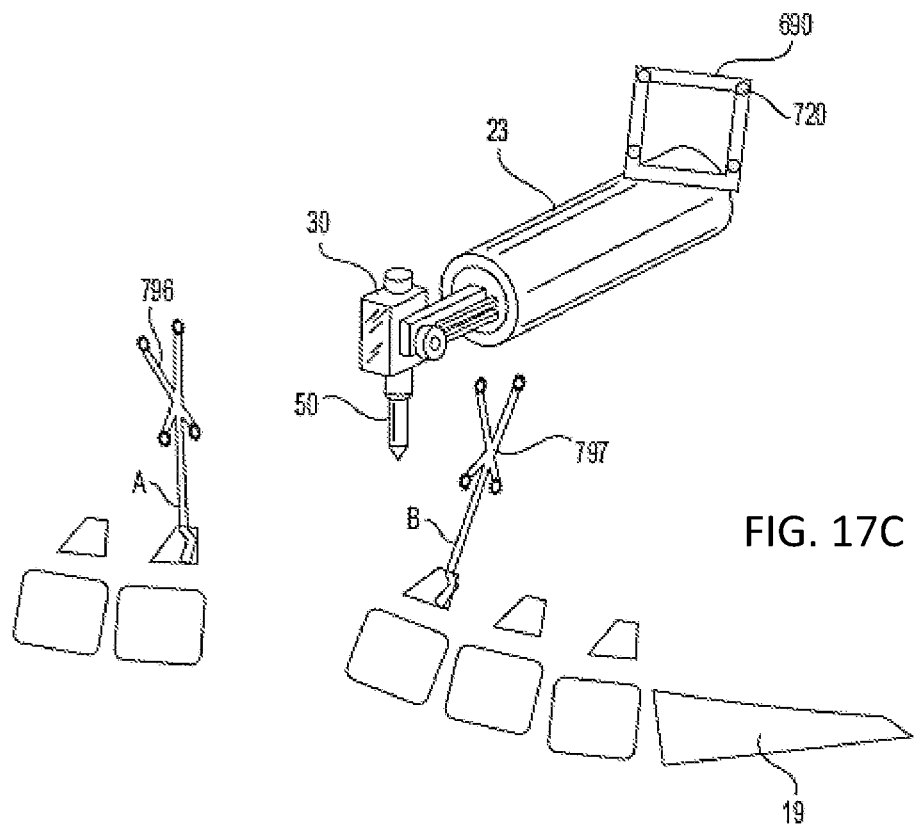
Figure 17D:
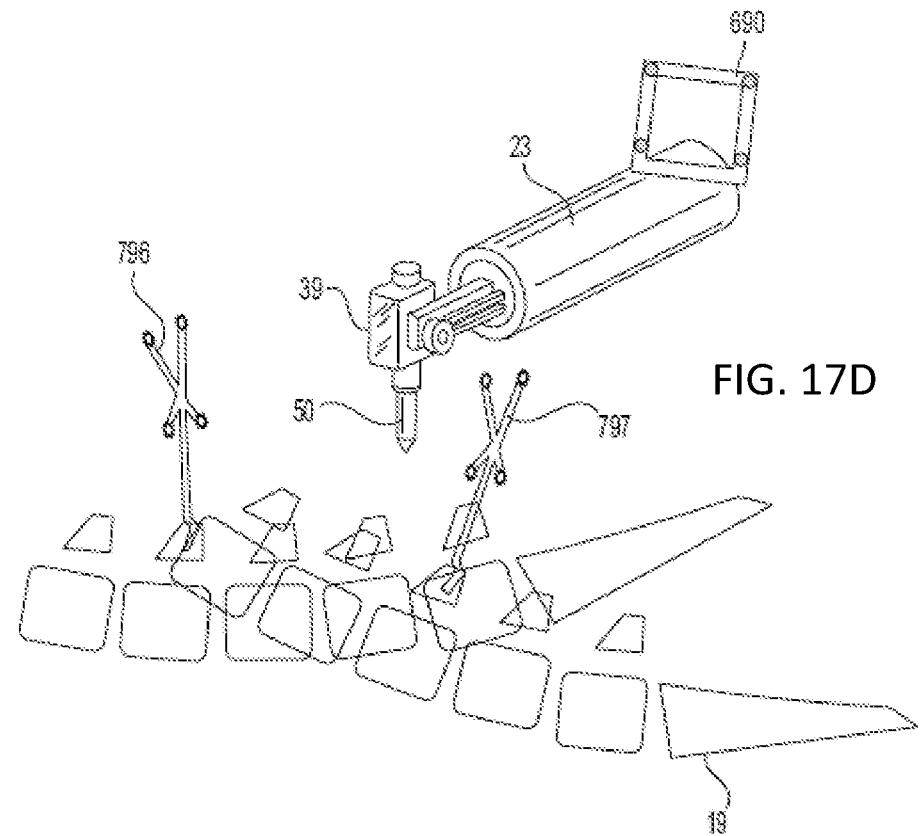
Figure 17E:
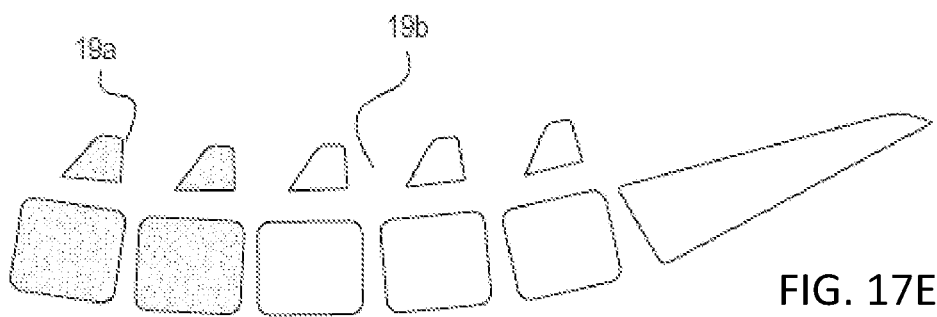
FIGS. 17E-17F illustrate a representation of a display of a portion of a spine based on the location of a tracker in accordance with one embodiment of the invention.
Figure 17F:
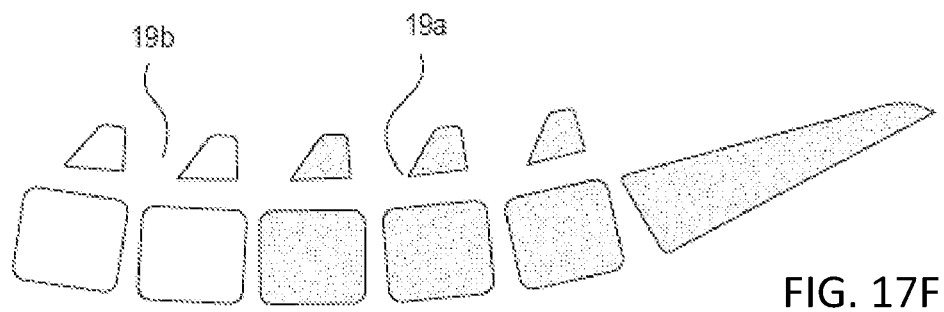
Figure 17G:
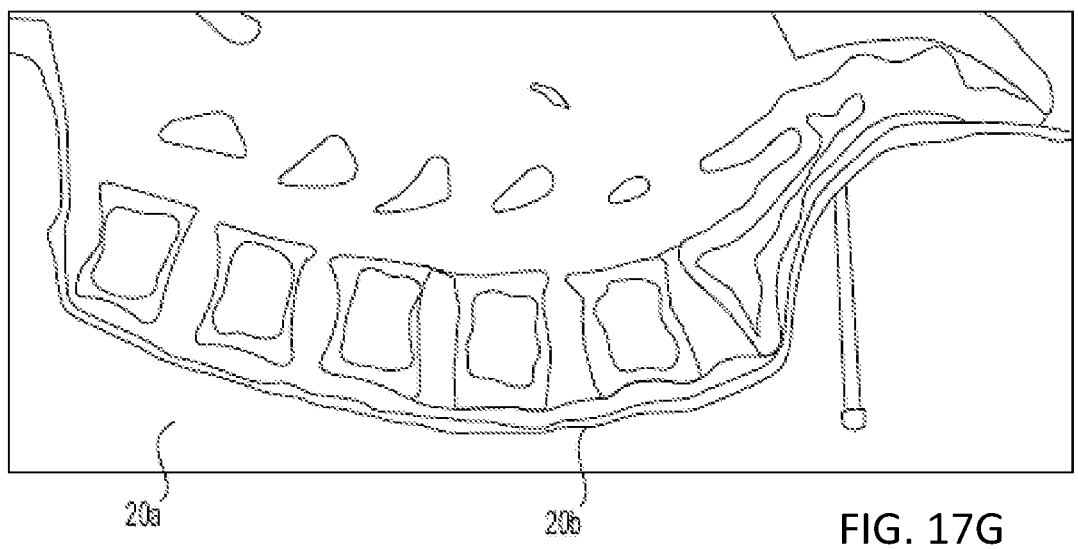
FIGS. 17G-17H represent images of segmented CT scans in accordance with one embodiment of the invention.
Figure 17H:
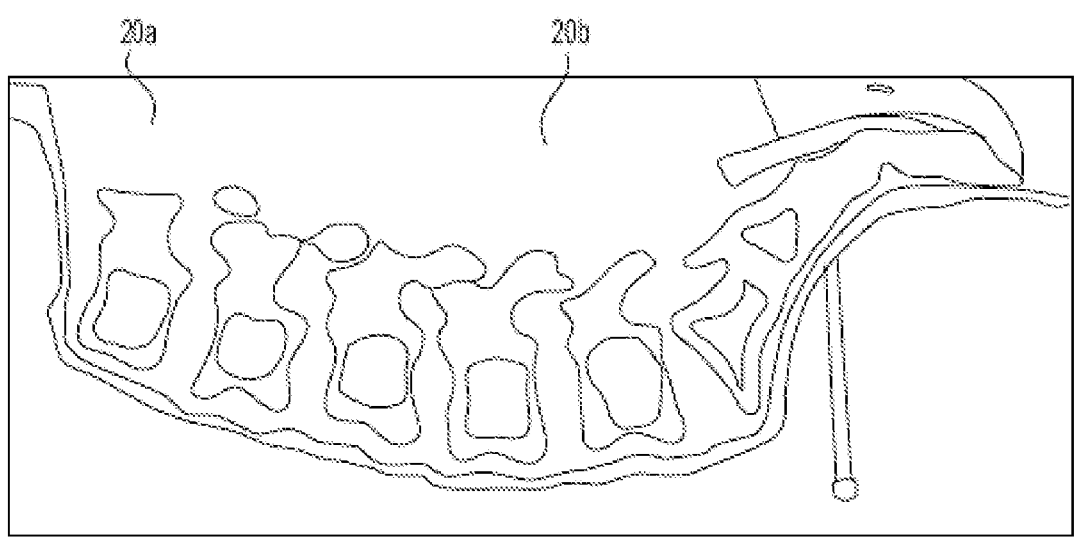

In some embodiments, if there is snaking of the spine, for example, when conventional screws are driven in place or the surgeon applies a focal force on one portion of the spine, the two marker trees will move (illustrated as 795a for tracker 795 and 800a for tracker 800) by different amounts and to different orientations (illustrated in FIG. 17A). The altered orientations and positions of the trackers 795, 800 can be used to calculate how the spine has snaked and adjust the perceived position of the robot 15 or probe to compensate. In some embodiments, because there are multiple degrees of freedom of the vertebrae, knowledge of how the two trackers' orientations shift does not allow a single unique solution. However, it can be assumed that the bending is symmetrical among all the vertebrae to calculate the new position, and even if this assumption is not perfect, it should provide a reasonably accurate solution. In some embodiments, experiments tracking how cadaveric spines respond to focal forces can be used to collect data that will help to predict how the two ends of the lumbar spine would respond during particular types of external loading.

Figure 18:
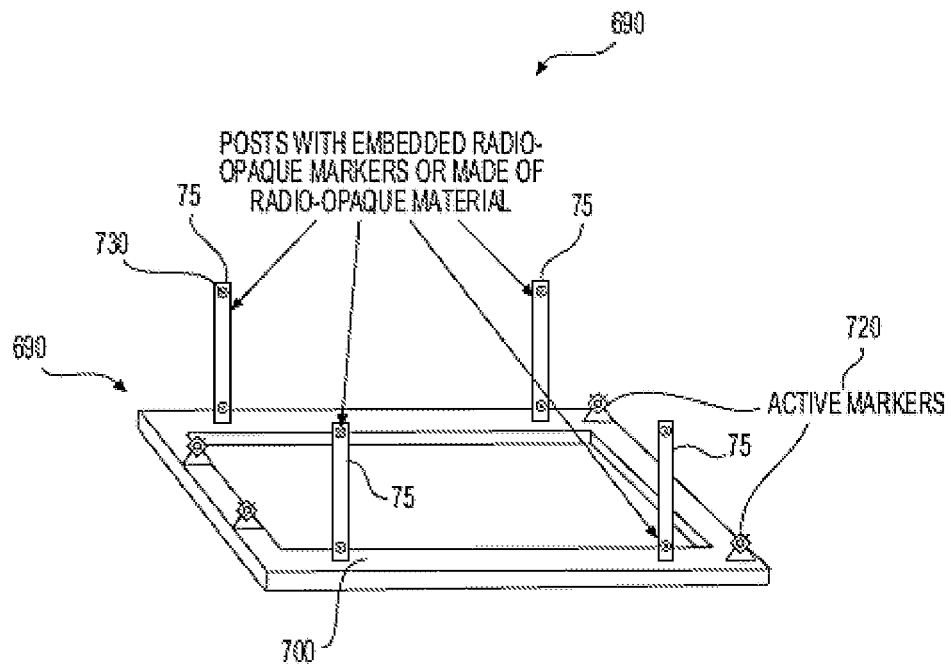
FIG. 18 shows an example of a fixture for use with fluoroscopic views in accordance with one embodiment of the invention.
Figures 19A, 19B:
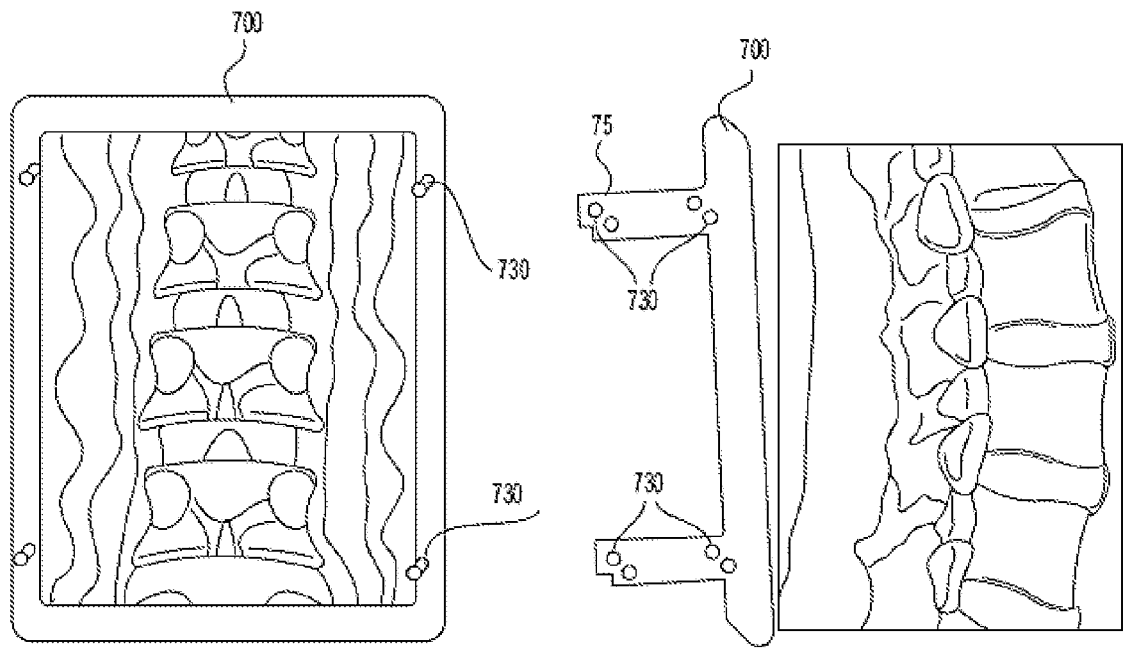
FIGS. 19A-19B illustrates expected images on anteroposterior and lateral x-rays of the spine with a misaligned fluoroscopy (x-ray) machine in accordance with one embodiment of the invention.

In some embodiments, it is possible to use the same surgical robot 15 already described for navigation with 3D imaging in a different setting where only 2 fluoroscopic views are obtained. In this instance, the surgical robot 15 will be able to accurately move to a desired position that is pre-planned on these two fluoroscopic views. Since the two fluoroscopic views can represent views to which the surgeon or radiologist is already accustomed, planning trajectories on these views should be straightforward. In obtaining the fluoroscopic views, a method is needed to establish the position of the coordinate system of the anatomy relative to the robot's 15 coordinate system. In some embodiments, a way to fulfill this registration is to obtain the fluoroscopic views while a targeting fixture 690 that includes features that are identifiable on the fluoroscopic images is attached to the patient 18. For example, FIG. 18 shows an example of a fixture for use with fluoroscopic views in accordance with one embodiment of the invention. In some embodiments, the targeting fixture 690 as shown can include features that will appear on 2 fluoroscopic views and active markers 720 for real-time tracking. This targeting fixture 690 has properties that will aid in the ability to set up the coordinate system of the anatomy from the two fluoroscopic images. For example, in some embodiments, the posts 75 as shown are symmetrically spaced around the frame 700 so that posts 75 and/or their embedded markers 730 would overlay on an x-ray image. That is, if there is no parallax, two posts 75 in an aligned position would appear as a single line segment instead of two, or two posts 75, each with two embedded radio-opaque markers 730, would appear as two dots instead of four dots on an x-ray image. These features allow and facilitate the patient 18 or fluoroscopy machine's position to be adjusted until such overlapping is achieved. Similarly, from top or bottom view, the posts 75 and/or their embedded markers 730 would overlap, with a single post appearing as a dot instead of a line segment or two embedded markers 730 in one post appearing as one dot instead of two once the fluoroscopy machine and patient 18 are adjusted to be aligned as desired. In some embodiments, the posts 75 may be designed to be temporarily inserted (i.e., they are present during the scan but are later unplugged from the frame during the procedure so they are not in the way of the user). In some embodiments, the active markers 720 are necessary for later tracking but do not necessarily need to be present during the scan as long as they can be attached with precision to a known position on the frame 700 relative to the radio-opaque makers 730. For example, in some embodiments, conventional sockets on the fixture 690 could later allow the active markers 720 to be snapped in to a location dictated by the manufacturing of the frame 700 or calibrated using a digitizing probe. Furthermore, note that the goal is not necessarily to get perfect lateral and anteroposterior anatomical views of the spine or other anatomy. The goal is to get alignment of the fixture 700 on the x-ray view. Although it may be beneficial in understanding what it being visualized to also achieve alignment with the anatomical planes, it is unnecessary for registration. An example of how the targeting fixture 690 might appear on anteroposterior or "A-P" and lateral x-rays when affixed to the patient's back but not yet aligned with the x-ray projection is shown in FIGS. 19A-19B.

Figure 20A:
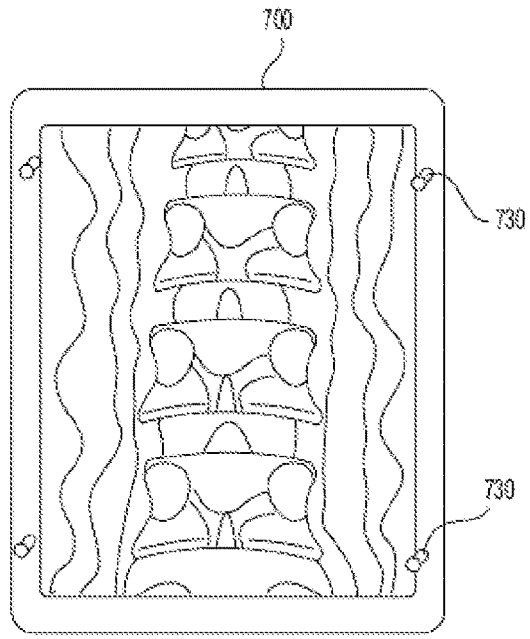
FIGS. 20A-20B illustrates expected images on anteroposterior and lateral x-rays of the spine with a well aligned fluoroscopy (x-ray) machine in accordance with one embodiment of the invention.
Figure 20B:
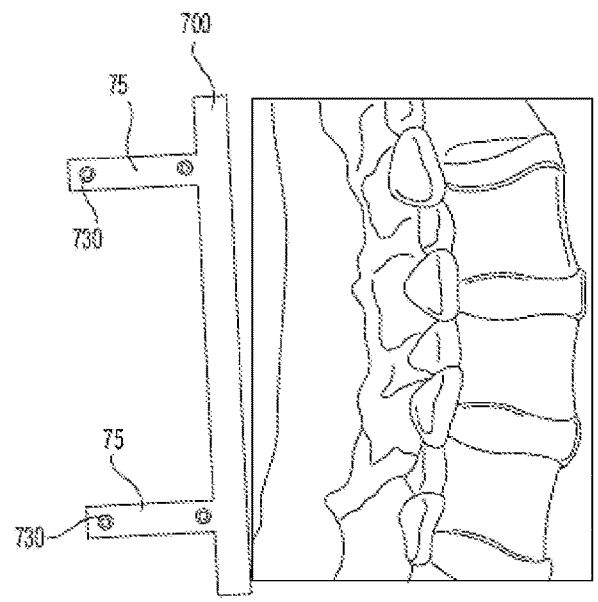

In some embodiments, after adjusting the position of the patient 18 and fluoroscopy unit, an overlay with good certainty may be obtained for images with radio-opaque markers 730. FIGS. 20A-20B for example illustrates expected images on anteroposterior and lateral x-rays of the spine with a well aligned fluoroscopy (x-ray) machine in accordance with one embodiment of the invention. As shown, the fluoroscopic images do not need the frame 700 to be positioned exactly aligned with the anatomy or rotated to be vertical and horizontal. In some embodiments, the fluoroscopically obtained images are not required to have the correct aspect ratio such that the image properly represents a calibrated coordinate system. In some embodiments, it is possible to rescale the image to adjust the aspect ratio using known distances between posts 75 or between markers 730, x-ray visible lengths of posts 75, or assuming the image should be perfectly circular or square. These distances are known in advance of obtaining the images by the manufacturing process, or by calibration using a digitizing probe or other means. In some embodiments, provided parallax is considered, the ratio of known inter-marker distances can be compared to the ratio of inter-marker distances measured on planar images and used to scale the planar image to achieve the correct aspect ratio. In some embodiments, it is not necessary to rescale the image, but it may help the user to better visualize the image and anatomy when it is displayed in the appropriate aspect ratio. In some embodiments, the comparison can also be used to determine the number of pixels per mm on the image for use in determining relative position of radio-opaque markers 730 and planned trajectory tip and tail. In some embodiments, rescaling facilitates equations for mapping between 2D and 3D space because the pixels per mm in the x and y direction are the same value.

In some embodiments, after obtaining two images, the two images can be used to construct a 3D Cartesian coordinate system because they represent images of the same thing (the fixture) from two orthogonal views. For example, the A-P image could be used to represent the X-Z plane, and the lateral image could be used to represent the Y-Z plane. Radio-opaque markers 730 on the A-P image have known x-axis and z-axis coordinates (as recorded from the manufacturing process or by calibration using a digitizing probe or other means), and the same radio-opaque markers 730 have known y-axis and z-axis coordinates on the lateral image. Therefore, in some embodiments, the x-axis, y-axis, and z-axis coordinates of the markers 730 can be found on the two images, and the positions of the anatomy and planned trajectories relative to these reference points can be related to these reference positions. In some embodiments, the mapping of a point from 3D space to the 2D image and vice versa can be performed knowing the constant mm per pixel, C, on coronal or sagittal images, and multiplying or dividing points by these constants if the center of the image and coordinate system have been shifted to overlap.

Figure 21A:
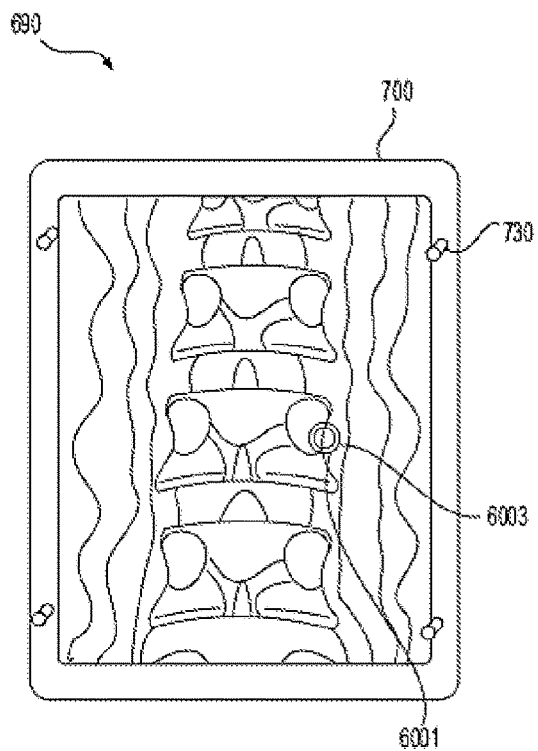
FIGS. 21A-21B illustrates expected images on anteroposterior and lateral x-rays of the spine with a well aligned fluoroscopy (x-ray) machine including overlaid computer-generated graphical images showing the planned trajectory and the current actual position of the robot end-effectuator in accordance with one embodiment of the invention.
Figure 21B:
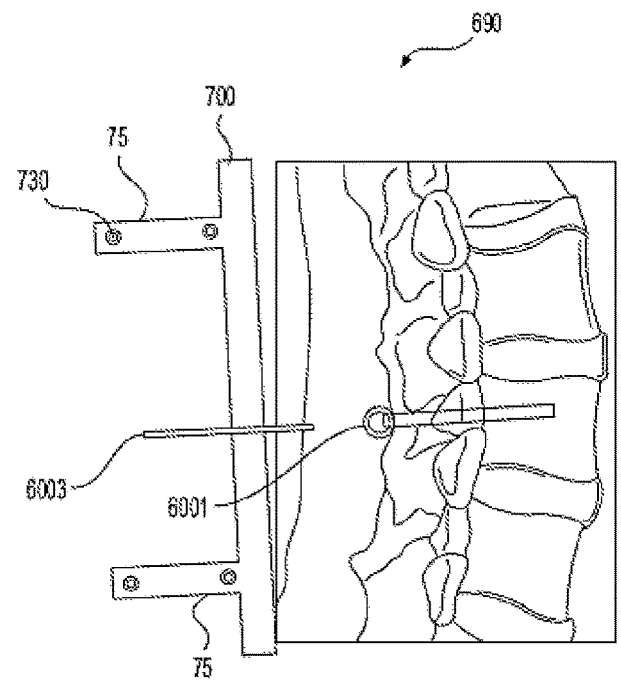

FIGS. 21A-21B illustrates expected images on anteroposterior and lateral x-rays of the spine with a well aligned fluoroscopy (x-ray) machine in accordance with one embodiment of the invention. As shown, FIGS. 21A-21B include overlaid computer-generated graphical images showing the planned trajectory (red 6001) and the current actual position of the robot 15 end-effectuator 30 (light blue 6003). The red circle in 6001 is provided for the user to identify the tail of the planned trajectory (as opposed to the tip). In other embodiments, the line segment could have different colored ends or different shapes on each end (pointed vs. blunt) for distinguishing tip from tail.

In some embodiments, assuming the A-P x-ray represents the X-Z plane and the lateral x-ray represents the Y-Z plane, the algorithm for planning a trajectory and relating this planned trajectory to the robot 15 coordinate system can include the following steps; 1). Draw a line on the A-P and lateral x-ray views representing where the desired trajectory should be positioned (see for example FIGS. 21A-21B). In some embodiments, the next step can include; 2). from the A-P view, find the X and Z coordinates of the reference opaque markers and of the tip and tail of the desired trajectory, and 3). from the lateral view, find the Y and Z coordinates of the reference opaque markers and of the tip and tail of the desired trajectory, and 4). based on the known coordinates of the active markers relative to the opaque markers, transform the X,Y,Z coordinates of the tip/tail into the coordinate system of the active markers. In some embodiments, the method can include store the locations of tip and tail in this coordinate system in computer 100 memory for later retrieval. In some embodiments, the next steps of the method can include; 5). at any frame in real time, retrieve the active marker 720 locations in the coordinate system of the cameras 8200, and 6). based on the stored coordinates of the tip and tail relative to the active markers 720 and the current location of the active markers 720 in the coordinate system of the cameras 8200, calculate the current location of the desired tip and tail in the coordinate system of the cameras 8200. In some embodiments, the next steps of the method can include; 7). transform the active marker 720 locations and the trajectory tip/tail locations into the coordinate system of the robot 15 using methods described before in which markers on the robot 15 are utilized as references, and 8). send the robot 15 to the desired tip/tail locations using methods described previously.

In some embodiments, while the robot 15 moves to position itself in the desired orientation and position, it is possible to overlay a graphical representation of the current location of the robot 15 on the fluoroscopic images by a method that can include; 1). retrieve current location of the robot 15 guide tube 50 in the coordinate system of the cameras 8200 based on active markers 720 attached to the robot, and 2). transform the guide tip and tail to the coordinate system of the medical images based on the locations of active markers on the targeting fixture 690, and 3). represent the current positions of tip/tail of the guide tube 50 on the A-P image by a line segment (or other suitable graphical representation) connecting the X,Z coordinates of the tip to the X,Z coordinates of the tail (see for example FIGS. 21A-21B), and 4). represent the current positions of tip/tail of the guide tube 50 on the lateral image by a line segment (or other suitable graphical representation) connecting the Y,Z coordinates of the tip to the Y,Z coordinates of the tail.

In some embodiments, in constructing the Cartesian coordinate system based on the two images, it is important to consider directionality. That is, in some embodiments, an x-ray image of the X-Z plane could show positive X to the right and negative X to the left or vice versa. In some embodiments, it could show positive Z upward and negative Z downward or vice versa. In some embodiments, an x-ray image of the Y-Z plane could show positive Y to the right and negative Y to the left or vice versa. In some embodiments, it could show positive Z upward and negative Z downward or vice versa. In some embodiments, if an incorrect assumption is made about the directionality of one of the axes, it would mean that the constructed 3D coordinate system has one or more of its axes pointing in the wrong direction. In some embodiments, this may send the robot 15 to an incorrect position. In some embodiments, one way of ensuring the correct directionality is to query to the user requesting verification of directionality on the images and/or allowing them to flip (mirror) the images on the display 29.

In some embodiments, another way of ensuring the correct directionality is to design the targeting fixture 690 so that the radio-opaque markers 730 are spaced asymmetrically. In some other embodiments, another way of ensuring the correct directionality is to design the targeting fixture 690 with additional radio-opaque features that unambiguously identify top, bottom, left, right, front and rear on images. For example, FIGS. 22A-22B illustrates expected images on anteroposterior and lateral x-rays of the spine with a well aligned fluoroscopy (x-ray) machine. As shown, the targeting fixture 690 illustrated in FIGS. 22A-22B includes a feature 755 designed to substantially eliminate ambiguity about directionality in accordance with one embodiment of the invention. As shown, the feature 755 could reveal a "L", "T", or other symbol on the x-ray when the view is correct so as to substantially eliminate directional ambiguity. Furthermore, the "T" feature could be drawn in script (e.g., 9) or other asymmetric letter or symbol used so that if an inverted or mirrored x-ray image is presented, the inverted nature is clear and can be compensated.

In some embodiments, the algorithm described here provides the user with two perpendicular x-ray views from which to plan a trajectory, and provides a visual feedback of the current location of a probe. Typically, these two views might be lateral and anteroposterior (A-P) views. In some embodiments, it might also be desirable for the user to see a third plane (for example, an axial plane). Based on knowledge of the anatomy and landmarks visible on the x-rays, in some embodiments, it is possible to create a rough "cartoon" showing an axial view. In some embodiments, the cartoon may help the user understand the approximate current location of the robot 15 or probe. FIG. 23 shows how such a cartoon can be generated from the x-rays. Note that the cartoon will be imperfect with respect to details such as the curvature of the vertebral body, but key landmarks such as the pedicle boundaries should be reasonably well defined. Such an approach would be based on how a typical vertebra is shaped. For example, FIG. 23 illustrates an axial view of a spine showing how a cartoonish axial approximation of the spine 5601 can be constructed based on a lateral x-ray 5602 and an anteroposterior x-ray 5603 in accordance with one embodiment of the invention. As shown, locations where key landmarks on the adjacent x-ray views intersect the cartoon can be identified with horizontal or vertical lines overlapping the cartoon and x-rays. The user positions these lines using a software interface or software automatically recognizes these features on the x-rays so that the lines intersect the key landmarks, such as a line just tangent to the vertebral body left border 5604, vertebral body right border 5605, vertebral body anterior wall 5606, vertebral body posterior wall 5607, posterior spinal canal 5608, left inner pedicle border 5609, left outer pedicle border 5610, tip of spinous process 5611, etc. After using the software to move these lines so that they intersect correct locations on the x-rays, the software can then stretch and morph the cartoon as needed to fit these anatomical limits. A view on the computer display of the axial plane showing this cartoon and the planned trajectory and current position of robot or probe can be generated by the software to provide additional visual feedback for the user.

Figure 24A:
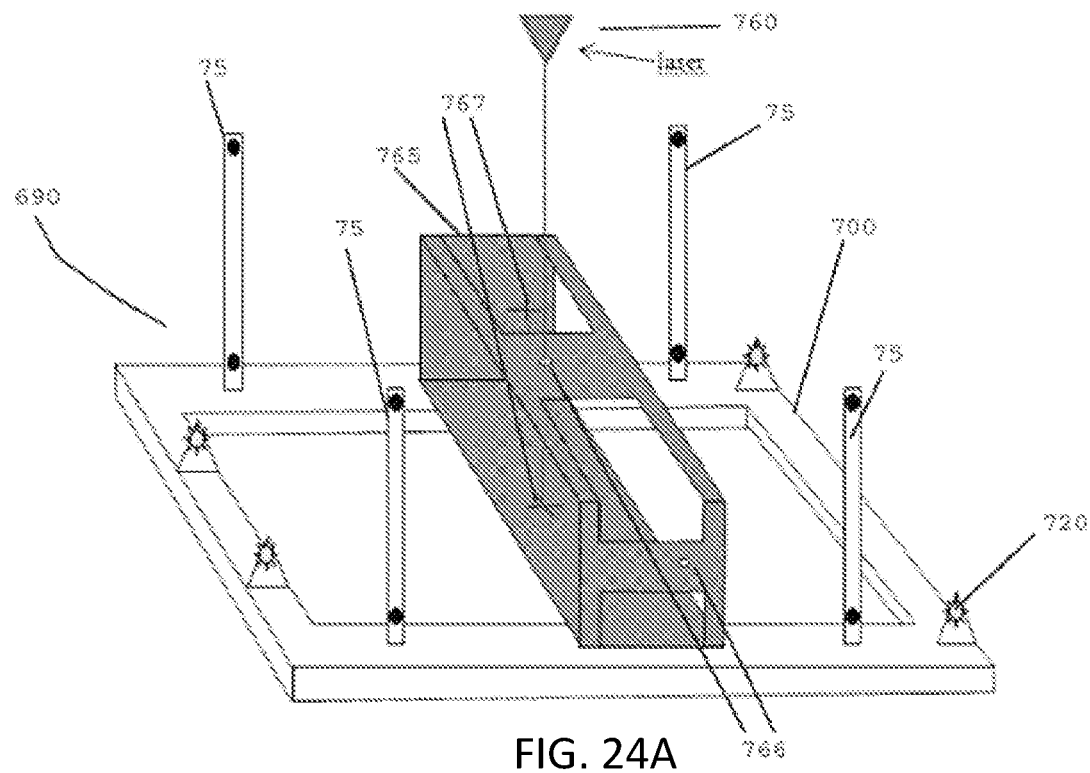
FIGS. 24A-24B illustrates examples of targeting fixtures that facilitate desired alignment of the targeting fixture relative to the x-ray image plane in accordance with one embodiment of the invention.
Figure 24B:
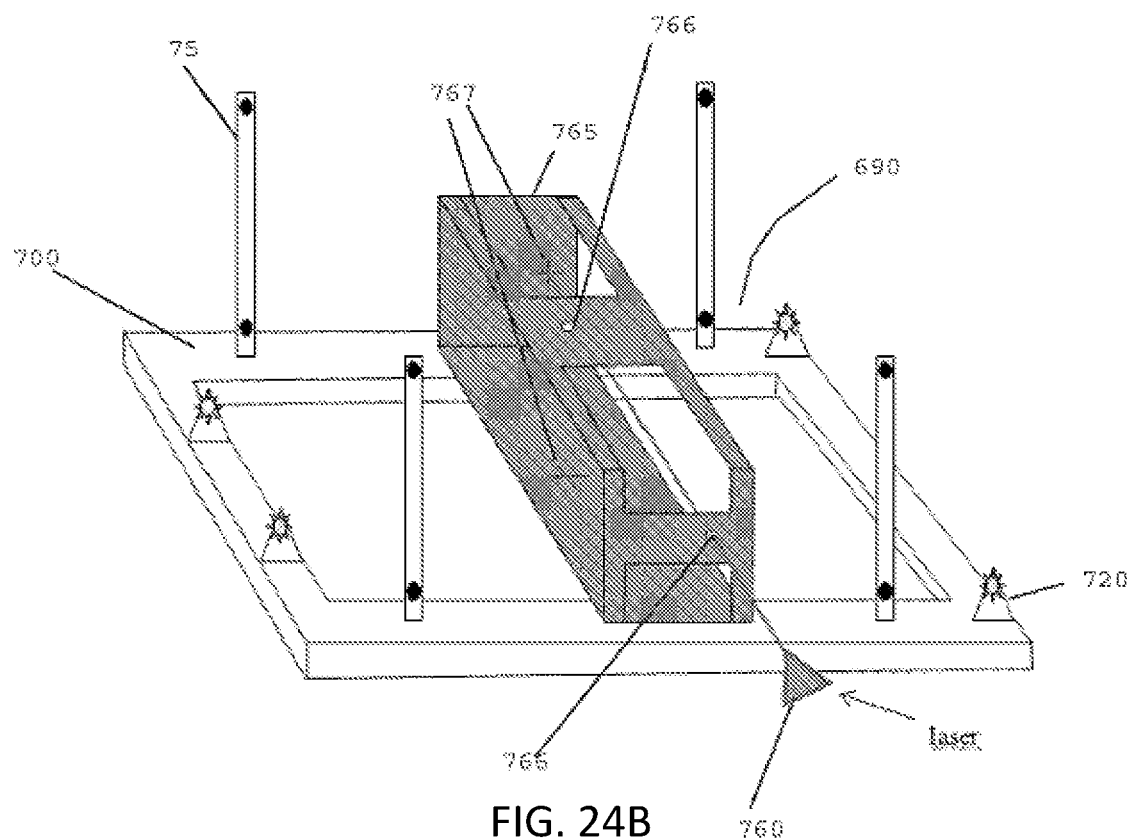

In some embodiments, in order to achieve well aligned x-rays like those shown in FIGS. 20A-20B, one possible method is trial and error. For example, the user can try to get the x-ray machine aligned to the targeting fixture 690, attempt to assess alignment by eye, then shoot an x-ray and see how it looks. In some embodiments, if dots are misaligned (for example as shown in FIGS. 19A-19B), adjustments would be made and a new x-ray image can be prepared. This method can be effective but can be dependent on the skill of the operator in assessing alignment and making corrections, and therefore can result in x-ray exposure to the patient 18 and staff. In some embodiments, it is possible to create a tool to assist in the alignment of the targeting fixture 690. In some embodiments, the tool could be a conventional laser that can be attached to the emitter or collector panel of the x-ray machine, capable of passing a laser beam parallel to the direction that the x-rays will travel. In some embodiments, the laser could be attached temporarily (using a conventional magnet or adhesive) or permanently, connected to an arm extending from the x-ray machine and oriented in the correct direction, enabling the directed beam to shine down toward the fixture 690. In some embodiments, if the fixture 690 has a geometric, electronic, or other features capable of visual or other feedback to the user regarding the vector direction of this laser light, it would allow alignment of the x-ray arm without taking any x-rays. An example of such a feature is shown in FIG. 24A and FIG. 24B. FIGS. 24A-24B illustrates examples of targeting fixtures 690 that facilitate desired alignment of the targeting fixture 690 relative to the x-ray image plane in accordance with one embodiment of the invention. As shown, some embodiments include a feature 765 temporarily added to the targeting fixture 690 In some embodiments, feature 765 facilitates desired alignment of the targeting fixture 690 relative to the x-ray image plane from an AP view when a laser (attached to the face of the x-ray emitter or collector) is directed through the opening 766 and toward the crosshairs 767 at the base. In some embodiments, if the laser light does not strike the crosshairs 767 dead center, further adjustment of the x-ray unit's orientation is needed. The temporarily added feature 765 that facilitates desired alignment of the targeting fixture 690 relative to the x-ray image plane from a lateral view when a laser (attached to the face of the x-ray emitter or collector) is directed through the opening and toward the crosshairs at the opposite face. In some embodiments, if the laser light does not strike the crosshairs dead center, further adjustment of the x-ray unit's orientation is needed.

In some embodiments, this method for aligning the radio-opaque markers 730 would have the advantage over trial-and-error methods that are affected by parallax effects, and as described below, do not confound the ability to align markers as needed. For example, with parallax, it may not be clear to the user when good alignment of the markers 730 is achieved, depending on how symmetrically spaced the markers 730 are about the center of the image.

With parallax error, the x-rays may not pass through the subject in a straight line and instead travel from emitter to receiver in a conical pattern. This conical path can produce an image where the details of anatomy on the 2D x-ray that are closer to the emitter of the x-rays will appear farther apart laterally than details of the anatomy that are closer to the receiver plate. In the case of x-ray images in FIGS. 20A-20B, instead of the radio-opaque markers 730 appearing overlaid, they may appear as shown in FIGS. 25A-25B. For example, FIGS. 25A-25B illustrates expected images on anteroposterior and lateral x-rays of the spine with a well aligned fluoroscopy (x-ray) machine when parallax is present in accordance with one embodiment of the invention. As shown, parallax affects spacing symmetrically about the x,y center of the image, with locations of markers 730 closer to the receiver plate of the x-ray unit appearing closer to the center of the image.

Further, in the description, two terms used are "near plane" and "far plane"—these terms refer to markers in the 2D views that appear farther apart or closer together because of parallax. The reason markers are farther apart or closer together is because of their proximity to the emitter or collector of the x-ray machine, with markers nearer the emitter appearing farther apart and markers nearer the collector closer together. However, rather than referencing distance from emitter and collector, "near plane" refers to markers that appear magnified (nearer to the eye) and "far plane" refers to markers that appear more distant.

Parallax will affect the image symmetrically about the center of the image. For example, in some embodiments, two markers 730 (one in near plane and one in far plane) that are in the same projected position, and are at the center of the image, may appear to be exactly on top of each other, whereas markers 730 in the near plane and far plane that are in the same projected position, but are close to the edge of the image may appear separated by a substantial distance.

FIG. 26A illustrates two parallel plates with identically positioned radio-opaque markers 730 in accordance with one embodiment of the invention. As shown, this illustrates possible marker 730 separation on an x-ray from markers 730 on two plates that are in the same projected line of sight. FIG. 26B illustrates resulting expected x-ray demonstrating how marker overlay is affected due to parallax using the two parallel plates as shown in FIG. 26A in accordance with one embodiment of the invention. By comparing the two parallel plates with identically positioned radio-opaque markers 730 shown in FIG. 26A, with the resulting expected x-ray in FIG. 26B demonstrates how marker overlay is affected due to parallax. In some embodiments, an algorithm can be implemented to account for this parallax effect. By doing so, the graphical image indicating the position of the probe or robot 15 can be adjusted to more accurately account for the perceived shift caused by parallax.

Figure 27:
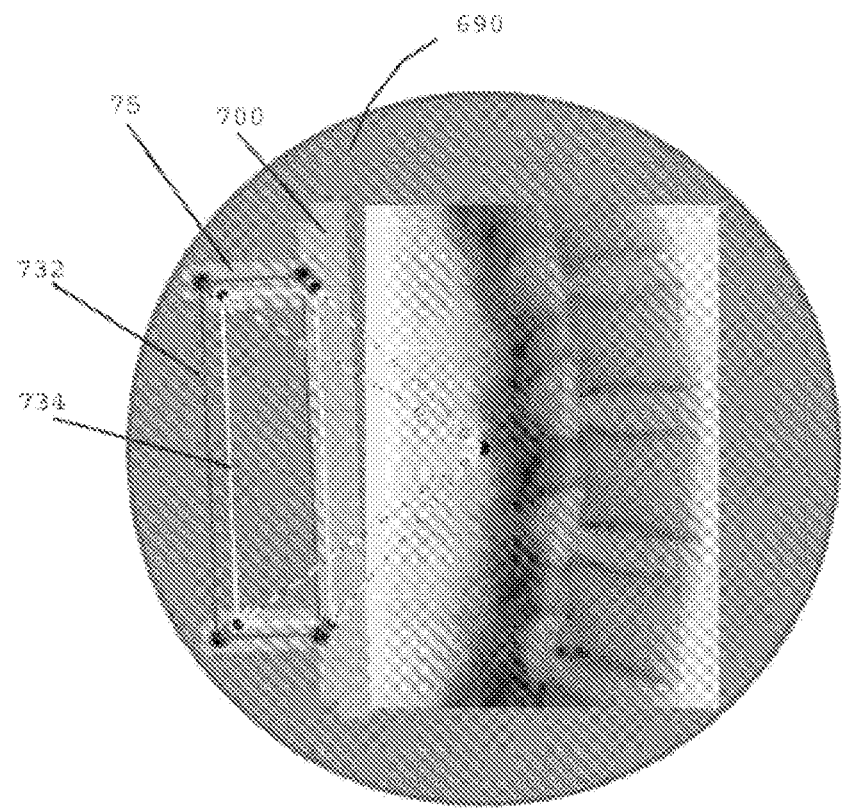
FIG. 27 shows a representation of the rendering of a computer screen with an x-ray image that is affected by parallax overlaid by graphical markers over the radio-opaque markers on two plates that have the same geometry in accordance with one embodiment of the invention.

In some embodiments, the algorithm requires information to be gathered on the near and far plane positions of the markers 730 on the image. That is, the user can indicate, using software or an automatic scan of the image, the spacing between markers 730, as shown in FIG. 27, which shows a representation of the rendering of a computer screen with an x-ray image that is affected by parallax overlaid by graphical markers 732, 734 over the radio-opaque markers 730 on two plates that have the same geometry in accordance with one embodiment of the invention. In some embodiments, the spacing between near plane and far plane markers 730 is known because of earlier calibration of the plates 700 in which the markers 730 are embedded, and the horizontal and vertical positions of the markers 730 are detectable relative to the center of the image. Therefore, in some embodiments, the parallax shift of the markers 730 can be calculated and applied to the mapping of any calculated three dimensional points on to the two dimensional image, and application of any necessary positional shift. For example, in some embodiments, it might be of interest to display a line segment on the two dimensional image representing how the shaft of a probe or robot 15 guide tube 50 (that is being tracked using optical tracking) would appear following x-ray imaging. In some embodiments, the x-axis, y-axis, and z-axis location of each end of the line segment (which has been calculated from optical tracking data) can be shifted based on the known parallax. Further, in some embodiments, a new line segment can be displayed that better represents how this projected object should appear on the 2D x-ray image.

Figure 28:
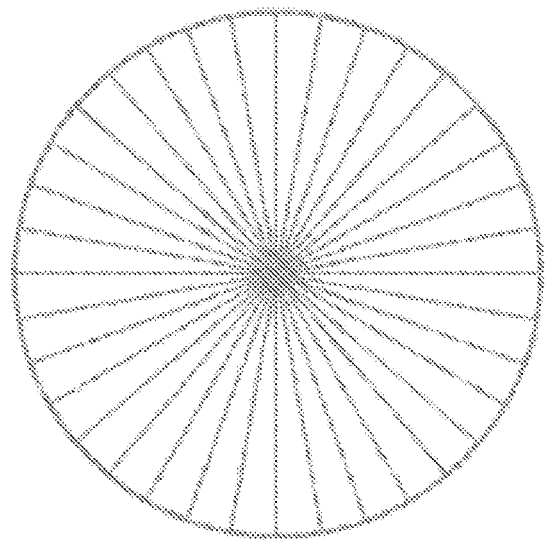
FIG. 28 shows a graphical overlay for the x-ray image screen intended to help the user physically line up the x-ray machine to get a view in which the markers on the two calibration plates shown in FIG. 26A in the case where parallax complicates the view in accordance with one embodiment of the invention.

In some embodiments, a method of implementing this system of two orthogonal fluoroscopy images to control a robot 15 can involve combining a robot 15 and fluoroscopy unit into a single interconnected device. There could be some advantages of this combination. For example, a conventional rotating turntable mechanism could be incorporated that could swing the fluoro arm into place, while at the same time swinging the robot arm 23 out of place (since the robot 15 would typically not be in the surgical field 17 at the same time as the fluoro arm). Furthermore, in some embodiments, the size of the robot arm 23 could be reduced compared to the stand-alone robot 15 because the fluoro arm's mass would serve as a counter-balance weight to help stabilize the robot arm 23. Moreover, in some embodiments, with integration, the fluoroscopy unit can more quickly transfer the image to the computer 100 and overlay with a graphical plot, for instance, as line segments starting at the center of the image and extending radially (similar to pie slices) around the image to facilitate appropriate marker 730 overlay. In some embodiments, overlaid near and far plane markers 730 should always fall on the same ray if the plates 690 with embedded markers 730 on the subject are aligned substantially parallel (see for example FIG. 28 which shows a graphical overlay for the x-ray image screen intended to help the user physically line up the x-ray machine). In some embodiments, the graphical overlay for the x-ray image screen can help the user physically line up the x-ray machine to avoid parallax. With parallax, any pair of corresponding markers on the 2 plates should lie on the same radial line, although the one in the far plane will lie closer to the middle of the image. In some embodiments, this overlay could be a physical object such as transparent film, or a computer-generated graphical image. In some embodiments, lines are spaced radially by 10 degrees, but actual spacing (frequency of lines) and regions in which lines are drawn could be user selectable.

Some embodiments can include mapping a 3D anatomical coordinate system on to two 2D orthogonal views (and vice versa) while considering parallax. For example, in some embodiments, a rigid frame is mounted to the patient and two perpendicular x-rays are taken to create a 3D coordinate system. To define this 3D coordinate system, a method is needed to map points from the 2D views (each with parallax) to the 3D volume and vice versa. The 3D coordinate system has coordinates x, y, z while the two 2D coordinate systems have coordinates $x_{AP}, z_{AP}$ and $x_{Lat}, z_{Lat}$ ("AP" for "anteroposterior" and "Lat" for "lateral" views).

In some embodiments, it can be assumed that the x-ray path from emitter to receiver is conical, and therefore linear interpolation/extrapolation can be used to adjust the positions of represented points. In some embodiments, software can calculate the distance of each landmark from the center of the image (indicated by dashed or dotted arrows). These distances, together with the known distance between near plane and far plane plates, can provide the necessary information to account for the parallax shift when mapping graphical objects whose positions are known in 3D back on to this 2D image.

Some embodiments can include solving to map x,y,z onto $x_{AP}, z_{AP}$ and $x_{Lat}, z_{Lat}$. For example, consider two intermediate 2D AP and lateral views represented as follows:

$$x_{ta}=(x-x_{oa})s_{AP}$$

$$z_{ta}=(z-z_{oa})s_{AP}$$

$$y_{tl}=(y-y_{ol})s_{Lat}$$

$$z_{tl}=(z-z_{ol})s_{Lat}$$

Where $x_{ta}$ and $z_{ta}$ can be called temporary scaled values of x and z in the AP plane, $y_{tl}$ and $z_{tl}$ are temporary scaled values of y and z in the Lat plane, $s_{AP}$ is the scaling factor in the AP plane, determined from the known near plane[1] marker spacing. $s_{Lat}$ is the scaling factor in the Lat plane, determined from the known near plane marker spacing of the lateral markers, and $x_{oa}, z_{oa}, y_{ol}$, and $z_{ol}$ are offsets in AP and Lat planes that position the markers such that they are as they appear centered about the image determined from registered positions of the markers on the images. In other words, $(x_{ta}, z_{ta})=(0,0)$ represents the center of the AP image and $(y_{tl}, z_{tl})=(0,0)$ represents the center of the lateral image. These planar values would be enough to display a 2D representation if no parallax were present or near plane markers were only being displayed.

In some embodiments, to find $x_{oa}, z_{oa}, y_{ol}$, and $z_{ol}$ consider pairs of points on the x-rays, because the ratio of distance from center on the x-ray is the same as the ratio of distance from center on the temporary scaled values. For example:

$$\frac{x_{AP1}}{x_{AP2}} = \frac{x_{ta1}}{x_{ta2}} = \frac{(x_1 - x_{oa})s_{AP}}{(x_2 - x_{oa})s_{AP}}$$

$$\left(\frac{x_{AP1}}{x_{AP2}}\right)(x_2 - x_{oa}) = x_1 - x_{oa}$$

$$x_2\left(\frac{x_{AP1}}{x_{AP2}}\right) - x_1 = x_{oa}\left(\frac{x_{AP1}}{x_{AP2}}\right) - x_{oa}$$

$$x_{oa}\left(\frac{x_{AP1}}{x_{AP2}} - 1\right) = x_2\left(\frac{x_{AP1}}{x_{AP2}}\right) - x_1$$

$$x_{oa} = \frac{x_2\left(\frac{x_{AP1}}{x_{AP2}}\right) - x_1}{\frac{x_{AP1}}{x_{AP2}} - 1}$$

In some embodiments, it can be seen from this equation that it is important to stay away from points where $x_{AP1} \approx x_{AP2}$ because it would result in a divide by zero error. Similar equations can be written for $z_{oa}$, $y_{ol}$, and $z_{ol}$ as follows:

$$z_{oa} = \frac{z_2\left(\frac{x_{AP1}}{x_{AP2}}\right) - z_1}{\frac{x_{AP1}}{x_{AP2}} - 1}$$

$$y_{ol} = \frac{y_2\left(\frac{x_{Lat1}}{x_{Lat2}}\right) - y_1}{\frac{y_{Lat1}}{y_{Lat2}} - 1}$$

$$z_{ol} = \frac{z_2\left(\frac{z_{Lat1}}{z_{Lat2}}\right) - z_1}{\frac{z_{Lat1}}{z_{Lat2}} - 1}$$

This mapping to temporary scaled values gets the near plane markers mapped correctly, but adjustment is needed to account for any position other than near plane as follows:

$$x_{AP} = x_{ta} k_a(y)$$

$$z_{AP} = z_{ta} k_a(y)$$

$$y_{Lat} = y_{tl} k_l(x)$$

$$z_{Lat} = z_{tl} k_l(x)$$

As specified, $k_a$ is a function of y and $k_l$ is a function of x. For $k_a$, this function is a linear interpolation function, in which if y is the y position of the near plane ($y_n$), then $k_a=1$ and if y is the y position of the far plane ($y_f$), then $k_a$ is the ratio of far plane spacing to near plane spacing, $r_a$. For $k_l$, this function is a linear interpolation function, in which if x is the x position of the near plane ($x_n$), then $k_l=1$ and if x is the x position of the far plane ($x_f$), then $k_l$ is the ratio of far plane spacing to near plane spacing, $r_l$. Note that $y_n, y_f, x_n,$ and $x_f$ are in a coordinate system with the origin at the center of the image.

$$k_a = 1 - \left(\frac{y_{tl} - y_n}{y_f - y_n}\right)(1 - r_a)$$

$$k_l = 1 - \left(\frac{x_{ta} - x_n}{y_f - y_n}\right)(1 - r_l)$$

Combining equations, $$x_{AP} = x_{ta}\left[1 - \left(\frac{y_{tl} - y_n}{y_f - y_n}\right)(1 - r_a)\right]$$

$$z_{AP} = z_{ta}\left[1 - \left(\frac{y_{tl} - y_n}{y_f - y_n}\right)(1 - r_a)\right]$$

$$y_{Lat} = y_{tl}\left[1 - \left(\frac{x_{ta} - x_n}{x_f - x_n}\right)(1 - r_l)\right]$$

$$z_{Lat} = z_{tl}\left[1 - \left(\frac{x_{ta} - x_n}{x_f - x_n}\right)(1 - r_l)\right]$$

It should also be possible to map $x_{AP}$, $z_{AP}$, $y_{Lat}$, and $z_{Lat}$ onto x,y,z. Having 4 equations and 4 unknowns:

$$x_{AP} = x_{ta}\left[1 - \left(\frac{y_{tl} - y_n}{y_f - y_n}\right)(1 - r_a)\right]$$

$$1 - \frac{x_{AP}}{x_{ta}} = \left(\frac{y_{tl} - y_n}{y_f - y_n}\right)(1 - r_a)$$

$$\left(1 - \frac{x_{AP}}{x_{ta}}\right)\left(\frac{y_f - y_n}{1 - r_a}\right) = y_{tl} - y_n$$

$$y_{tl} = \left(1 - \frac{x_{AP}}{x_{ta}}\right)\left(\frac{y_f - y_n}{1 - r_a}\right) + y_n$$

Then substitute into this equation:

$$y_{Lat} = y_{tl}\left[1 - \left(\frac{x_{ta} - x_n}{x_f - x_n}\right)(1 - r_l)\right]$$

$$y_{Lat} = \left[\left(1 - \frac{x_{AP}}{x_{ta}}\right)\left(\frac{y_f - y_n}{1 - r_a}\right) + y_n\right]\left[1 - \left(\frac{x_{ta} - x_n}{x_f - x_n}\right)(1 - r_l)\right]$$

And solve for $x_{ta}$:

$$y_{Lat} = \left[\left(\frac{y_f - y_n}{1 - r_a}\right) - \frac{x_{AP}}{x_{ta}}\left(\frac{y_f - y_n}{1 - r_a}\right) + y_n\right]\left[1 - \left(\frac{1 - r_l}{x_f - x_n}\right)(x_{ta} - x_n)\right]$$

$$y_{Lat} = \left[\left(\frac{y_f - y_n}{1 - r_a}\right) + y_n\right] - \left[\frac{x_{AP}}{x_{ta}}\left(\frac{y_f - y_n}{1 - r_a}\right)\right]\left[\left[1 + x_n\left(\frac{1 - r_l}{x_f - x_n}\right)\right] - \left[x_{ta}\left(\frac{1 - r_l}{x_f - x_n}\right)\right]\right]$$

-continued $$y_{Lat} = \left[A - \frac{B}{x_{ta}}\right][C - Dx_{ta}]$$

$$y_{Lat} = AC - \frac{BC}{x_{ta}} - ADx_{ta} + BD$$

$$AC + BD - y_{Lat} = \frac{BC}{x_{ta}} + ADx_{ta}$$

$$(AD)x_{ta}^2 + (y_{Lat} - AC - BD)x_{ta} + (BC) = 0$$

Quadratic Formula:

$$x = \frac{-b \pm \sqrt{b^2 - 4ac}}{2a}$$

$$x_{ta} = \frac{-(y_{Lat} - AC - BD) \pm \sqrt{(y_{Lat} - AC - BD)^2 - 4(AD)(BC)}}{2(AD)}$$

Where:

$$A = \left(\frac{y_f - y_n}{1 - r_a}\right) + y_n$$

$$B = x_{AP}\left(\frac{y_f - y_n}{1 - r_a}\right)$$

$$C = 1 + \left(\frac{1 - r_l}{x_f - x_n}\right)x_n$$

$$D = \frac{1 - r_l}{x_f - x_n}$$

Then plug into this equation to solve for $y_{tl}$:

$$y_{tl} = \left(1 - \frac{x_{AP}}{x_{ta}}\right)\left(\frac{y_f - y_n}{1 - r_a}\right) + y_n$$

Then plug into this equation to solve for $z_{tl}$:

$$z_{tl} = z_{Lat} \bigg/ \left[1 - \left(\frac{x_{ta} - x_n}{x_f - x_n}\right)(1 - r_l)\right]$$

Then plug into this equation to solve for $z_{ta}$:

$$z_{ta} = z_{AP} \bigg/ \left[1 - \left(\frac{y_{tl} - y_n}{y_f - y_n}\right)(1 - r_a)\right]$$

Solve differently to give another option for z:

$$y_{Lat} = y_{tl}\left[1 - \left(\frac{x_{ta} - x_n}{x_f - x_n}\right)(1 - r_l)\right]$$

$$\left(\frac{x_{ta} - x_n}{x_f - x_n}\right)(1 - r_l) = 1 - \frac{y_{Lat}}{y_{tl}}$$

$$(x_{ta} - x_n)\left(\frac{1 - r_l}{x_f - x_n}\right) = 1 - \frac{y_{Lat}}{y_{tl}}$$

$$x_{ta}\left(\frac{1 - r_l}{x_f - x_n}\right) - x_n\left(\frac{1 - r_l}{x_f - x_n}\right) = 1 - \frac{y_{Lat}}{y_{tl}}$$

-continued $$x_{ta}\left(\frac{1-r_l}{x_f - x_n}\right) = 1 - \frac{y_{Lat}}{y_{tl}} + x_n\left(\frac{1-r_l}{x_f - x_n}\right)$$

$$x_{ta} = \left(1 - \frac{y_{Lat}}{y_{tl}}\right)\left(\frac{x_f - x_n}{1 - r_l}\right) + x_n$$

Substitute into:

$$x_{AP} = x_{ta}\left[1 - \left(\frac{y_{tl} - y_n}{y_f - y_n}\right)(1 - r_a)\right]$$

$$x_{AP} = \left[\left(1 - \frac{y_{Lat}}{y_{tl}}\right)\left(\frac{x_f - x_n}{1 - r_l}\right) + x_n\right]\left[1 - \left(\frac{y_{tl} - y_n}{y_f - y_n}\right)(1 - r_a)\right]$$

And solve for $y_{tl}$:

$$x_{AP} = \left[\left(\frac{x_f - x_n}{1 - r_l}\right) - \frac{y_{Lat}}{y_{tl}}\left(\frac{x_f - x_n}{1 - r_l}\right) + x_n\right]\left[1 - (y_{tl} - y_n)\left(\frac{1 - r_a}{y_f - y_n}\right)\right]$$

$$x_{AP} = \left[\left[\left(\frac{x_f - x_n}{1 - r_l}\right) + x_n\right] - \left[\frac{y_{Lat}}{y_{tl}}\left(\frac{x_f - x_n}{1 - r_l}\right)\right]\right]$$

$$\left[\left[1 + y_n\left(\frac{1 - r_a}{y_f - y_n}\right)\right] - \left[y_{tl}\left(\frac{1 - r_a}{y_f - y_n}\right)\right]\right]$$

$$x_{AP} = \left[A - \frac{B}{y_{tl}}\right][C - D y_{tl}]$$

$$x_{AP} = AC - \frac{BC}{y_{tl}} - AD y_{tl} + BD$$

$$AC + BD - x_{AP} = \frac{BC}{y_{tl}} + AD y_{tl}$$

$$(AD)y_{tl}^2 + (x_{AP} - AC - BD)y_{tl} + (BC) = 0$$

Quadratic formula:

$$x = \frac{-b \pm \sqrt{b^2 - 4ac}}{2a}$$

$$y_{tl} = \frac{-(x_{AP} - AC - BD) \pm \sqrt{(x_{AP} - AC - BD)^2 - 4(AD)(BC)}}{2(AD)}$$

Where:

$$A = \left(\frac{x_f - x_n}{1 - r_l}\right) + x_n$$

$$B = y_{Lat}\left(\frac{x_f - x_n}{1 - r_l}\right)$$

$$C = 1 + y_n\left(\frac{1 - r_a}{y_f - y_n}\right)$$

$$D = \frac{1 - r_a}{y_f - y_n}$$

From these equations, it is possible to go from a known x,y,z coordinate to the perceived $x_{AP}, z_{AP}$ and $x_{Lat}, z_{Lat}$ coordinates on the two views, or to go from known $x_{AP}, z_{AP}$ and $x_{Lat}, z_{Lat}$ coordinates on the two views to an x,y,z coordinate in the 3D coordinate system. It is therefore possible to plan a trajectory on the $x_{AP}, z_{AP}$ and $x_{Lat}, z_{Lat}$ views and determine what the tip and tail of this trajectory are, and it is also possible to display on the $x_{AP}, z_{AP}$ and $x_{Lat}, z_{Lat}$ views the current location of the robot's end effectuator.

In some embodiments, additional measurement hardware (for example, conventional ultrasound, laser, optical tracking, or a physical extension like a tape measure) can be attached to the fluoro unit to measure distance to the attached plates, or other points on the anatomy to ensure that plates are parallel when fluoro images are obtained.

In some embodiments, the identity of the surgical instrument 35 can be used by the control system for the computing device or other controller for the surgical robot system 1. In some embodiments, the control system can automatically adjust axial insertion and/or forces and applied torques depending upon the identity of the surgical instrument 35.

In some embodiments, when performing atypical procedure for needle 7405, 7410 or probe insertion (for biopsy, facet injection, tumor ablation, deep brain stimulation, etc.) a targeting fixture 690 is first attached by the surgeon or technician to the patient 18. The targeting fixture 690 is either clamped to bone (open or percutaneously), adhered as a rigid object to the skin, or unrolled and adhered to the skin. In some embodiments, the roll 705 could have a disposable drape incorporated. If a flexible roll 705 is used, reflective markers 720 will then be snapped into place in some embodiments.

In some embodiments, once a targeting fixture 690 is attached, the patient 18 can receive an intraoperative 3D image (Iso-C, O-Arm, or intraoperative CT) with radio-opaque markers 730 included in the field of view along with the region of interest. In some embodiments, for best accuracy and resolution, a fine-slice image is preferred (CT slice spacing=1 mm or less). The 3D scan has to include the radio-opaque markers 730 and the anatomy of interest; not including both would disallow calibration to the robot 15.

In some embodiments, the 3D image series is transferred to (or acquired directly to) the computer 100 of the robot 15. The 3D image has to be calibrated to the robot's position in space using the locations on the 3D image of the radio-opaque markers 730 that are embedded in the targeting fixture 690. In some embodiments, this calibration can be done by the technician scrolling through image slices and marking them using the software, or by an algorithm that automatically checks each slice of the medical image, finds the markers 730, verifying that they are the markers 730 of interest based on their physical spacing (the algorithm is documented herein). In some embodiments, to ensure accuracy, limit subjectivity, and to speed up the process, image thresholding is used to help define the edges of the radio-opaque marker 730, and then to find the center of the marker 730 (the program is documented herein). Some embodiments of the software can do the necessary spatial transformations to determine the location in the room of the robot's markers relative to anatomy through standard rigid body calculations. For example, by knowing the locations of the radio-opaque markers 730 in the coordinate system of the medical image, and knowing the locations of the active markers 720 on the calibration frame 700 relative to these radio-opaque markers 730, and monitoring the locations of the active markers on the robot 15 and targeting fixture 690.

Some embodiments allow the surgeon to use the software to plan the trajectories for needles/probes 7405, 7410. In some embodiments, the software will allow any number of trajectories to be stored for use during the procedure, with each trajectory accompanied by a descriptor.

In some embodiments, the robot 15 is moved next to the procedure table and cameras 8200 for tracking robot 15 and patient 18 are activated. The cameras 8200 and robot 15 are positioned wherever is convenient for the surgeon to access the site of interest. The marker mounts on the robot 15 have adjustable positions to allow the markers 720 to face toward the cameras 8200 in each possible configuration. In some embodiments, a screen can be accessed to show where the robot 15 is located for the current Z-frame 72 position, relative to all the trajectories that are planned. In some embodiments, the use of this screen can confirm that the trajectories planned are within the range of the robot's reach. In some embodiments, repositioning of the robot 15 is performed at this time to a location that is within range of all trajectories. Alternately or additionally, in some embodiments, the surgeon can adjust the Z-frame 72 position, which will affect the range of trajectories that the robot 15 is capable of reaching (converging trajectories require less x-y reach the lower the robot 15 is in the z-axis 70). During this time, substantially simultaneously, a screen shows whether markers 720, 730 on the patient 18 and robot 15 are in view of the cameras 8200. Repositioning of the cameras 8200, if necessary, is also performed at this time for good visibility.

In some embodiments, the surgeon then selects the first planned trajectory and he/she (or assistant) presses "go". The robot 15 moves in the x-y (horizontal) plane and angulates roll 62 and pitch 60 until the end-effectuator 30 tube intersects the trajectory vector. In some embodiments, during the process of driving to this location, a small laser light will indicate end-effectuator 30 position by projecting a beam down the trajectory vector toward the patient 18. This laser simply snaps into the top of the end-effectuator 30 tube. In some embodiments, when the robot's end-effectuator 30 tube coincides with the trajectory vector to within the specified tolerance, auditory feedback is provided to indicate that the desired trajectory has been achieved and is being held. Alternately or additionally, in some embodiments, light of a meaningful color is projected on the surgical field 17. For example, in some embodiments, movement of the patient 18 or robot 15 is detected by optical markers 720 and the necessary x-axis 66, y-axis 68, roll 62, and pitch 60 axes are adjusted to maintain alignment.

In some embodiments, the surgeon then drives Z-frame 72 down until the tip of the end-effectuator 30 reaches the desired distance from the probe's or needle's target (typically the skin surface). While moving, the projected laser beam point should remain at a fixed location since movement is occurring along the trajectory vector. Once at the desired Z-frame 72 location, in some embodiments, the surgeon or other user can select an option to lock the Z-tube 50 position to remain at the fixed distance from the skin during breathing or other movement. At this point, the surgeon is ready to insert the probe or needle 7405, 7410. If the length of the guide tube 50 has been specified and a stop on the needle 7405, 7410 or probe is present to limit the guide tube 50 after some length has been passed, the ultimate location of the tip of the probe/needle 7405, 7410 can be calculated and displayed on the medical image in some embodiments. As described earlier, Additionally, in some embodiments, it is possible to incorporate a mechanism at the entry of the guide tube 50 that is comprised of a spring-loaded plunger 54 with a through-hole, and measures electronically the depth of depression of the plunger 54, corresponding to the amount by which the probe or needle 7405, 7410 currently protrudes from the tip of the guide tube 50.

In some embodiments, at any time during the procedure, if there is an emergency and the robot 15 is in the way of the surgeon, the "E-stop" button can be pressed on the robot 15, at which point all axes except the Z-frame axis 72 become free-floating and the robot's end-effectuator 30 can be manually removed from the field by pushing against the end-effectuator 30.

Some embodiments can include a bone screw or hardware procedure. For example, during a typical procedure for conventional screw or hardware insertion in the spine, the patient 18 is positioned prone (or other position) on the procedure table, and is supported. In some embodiments, a targeting fixture 690 is attached to the patient's spine by the surgeon or technician. In some embodiments, the targeting fixture 690 is either clamped to bone (open or percutaneously) or unrolled and adhered to the skin (for example using roll 705). The roll 705 could have a disposable drape incorporated. If a flexible roll 705 is used, reflective markers 720 will then be snapped into place in some embodiments.

In some embodiments, once a targeting fixture 690 is attached, the patient 18 can undergo an intraoperative 3D image (Iso-C, O-Arm, or intraoperative CT) with radio-opaque markers 730 included in the field of view along with the bony region of interest. In some embodiments, for best accuracy and resolution, a fine-slice image is preferred (where the CT slice spacing=1 mm or less). The 3D scan in some embodiments has to include the radio-opaque markers 730 and the bony anatomy; not including both would disallow calibration to the robot 15.

In some embodiments, the 3D image series is transferred to (or acquired directly to) the computer 100 of the robot 15, and the 3D image is calibrated in the same way as described above for needle 7405, 7410 or probe insertion. The surgeon then uses the software to plan the trajectories for hardware instrumentation (e.g., pedicle screw, facet screw). Some embodiments of the software will allow any number of trajectories to be stored for use during the procedure, with each trajectory accompanied by a descriptor that may just be the level and side of the spine where screw insertion is planned.

In some embodiments, the robot 15 is moved next to the table and cameras 8200 for tracking robot 15 and patient 18 are activated. The cameras 8200 are positioned near the patient's head. In some embodiments, the markers for the robot 15 are facing toward the cameras 8200, typically in the positive y-axis 68 direction of the robot's coordinate system. In some embodiments, a screen can be accessed to show where the robot 15 is located relative to all the trajectories that are planned for the current Z-frame 72 position. Using this screen it can be confirmed that the trajectories planned are within the range of the robot's reach. In some embodiments, repositioning of the robot 15 to a location that is within range of all trajectories is performed at this time. Alternately or additionally, in some embodiments, the surgeon can adjust the Z-frame 72 position, which will affect the range of trajectories that the robot 15 is capable of reaching (converging trajectories require less x-y reach the lower the robot 15 is in Z). During this time, simultaneously in some embodiments, a screen shows whether markers 720 on the patient 18 and robot 15 are in view of the cameras 8200. Repositioning of the cameras 8200, if necessary, is also performed at this time for good visibility.

In some embodiments, the surgeon then selects the first planned trajectory and he/she (or assistant) presses "go". The robot 15 moves in the x-y (horizontal) plane and angulates roll 62 and pitch 60 until the end-effectuator 30 tube intersects the trajectory vector. During the process of driving to this location, in some embodiments, a small laser light will indicate end-effectuator 30 position by projecting a beam down the trajectory vector toward the patient 18. This laser simply snaps into the top of the end-effectuator guide tube 50. When the robot's end-effectuator guide tube 50 coincides with the trajectory vector to within the specified tolerance, auditory feedback is provided in some embodiments to indicate that the desired trajectory has been achieved and is being held. In some embodiments, movement of the patient 18 or robot 15 is detected by optical markers 720 and the necessary x-axis 66, y-axis 68, roll 62, and pitch 60 axes are adjusted to maintain alignment.

In some embodiments of the invention, the surgeon then drives Z-frame 72 down until the tip of the end-effectuator 30 reaches a reasonable starting distance from the site of operation, typically just proximal to the skin surface or the first tissues encountered within the surgical field 17. While moving, the projected laser beam point should remain at a fixed location since movement is occurring along the trajectory vector. Once at the desired location, the user may or may not select an option to lock the Z-tube 50 position to remain at the fixed distance from the anatomy during breathing or other movement.

One problem with inserting conventional guide-wires and screws into bone through any amount of soft tissue is that the screw or wire may sometimes deflect, wander, or "skive" off of the bone in a trajectory that is not desired if it does not meet the bone with a trajectory orthogonal to the bone surface. To overcome this difficulty, some embodiments can use a specially designed and coated screw specifically intended for percutaneous insertion. Some other embodiments can use an end-effectuator 30 tip fitted with a guide tube 50 or dilator, capable of being driven all the way down to the bone. In this instance, the guide tube 50 needs to have a sharp (beveled) leading edge 30b, and may need teeth or another feature to secure it well to the bone once in contact. This beveled tube 50 (i.e. guide tube 50 that includes beveled leading edge 30b) is driven through soft tissue and next to bone through one of two different methods using the surgical robot system 1 as described.

Figure 29:
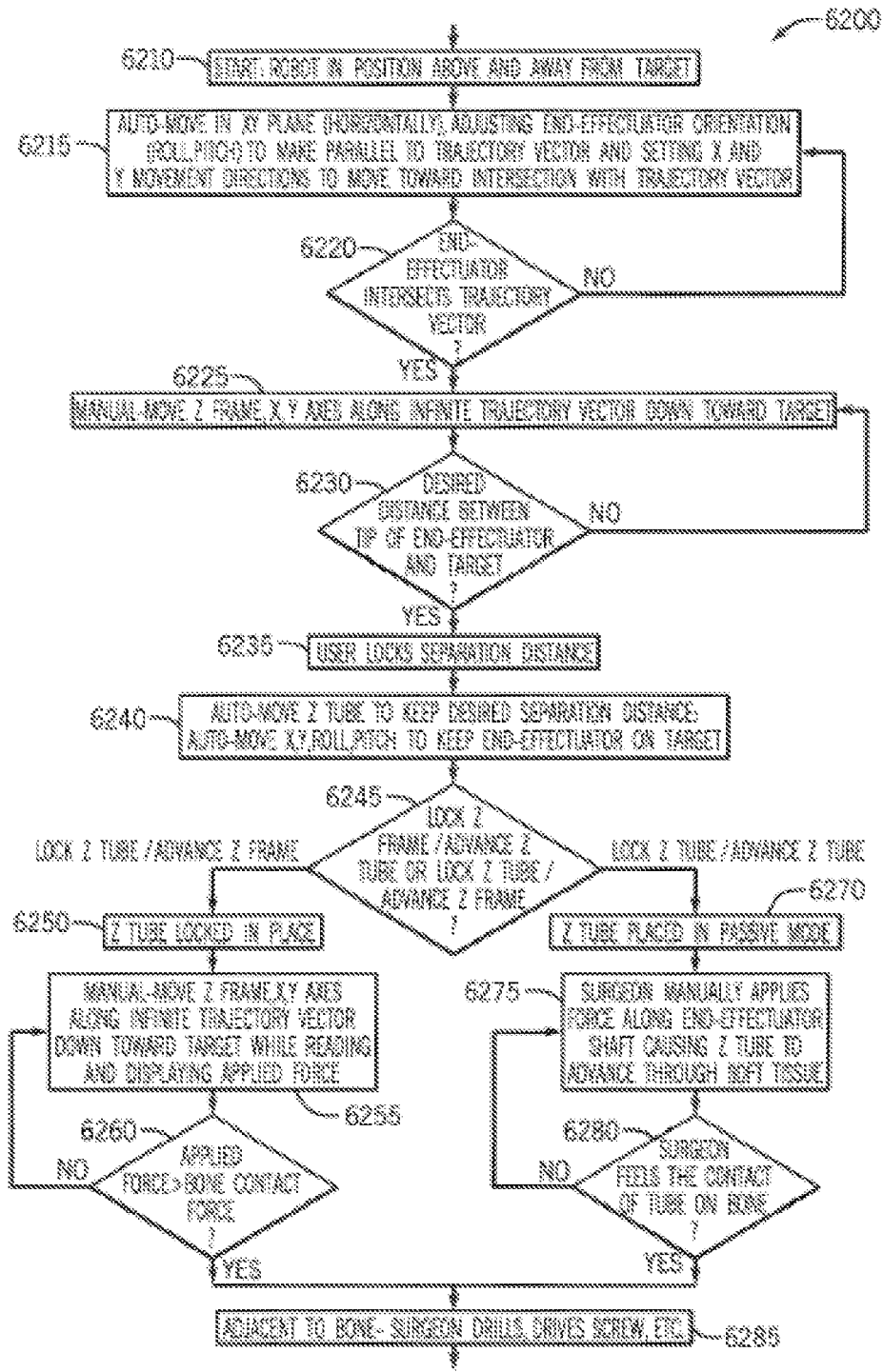
FIG. 29 illustrates a method in accordance with at least one embodiment of the invention.

In applications where conventional screws are to be driven into bone, the surgeon may want to move the end-effectuator tip 30, fitted with a guide tube 50 or a conventional dilator, all the way down to the bone. Referring to FIG. 29 showing steps 6210, 6215, 6220, 6225, 6230, 6235, 6240, 6245, and either 6250, 6255, 6260, and 6260, or 6270, 6275, 6280 and 6285, two embodiments address this need. In some embodiments, the user can insert the tube 50 and force it down the axis Z-tube axis 64 by hand, or with the robot 15 until a peak in force is registered by tactile feel or by a conventional force sensor on the end-effectuator 30 (signaling contact with bone). At this point, it is no longer necessary for the tip of the drill bit 42 to be positioned past the tip of the tube 50 (in fact be better to have it slightly retracted). As described earlier, a drill bit 42 can include a drill stop, and the drill bit 42 can be locked and held. In some embodiments, the stop on the drill bit 42 can then be adjusted by pulling one of the releases and slightly adjusting its position. Then, the tube 50 can be brought up against bone and locked there. Now, the stop can be adjusted to show how much the drill bit 42 would protrude beyond the tip. This same value can be used to offset (extrapolate) the tip of the tube 50 on the software, showing the user where the tip of the drill bit 42 will end up.

In some embodiments, the Z-tube axis 64 is fitted with a conventional force sensor with continuous force readings being displayed on the screen (such as display means 29). In some embodiments, the Z-frame 72 is then driven down into tissue while continuously adjusting the x-axis 66 and y-axis 68 to keep the tube 50 aligned with the trajectory vector. In some embodiments, the steps of 6210, 6215, 6220, 6225, 6230, 6235, 6240, 6245, 6250 and 6255 can be used to drive the tube 50 toward the target. In this instance, roll 62 and pitch 60, defining orientation, should not change while moving x-axis 66, y-axis 68, and the Z-frame 72 as Z-axis 70 along this vector, while holding Z-tube 50 rigidly locked at mid-range. For this procedure, in some embodiments, the Z-tube 50 stiffness must be set very high, and may require a conventional mechanical lock to be implemented. In some embodiments, if Z-tube 50 is not stiff enough, a counter force from the tissues being penetrated may cause it to move back in the opposite direction of Z-frame 72, and the tube 50 will not have any net advancement. In some embodiments, based on the surgeon's previous experience and lab testing, Z-frame 72 is driven down until a force level from the monitored force on Z-tube 50 matches the force typical for collision with bone (step 6260).

At this point, in some embodiments, the guide tube 50 is adjacent to bone and the surgeon may wish to drill into the bone with a conventional guide-wire or drill bit, or insert a screw. For screw prep and insertion, in some embodiments, the surgeon either uses a method that incorporates guide-wires, or a method that does not use guide-wires.

Some embodiments include a guide-wire method. For example, in some embodiments, a guide-wire is drilled into bone through the guide tube 50. After the guide-wire is in place, Z-frame 72 and tube 50 are driven upward along the trajectory vector until outside the body. In some embodiments, the tube is then released with a quick release from the robot's end-effectuator 30 so it can be positioned at the next trajectory. In some embodiments, a cannulated screw, already commonly used in spine surgery, can then be driven in place over the guide-wire.

Some embodiments include a non-guide-wire method. For example, a pilot hole may or may not be drilled first. In some embodiments, a screw is then driven into bone directly through the guide tube 50, which abuts bone. In some embodiments, the tip of the screw may have the special non-skiving design mentioned above.

In some embodiments, if hardware other than a screw is being inserted, the surgeon may wish to dilate soft tissue. In some embodiments, a dilated path would enable larger and/or more tools and implants to be inserted. In some embodiments, dilation is performed by sliding a series of larger and larger diameter tubes over the initial central shaft or tube. In some embodiments, a series of dilators, specially designed to integrate to the robot's end-effectuator 30, sequentially snap on to each other for this purpose.

In some embodiments, after the screw or hardware has been inserted in the first trajectory, the surgeon drives the robot 15 backup the trajectory vector away from the patient 18. In some embodiments, after the end-effectuator 30 is clear of the patient 18 in the Z direction, the next trajectory is selected and the robot 15 repeats the above steps.

In some embodiments, at any time during the procedure, if there is an emergency and the robot 15 is in the way of the surgeon, the "E-stop" button can be pressed on the robot 15, at which point all axes except Z-frame 72 become free-floating, and the robot's end-effectuator 30 can be manually removed from the field by pushing against the end-effectuator.

In some embodiments, for nerve avoidance during medical procedures, a special conventional dilator tube (not shown) that can be used with the robot 15. In some embodiments, the dilator tube can include multiple electrodes at its tip that can be sequentially activated to find not only whether a nerve is nearby, but also to find which radial direction is the nearest direction toward the nerve. Some embodiments incorporate this guide tube 50 and can identify, warn or incorporate automatic algorithms to steer clear of the nerve.

In some embodiments, it is known that pairs of bone screws such as pedicle screws have better resistance to screw pullout if they are oriented so that they converge toward each other. In some embodiments, for the best potential biomechanical stability, a two-screw surgical construct can consist of specially designed conventional screws that would interconnect in the X Z plane (not shown). That is, one screw can have a socket to accept a threaded portion of the other screw so that the screws interconnect at their tips. A procedure such as this requires exceptional accuracy, otherwise the screw tips would not properly intersect, and is therefore especially well-suited for a surgical robot 15. This type of hardware is useful with certain embodiments of the invention.

In some embodiments, instead of only straight lines, the surgeon has several options for trajectory planning—straight, curved or boundary for safe-zone surgery. For curved pathway planning, in some embodiments, the surgeon can draw a path on the medical image that has curvature of a user-selectable radius. In some embodiments, special conventional needles and housings can be used to execute these curved paths. In safe zone surgery (tumor or trauma), in some embodiments, the surgeon first plans a box or sphere around the region on the medical image within which the probe tip, incorporating a drill or ablation instrument, will be allowed to reside. In some embodiments, the robot 15 is driven down along a trajectory vector either automatically or manually as described above to position the tip of the probe to be in the center of the safe zone. In some embodiments, the surgeon would then be able pick the tool's axis of rotation (orthogonal to the long axis) based on the desired impact he/she would like for the purpose of preserving tissue and maximizing efficiency and effectiveness for the task at hand. For example, in some embodiments, an axis of rotation at the surface of the skin could be selected to minimize the amount by which the tool travels laterally and rips the skin.

In some embodiments, the robot 15 uses optical markers for tracking. Some embodiments are able to provide accurate localization of the robot 15 relative to the patient 18, and utilize the LPS because of the advantage of not being limited to line-of-sight. Additionally, in some embodiments, probes utilizing RF emitters on the tip (capable of being tracked by the LPS) can be used for steering flexible probes inside the body. In some embodiments, if the LPS is not yet functional for localization, then localization can be performed using an electromagnetic system such as the Aurora by Northern Digital. Aurora® is a registered trademark of Northern Digital Inc. For example, in this instance, an electromagnetic coil and RF emitters are both present in the probe tip. Some embodiments can offer the option of LPS or electromagnetic localization with steerable needles 7600. In this embodiment of the invention, the surgeon can monitor the current location on the medical image where the probe tip is currently positioned in real-time and activate RF electrodes to advance and steer the probe tip in the desired direction using a joystick.

Figure 30A:
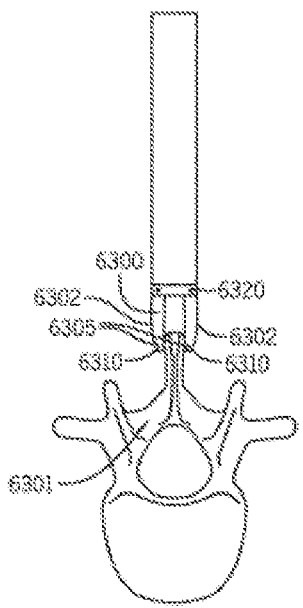
FIGS. 30A-30C illustrates various embodiments of an end-effectuator including a modified mount with a clamping piece in accordance with at least one embodiment of the invention.
Figure 30B:
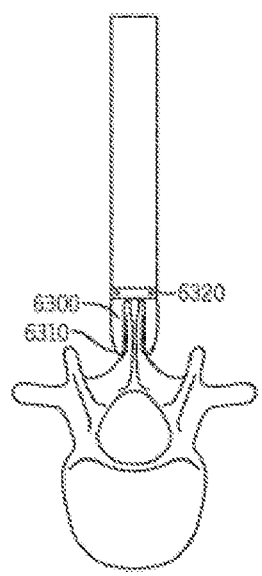

As discussed earlier, in some embodiments, the end-effectuator 30 can include a bayonet mount 5000 is used to removably couple the surgical instrument 35 to the end-effectuator 30 as shown in FIG. 15. Some embodiments can include a modification to the mount 5000 allowing the ability to slide a clamping piece 6300 over the spinous process 6301 without full exposure of the spinous process 6301. See example FIGS. 30A-30B illustrating various embodiments of an end-effectuator 30 including a modified mount 5000 with a clamping piece 6300 in accordance with at least one embodiment of the invention. As shown, the clamping piece 6300 comprises clamps 6302 including at least one beveled edge 6310, and clamp teeth 6330.

In some embodiments, the surgeon would make a stab incision in the midline and then slide the clamps 6302 of the clamping piece 6300 down along the sides of the spinous process 6301, pushing tissue away as the tip of the clamping piece is advanced. In some embodiments, the leading edge of the clamping mechanism 6300 would be beveled (see the leading edges 6305 of each clamp 6302 of the clamping mechanism 6300), and have a shape similar to a periosteal elevator. This allows the clamping mechanism 6300 to separate the muscle tissue from the bony spinous process 6301 as it is advanced. In some embodiments, the leading edges 6305 of the clamping mechanism 6300 can be electrified to enable it to more easily slide through muscle and connective tissues to prevent excessive bleeding.

Figure 30C:
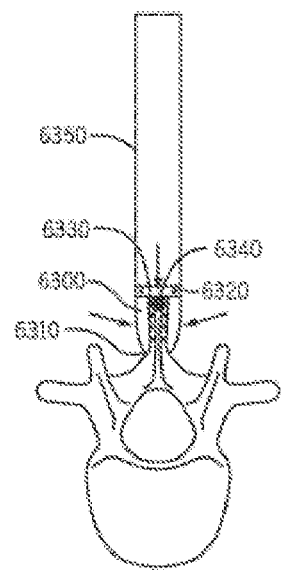

In some embodiments, a mechanism activated from farther back on the shaft (for example a turn screw 6320, or conventional spring, etc.) can be activated to deploy clamp teeth 6330 on the clamps 6302. The same mechanism or another mechanism would close and compress the clamps 6302 together to firmly secure the clamping mechanism 6300 to the spinous process 6301 (see FIGS. 30B-30C). Additionally, in some embodiments, a screw 6340 aligned with the handle 6350 could deploy to thread into the spinous process 6301 (see for example, FIG. 30C).

The embodiments as described above and shown in FIGS. 30A-30C would be especially well suited to percutaneous pedicle screw-rod surgery because the hole made for mounting the clamping mechanism 6300 could also be used as the hole for inserting the conventional rod to interconnect the conventional pedicle screw heads. Further, the embodiments as described above and shown in FIGS. 30A-30C could also be useful for mounting a marker tree to other bony prominences, such as transverse processes, long bones, skull base, or others.

Figure 31:
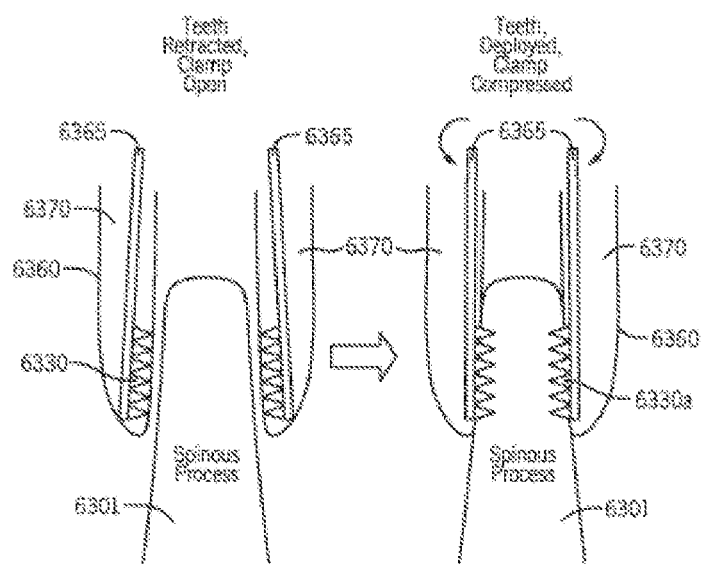

FIGS. 31 and 32 illustrate embodiments of clamping piece 6300 actuation on a spinous process 6301 in accordance with some embodiments of the invention. In some embodiments, the mechanism for deploying the clamp teeth 6330 could be comprised of a hollow tool tip 6360 containing teeth 6330 that are to one side of the hollow cavity 6370 during insertion, but are forced toward the opposite side when the mechanism is deployed, such that the embedded teeth penetrate the bone (see the illustration of penetrated teeth 6330a in FIG. 31).

FIG. 32 shows an alternative embodiment of the clamping piece 6300 actuation on a spinous process 6301. As shown, the groups of teeth 6330 are attached to rods 6365 that rundown the hollow cavities 6360a of the hollow tool tips 6360. These rods 6365 pivot farther up the handle 6350 (pivot point not pictured) and the clamp teeth 6330 are forced together. For example, in some embodiments, rods 6365 are driven into the hollow cavity 6360a of the hollow tool tip 6360 on the side away from the bone, forcing the clamp teeth 6330 against and into the bone (for example, see the penetrated teeth 6330a in FIG. 32).

As described above, the opaque markers 730 must be included in a CT scan of the anatomy. However, it is desirable to crop CT scans as close as possible to the spine to improve resolution. In some embodiments, instead of using markers 730 near where the active markers 720 are located, an alternative is to have a rigid extension containing opaque markers 730 that are temporarily attached near the spine when the scan is taken. In some embodiments, the clamping piece 6300 can be coupled with, or otherwise modified with a targeting fixture 690. For example, FIG. 33A illustrates a clamping piece 6300 modified with a targeting fixture 690 including a temporary marker skirt 6600 in accordance with at least one embodiment of the invention, and FIG. 33B illustrates a clamping piece 6300 modified with a targeting fixture 690 as shown in FIG. 33A with the temporary marker skirt 6600 detached in accordance with at least one embodiment of the invention. As shown, the temporary marker skirt 6600 includes radio-opaque markers 730 in a temporary "skirt" around the base of the clamping device 6300. The design of the temporary marker skirt 6600 and clamping device 6300 must be such that the markers 730 in the skirt 6600 have known locations relative to the markers 720 for tracking that are farther away. Once the scan is taken, the opaque markers 730 are not needed. Therefore, in some embodiments, by depressing a conventional release, the skirt 6600 can be removed so it will not be in the way of the surgeon (see for example FIG. 33B).

Figure 34:
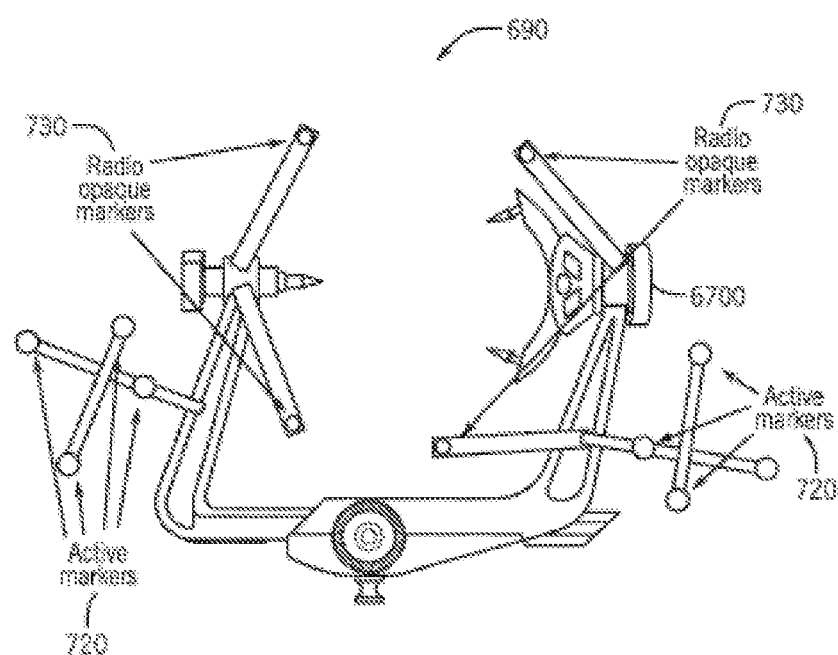
FIG. 34 shows a modified Mayfield frame 6700 including one possible configuration for active and radio-opaque markers in accordance with one embodiment of the invention.

In some embodiments, it may also be desirable to mount the targeting fixture 690 to another piece that is already rigidly attached to the patient 18. For example, for deep brain stimulation or other brain procedure where the patient 18 is positioned in a Mayfield head holder, the head holder could serve as an attachment point for the targeting fixture 690. Since the head holder 6700 and skull form a rigid body, it is possible to track the head holder 6700 under the assumption that the skull moves the same amount as the head holder 6700. Further, in some embodiments of the invention, a surveillance marker (such as surveillance marker 710 as illustrated in FIG. 3) could be used. For this targeting fixture 690, active 720 and radio-opaque 730 markers would be rigidly attached to the head holder 6700. The radio-opaque markers 730 need only be in position when the scan (CT, MRI, etc.) is taken and could subsequently be removed. The active markers 720 need not be in position when the scan is taken but could instead be snapped in place when it is necessary to begin tracking. For example, FIG. 34 shows one possible configuration for active 720 and radio-opaque markers 730 attached to a Mayfield frame 6700 in accordance with one embodiment of the invention. As with other targeting fixtures 690, it is required that three or more radio-opaque markers 730 and three or more active markers 720 are attached to same rigid body.

One problem with some robotic procedures is that the guide tube 50 must be physically rigidly mounted to the robot's end-effectuator, and therefore mounting one or more dilator tubes can be challenging. To address this problem, in some embodiments, dilators can be placed over the central guide-tube 50 without removing the robot end-effectuator 30. For example, some embodiments can include an end-effectuator 30 that includes at least one dilator tube 6800, 6810. For example, FIG. 35 shows end-effectuator 30 that includes nested dilators 6805 in accordance with at least one embodiment of the invention. As shown, a nested set 6805 of two or more disposable or non-disposable dilators 6800, 6810 can be mounted onto the robot's end-effectuator 30. In some embodiments, each dilator 6800, 6810 may have its own removable conventional handle that allows a surgeon or an automated mechanism to force the dilator down into soft tissue. Some embodiments could include additional dilators, for example, a nested set of three dilators of 7 mm, 11 mm, and 14 mm diameter (not shown) may be useful for creating a portal for minimally invasive screw insertion or application of a surgical implant. In some embodiments, each dilator 6800, 6810 can have greater length as it is closer to the central guide tube 50, allowing the more central tube 50 to be advanced without radially advancing the dilator tubes 6800, 6810 out further.

In some further embodiments, the system 1 can include an end-effectuator 30 that is coupled with at least one cylindrical dilator tube 6900. For example, FIGS. 36A-36C illustrate various embodiments of an end-effectuator 30 including cylindrical dilator tubes 6900 in accordance with at least one embodiment of the invention. As shown, in some embodiments, the cylindrical dilator tubes 6900 can be formed from two-halves that snap together. In some embodiments, the cylindrical dilator tubes 6900 can be formed from two-halves that snap together, and in some embodiments, the two-halves snap together over a previous dilator tube 6900. In some embodiments, the tubes 6900 can be fashioned so that they are strong in resisting radial compression, but not necessarily strong in resisting radial expansion (since their opposing force will be the resisting soft tissues). In some embodiments, the tubes 6900 can also benefit from a mechanism for temporarily attaching a conventional handle at the proximal end for easy insertion then removal of the handle following insertion. Moreover, some embodiments include a mechanism for grasping and extracting each tube 6900 or a cluster of tubes 6900, or for attaching one or more tubes 6900 to the central guide tube 50. As depicted in FIGS. 36B and 69C, when the robot's end-effectuator 30 is raised (following the tube 6900 insertion depicted in FIG. 36B), the tube 6900 or cluster of tubes 6900 is extracted with it, leaving behind the outermost dilator 6910a and forming a corridor for surgery. Further, in some embodiments, the surgeon can send the robot's end-effectuator 30 to coincide with the infinite vector defining the desired trajectory, but above the patient 18. In some embodiments, the surgeon then sends the robot's end-effectuator 30 down this vector until the tip of the central guide pin or tube 50 is ready to penetrate soft tissue. In some embodiments, a starter incision may be made to help the central guide tube 50 penetrate the tissue surface. In some embodiments, the surgeon continues to send the robot's end-effectuator 30 down the trajectory vector, penetrating soft tissue, until the target is reached (for example, when the tube 50 abuts bone of a target region). Then, in some embodiments, while the robot 15 holds the central tube 50 steady, each sequential dilator 6900 is slid down the central tube 50 over the previous dilator 6900. When desired dilation is complete, in some embodiments, the proximal end of the dilator tube 6900 may be secured to the patient 18 (or external assembly), and the central tube 50 and all but the outermost dilator tube 6910 would be removed.

Some embodiments include tubes 6900 that comprise a polymeric material. In some embodiments, the tubes 6900 can include at least one either radiolucent or radio-opaque material. In some embodiments, dilators 6900 may be radio-opaque so that their position may be easily confirmed by x-ray. Further, in some embodiments, the outermost dilator 6910 may be radiolucent so that the position of pathology drawn out through the tube, or implants, or materials passed into the patient through the tube, may be visualized by x-ray.

As described earlier, in some embodiments, the use of conventional linear pulse motors within the surgical robot 15 can permit establishment of a non-rigid position for the end-effectuator 30 and/or surgical instrument 35. In some embodiments, the use of linear pulse motors instead of motors with worm gear drive enables the robot 15 to quickly switch between active and passive modes.

The ability to be able to quickly switch between active and passive modes can be important for various embodiments. For example, if there is a need to position the robot 15 in the operative field, or remove the robot 15 from the operative field. Instead of having to drive the robot 15 in or out of the operative field, in some embodiments, the user can simply deactivate the motors, making the robot 15 passive. The user can then manually drag it where it is needed, and then re-activate the motors.

Figure 37:
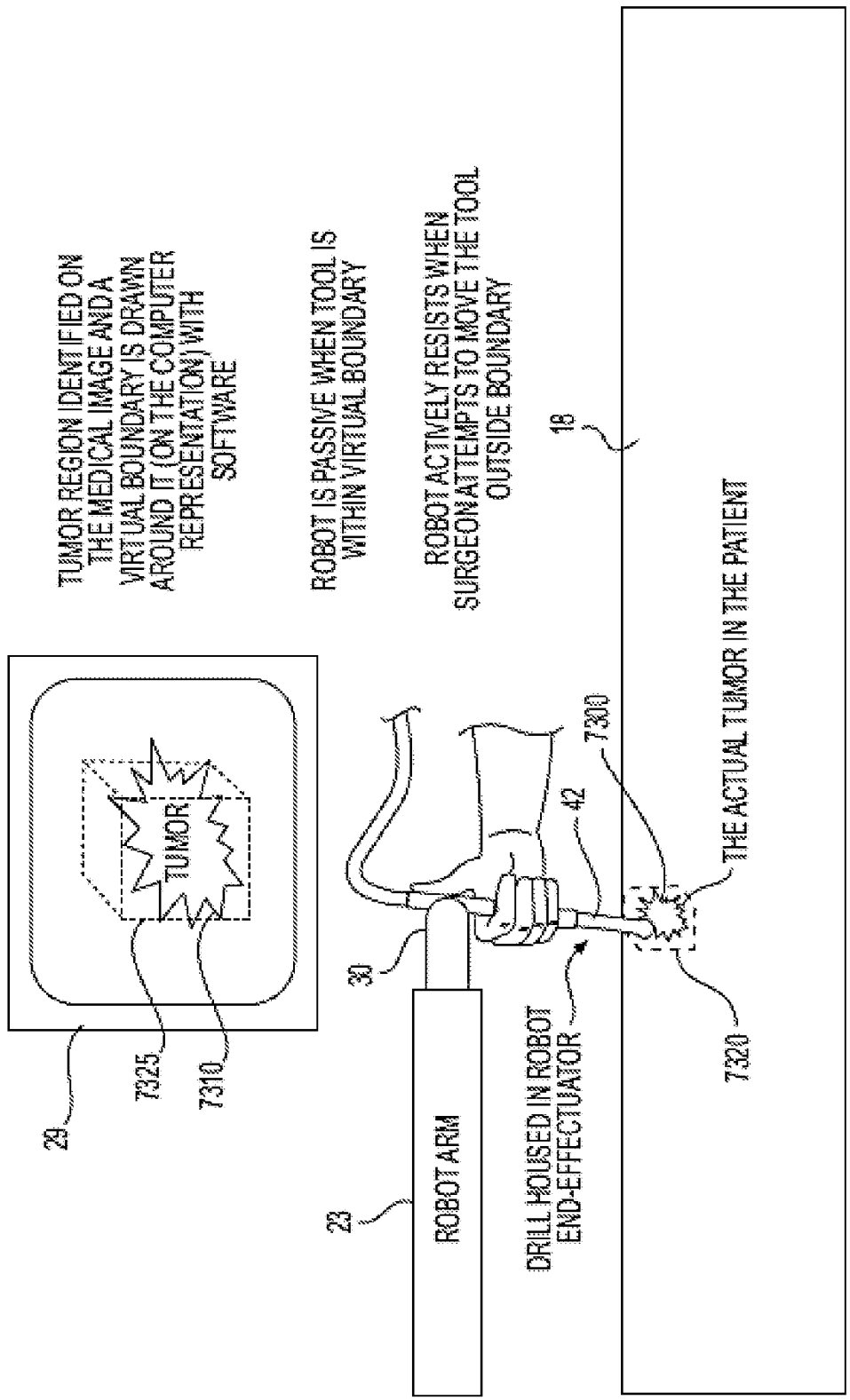
FIG. 37 illustrates a method in accordance with at least one embodiment of the invention.

The ability to be able to quickly switch between active and passive modes can be important for safe zone surgery. In some embodiments, the user can outline a region with pathology (for example a tumor 7300) on the medical images (see for example FIG. 37 showing the displayed tumor 7310 on display means 29). In some embodiments, algorithms may then be implemented where the robot 15 switches from active to passive mode when the boundary of the region is encountered. For example, FIG. 37 shows the boundary region 7320 within the patient 18 displayed as region 7325 on the display means. Anywhere outside the boundary 7320, the robot becomes active and tries to force the end-effectuator 30 back toward the safe zone (i.e. within the boundary 7320). Within the boundary 7320, the robot 15 remains passive, allowing the surgeon to move the tool (such as drill bit 42) attached to the end-effectuator 30.

In some further embodiments, the user can place restrictions (through software) on the range of orientations allowed by the tool within the safe zone (for example, boundary 7320, and displayed as boundary 7325 in FIG. 37). In some embodiments, the tool can only pivot about a point along the shaft that is exactly at the level of the skin. In this instance, the robot 15 freely permits the surgeon to move in and out and pivot the end-effectuator 30, but does not allow left-right or front-back movement without pivoting. For example, in some embodiments, if the surgeon wants to reach a far left point on the tumor 7300, the surgeon must pivot the tool about the pivot point and push it to the appropriate depth of insertion to satisfy the boundary 7320 conditions and force the tip (for example, the tip of the drill bit 42) to that location. This type of limitation can be valuable because it can prevent the surgeon from "ripping" tissue as the drill is moved around to destroy the tumor 7320. Further, it also allows the surgeon to access a safe zone farther distal while keeping clear of a critical structure farther proximal.

Some embodiments include curved and/or sheathed needles for nonlinear trajectory to a target (for example, such as a tumor 7320 described earlier). In some embodiments, with a curved trajectory, it is possible to approach targets inside the body of a patient 18 that might otherwise be impossible to reach via a straight-line trajectory. For example, FIG. 38A illustrates a robot end-effectuator 30 coupled with a curved guide tube 7400 for use with a curved or straight wire or tool 7410 in accordance with at least one embodiment of the invention. In some embodiments, by forcing a curved or straight wire or tool 7410 through the curved guide tube 7400, at least some curvature will be imparted to the wire or tool 7410. In some embodiments, the curved or straight wire or tool 7410 may comprise a compliant wire capable of forming to the curvature of the guide tube 7400. In some other embodiments, the curved or straight wire or tool 7410 may comprise a non-compliant wire, capable of substantially retaining its shape after entering and exiting the guide tube 7400. A disadvantage of using a very compliant wire is that the tissues that it encounters may easily force it off the desired path. A disadvantage of using a very non-compliant wire is that it would be difficult to achieve a useful amount of curvature. Further, forcing a straight wire of intermediate compliance through a curved guide tube 7400 may produce some curvature of the wire, but less curvature than that of the guide tube 7400. It is possible to mathematically or experimentally model the mechanical behavior of the wire 7410 to determine how much curvature will be imparted. For example, by knowing the orientation of the guide tube 7400, in some embodiments, the robot may be used to accurately guide the curved wire 7410 to a desired target by using computerized planning to predict where the wire 7410 would end up as it traveled through tissue. Further, in some embodiments a very non-compliant wire or tool 7410 can be manufactured in the shape of an arc with a specific radius of curvature, and then fed through a guide tube 7400 with the same radius of curvature. By knowing the orientation of the guide tube 7400 (i.e. substantially the same as wire or tool 7410), computerized planning can be used to predict where the wire or tool 7410 would end up as it traveled through tissue.

Some other embodiments may use a straight guide tube 50 with a wire or tool 7410 that may be curved or straight. For example, FIG. 38B illustrates a robot end-effectuator 30 coupled with a straight guide tube 50 for use with a curved or straight wire or tool 7405, 7410 in accordance with at least one embodiment of the invention. Some surgical methods may use curved needles 7410 that are manually positioned. In general, the needles consist of a rigid, straight outer guide tube through which is forced an inner needle 7405 with tendency to take on a curved shape. In existing manual devices, the inner needle 7405 is comprised of nitinol, a shape memory alloy, and is formed with significant curvature. This curved needle 7410 is flattened and then fed through the outer guide tube. When it exits the other end of the guide tube, it bends with significant force back toward its original curved configuration. Such a system could be adapted for use with the robot 15 if the curvature of the exiting portion of the needle per unit measure exiting is known, if the radial position of the curved needle 7410 relative to the straight housing is known. In some embodiments, the radial position of the curved needle 7410 can be determined by using marks placed on the curved and straight portions, or through a non-circular cross-section of the straight guide tube and curved needle 7410 (for example, square cross-section of each). In this instance, in some embodiments, it would then be possible to preoperatively plan the path to the target (such as a tumor 7300) and then adjust the robot 15 to guide the curved wire or tool 7410 through this path. In some embodiments, the system 1 can include the ability to electrically stimulate distally while advancing a wire (for example, such as wire 7405, 7410) through soft tissue. For example, some embodiments include a guide tube 7500 capable of being coupled to the robot 15 by end-effectuator 30 that is insulated along its entire shaft but has an electrode 7510 on or near the tip (see for example FIG. 39). In some embodiments, the use of the tube 7500 to perform electromygraphy ("EMG") can enable the system 1 to detect whether nerves come in contact with the guide tube 7500 as the guide tube 7500 is advanced. Some alternative embodiments can include a conventional pin (for example, stainless steel pins such as Kirschner-wires) instead of a tube 7500, insulated along its shaft but not at the tip. In some embodiments, the wire could be connected to a stimulator outside the body and would have the ability to stimulate distally while advancing the pin through soft tissue. In some embodiments, stimulation would allow the ability to identify critical tissue structures (i.e., nerves, plexus).

In some further embodiments, a portion of the leading edge of the guide tube 7500 may be insulated (i.e. comprise a substantially non-electrically conductive area), and a portion of the leading edge may be uninsulated (i.e. the region is inherently electrically conductive area). In this instance, it can be possible to determine the radial direction of the tube 7500 that is closest to the nerve by watching the response as the tube 7500 is rotated. That is, as the tube 7500 is rotated, the EMG nerve detection will have the most pronounced response when the uninsulated portion is nearest the nerve, and the least pronounced response when the uninsulated portion is farthest from the nerve. In some embodiments, it would then be possible for the user to manually steer the robot 15 to automatically steer the tube 7500 farther away from the nerve. In addition, this modified tube 7500 could have a conventional fan-like retractor (not shown) that can be deployed to gently spread the underlying muscle fibers, thereby making an entry point for disk removal, or screw insertion. In some embodiments, the combination of EMG and gentle retraction can enhance the safety and outcomes of robotic assisted spinal surgery.

As described above, one way of taking advantage of the directional electromyographic response is for the user to manually rotate the tube 7500. In some other embodiments, the tube 7500 can be to continuously oscillated back and forth, rotating about its axis while potentials are monitored. In some embodiments, to achieve the same function without rotating the tube 7500, the leading edge of the tube 7500 could have conductive sections that could be automatically sequentially activated while monitoring potentials. For example, in some embodiments, an array of two, three, four, or more electrodes 7510 (shown in FIG. 39) can be positioned around the circumference of the leading edge of the tube 7500. As shown in FIG. 39, regions 7511 between the electrodes 7510 are insulated from each other (because the outer surface of 7500 is insulated). In some embodiments, the electrodes 7510 can be sequentially activated at a very high rate while recording potentials, and correlating which electrode produces the greatest response.

Some embodiments can include a steerable needle capable of being tracked inside the body. For example, U.S. Pat. No. 8,010,181, "System utilizing radio frequency signals for tracking and improving navigation of slender instruments during insertion in the body", herein incorporated by reference, describes a steerable flexible catheter with two or more RF electrodes on the tip, which are used for steering. According to the method described in U.S. Pat. No. 8,010, 181, the side or sides of the tip where the electrodes emit RF have less friction and therefore the probe will steer away from these sides.

Figure 40:
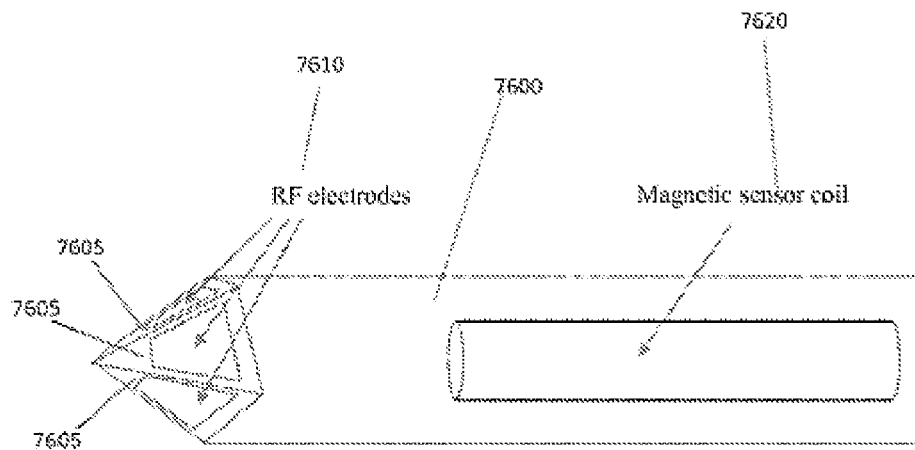
FIG. 40 illustrates a steerable and trackable needle in accordance with at least one embodiment of the invention.

In some embodiments of the invention, a steerable needle 7600 can be coupled with the system 1. In some embodiments, the system 1 can include a steerable needle 7600 coupled with the robot 15 through a coupled end-effectuator 30, the steerable needle 7600 capable of being tracked inside the body of a patient 18. For example, FIG. 40 illustrates a steerable needle 7600 in accordance with at least one embodiment of the invention. In some embodiments, steerable needle 7600 can comprise a plurality of flattened angled bevels 7605 (i.e. facets) on the tip of the probe, with each flat face of each bevel 7605 having an RF electrode 7610. A magnetic coil sensor 7620 embedded within the needle 7600 can enable localization of the tip adjacent to the electrodes 7610. In some embodiments, RF can be used for steering, whereas localization would use electrodes 7610 with the magnetic coil sensor 7620. Some embodiments as described may use off-the-shelf electromagnetic localization system such as the Aurora® from Northern Digital, Inc. (http://www.ndigital.com), which has miniature coils capable of fitting inside a catheter.

Figure 41:
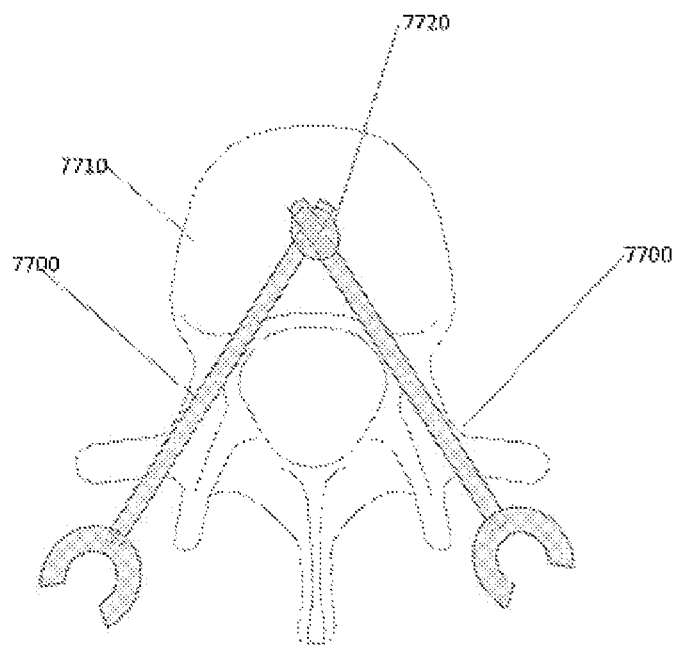
FIG. 41 illustrates one embodiment of intersecting and interlocking bone screws in accordance with at least one embodiment of the invention.

During surgical procedures, pedicle screws or anterior body screws are inserted in two locations. However, there is a chance of failure due to screw pullout. To enhance resistance to pullout, screws are angled toward each other. For example, some embodiments can include intersecting and interlocking bone screws 7700 such as those illustrated in FIG. 41, illustrating one embodiment of intersecting and interlocking bone screws 7700 in accordance with at least one embodiment of the invention. As shown, bone screws 7700 can be coupled and can intersect and interlock 7720. In some embodiments, the intersecting and interlocking bone screws 7700 as shown can be removed without destroying a large area of bone.

Figure 48:
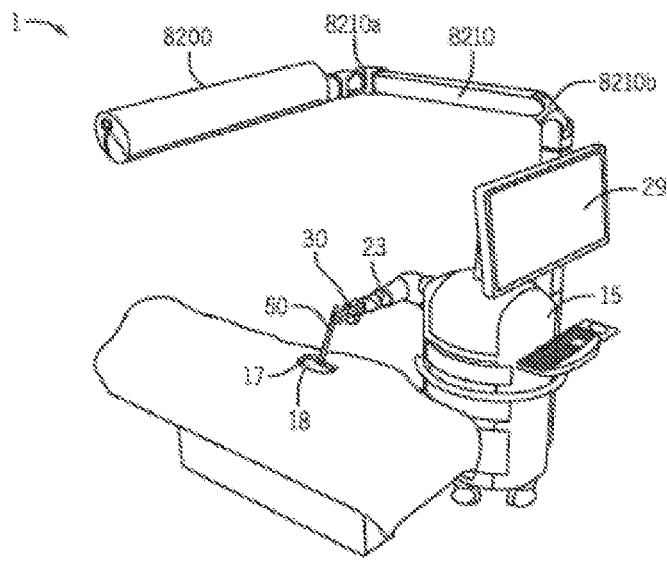
FIG. 48 illustrates a perspective view of a robot system including a camera arm in accordance with one embodiment of the invention.

Some embodiments of the system 1 can include conventional tracking cameras with dual regions of focus. For example, camera units such as Optotrak® or Polaris® from Northern Digital, Inc., can be mounted in a bar so that their calibration volume and area of focus are set. Optotrak® or Polaris® are registered trademarks of Northern Digital, Inc (see for example FIG. 48 showing camera bar 8200). In some embodiments, when tracking the robot 15 and targeting fixture 690 with optical trackers (for example, active markers 720), maintaining markers 720 within the center of the volume can provide the best focus. However, it is not possible for both the targeting fixture's 690 markers and the robot's 15 markers to be substantially centered simultaneously, and therefore both are offset from center by substantially the same distance.

In some embodiments, one solution to this issue is to set up two pairs of cameras 8200 with one camera shared, that is, cameras 1 and 2 form one pair, and cameras 2 and 3 form another pair. This configuration is the same as the Optotrak® system (i.e., three cameras in a single bar), however, the Optotrak® only has one volume and one common focal point. Conversely, some embodiments of the invention would be tuned to have two focal points and two volumes that would allow both the targeting fixture 690 and the robot 15 to be centered at the same time. In some embodiments, the orientations of the lateral cameras can be adjusted by known amounts with predictable impact on the focal point and volume.

In a further embodiment of the invention, two separate camera units (for example, two Polaris® units) can be mounted to a customized conventional bracket fixture including adjustment features (not shown). In some embodiments, this fixture would be calibrated so that the vectors defining the directions of the volumes and distance to focal point can be adjustable by known amounts. In some embodiments, the user could then point one Polaris® unit at the robot's markers, and the other Polaris® unit at the targeting fixture's 690 markers 720. The position of the adjustment features on the bracket would tell the computer what the transformation is required to go from one camera's coordinate system to the other.

In some further embodiments, the cameras 8200 (such as Optotrak® or Polaris®) focused on a particular region could be further improved by a conventional automated mechanism to direct the cameras 8200 at the center of the target. Such a method would improve accuracy because in general, image quality is better toward the center of focus than toward the fringes. In some embodiments, conventional motorized turrets could be utilized to adjust azimuth and elevation of a conventional bracket assembly for aiming the cameras 8200 (and/or in conjunction with movement of cameras 8200 on camera arm 8210 as shown in FIG. 48). In some embodiments, feedback from the current location of active markers 720 within the field of view would be used to adjust the azimuth and elevation until the camera 8200 points directly at the target, regardless of whether the target is the center (mean) of the markers 720 on the robot 15, the center of markers 720 on the targeting fixture 720, or the center of all markers 720. In some embodiments, such a method would allow the center of focus of the cameras 8200 to continuously move automatically as the patient 18 or robot move, ensuring the optimal orientation at all times during the procedure.

Figure 42A:
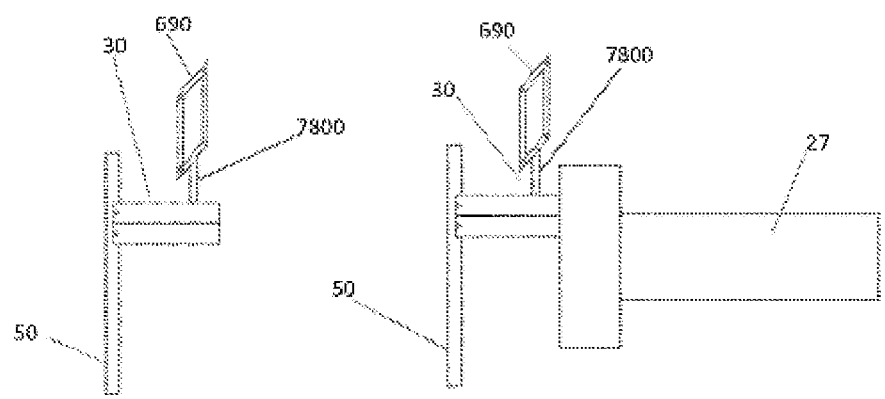
FIG. 42A-42B illustrates configurations of a robot for positioning alongside a bed of a patient that includes a targeting fixture coupled to an end-effectuator using a snap-in post.
Figure 42B:
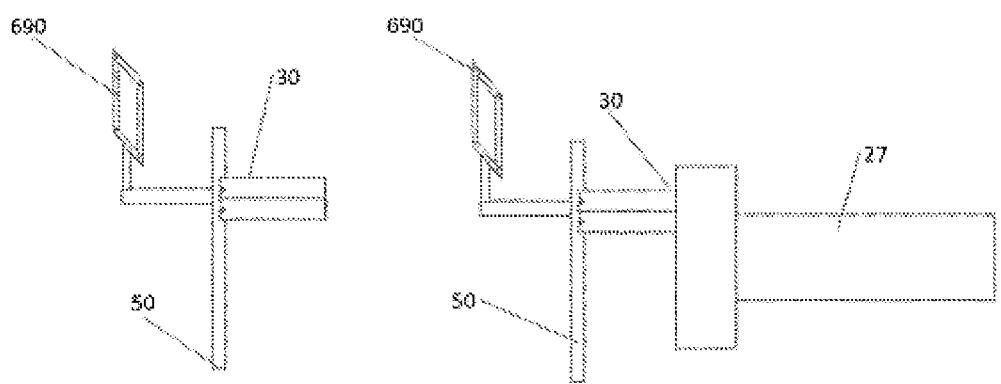

Some embodiments can include a snap-in end-effectuator 30 with attached tracking fixtures 690 (including active markers 720). For example, some embodiments include snap-in posts 7800 attached to the end-effectuator 30 and tracking fixtures 690. In some embodiments, the snap-in posts 7800 can facilitate orienting tracking markers 720 to face cameras 8200 in different setups by allowing markers 720 to be mounted to each end-effectuator 30. FIG. 42A-42B illustrates configurations of a robot 15 for positioning alongside a bed of a patient 18 that includes a targeting fixture 690 coupled to an end-effectuator 30 using a snap-in post 7800. In some embodiments, with the robot 15 in a typical configuration alongside a bed with the patient's 18 head toward the left, one end-effectuator 30 could have right-facing markers 720 (fixture 690) (illustrated in FIG. 42A) for cameras 8200 positioned at the foot of the bed. In some embodiments, the same type of end-effectuator 30 could have left-facing markers 720 (fixture 690) for cameras 8200 positioned at the head of the bed (illustrated in FIG. 42B). In some embodiments, the fixtures 690 are mounted where they would be closer to the cameras 8200 than the end-effectuator 30 so that the surgeon does not block obscure the markers 720 from the camera when using the tube 50. In some further embodiments, each interchangeable end-effectuator 30 could include conventional identification electronics. For example, in some embodiments, each interchangeable end-effectuator 30 could include an embedded conventional chip and a press-fit electrical connector. In some embodiments, when the system 1 includes a snap-in end-effectuator 30 with attached tracking fixtures 690, the computer 100 may recognize which end-effectuator is currently attached using the identification electronics. In some embodiments, when the system 1 includes a snap-in end-effectuator 30 with attached tracking fixtures 690, the computer 100 may recognize which end-effectuator is currently attached using the identification electronics, and apply stored calibration settings.

The robot system 1 contains several unique software algorithms to enable precise movement to a target location without requiring an iterative process. In some embodiments, an initial step includes a calibration of each coordinate axis of the end-effectuator 30. During the calibration, the robot 15 goes through a sequence of individual moves while recording the movement of active markers 720 that are temporarily attached to the end-effectuator (see FIG. 43). From these individual moves, which do not have to fall in a coordinate system with orthogonal axes, the required combination of necessary moves on all axes is calculated.

Figure 43:
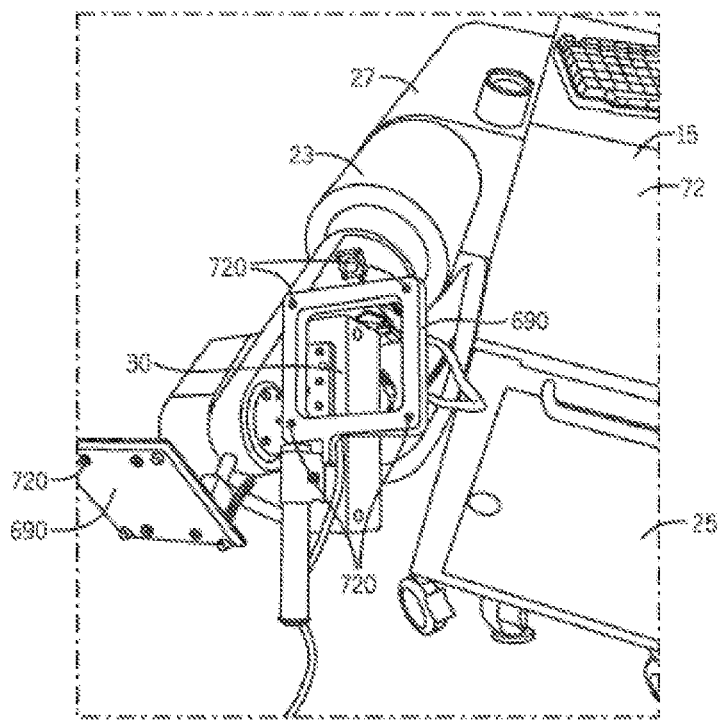
FIG. 43 illustrates a surgical robot having a plurality of optical markers mounted for calibration and tracking movement in accordance with one embodiment of the invention.

In some embodiments, it is possible to mount optical markers 720 for tracking the movement of the robot 15 on the base of the robot 15, then to calculate the orientation and coordinates of the guide tube 50 based on the movement of sequential axes. The advantage of mounting markers 720 on the base of the robot 15 is that they are out of the way and are less likely to be obscured by the surgeon, tools, or parts of the robot. However, the farther away the markers 720 are from the end-effectuator 30, the more the error is amplified at each joint. At the other extreme, it is possible to mount the optical markers 720 on the end-effectuator 30 (as illustrated in FIG. 43). The advantage of mounting markers 720 on the end-effectuator is that accuracy is maximized because the markers 720 provide feedback on exactly where the end-effectuator 30 is currently positioned. A disadvantage is that the surgeon, tools, or parts of the robot 15 can easily obscure the markers 720 and then the end-effectuator's 30 position in space cannot be determined.

In some embodiments, it is possible to mount markers 720 at either extreme or at an intermediate axis. For example, in some embodiments, the markers 720 can be mounted on the x-axis 66. Thus, when the x-axis 66 moves, so do the optical markers 720. In this location, there is less chance that the surgeon will block them from the cameras 8200 or that they would become an obstruction to surgery. Because of the high accuracy in calculating the orientation and position of the end-effectuator 30 based on the encoder outputs from each axis, it is possible to very accurately determine the position of the end-effectuator 30 knowing only the position of the markers on the x-axis 66.

Some embodiments include an algorithm for automatically detecting the centers of the radio-opaque markers 730 on the medical image. This algorithm scans the medical image in its entirety looking for regions bounded on all sides by a border of sufficient gradient. If further markers 730 are found, they are checked against the stored locations and thrown out if outside tolerance.

Figure 44:
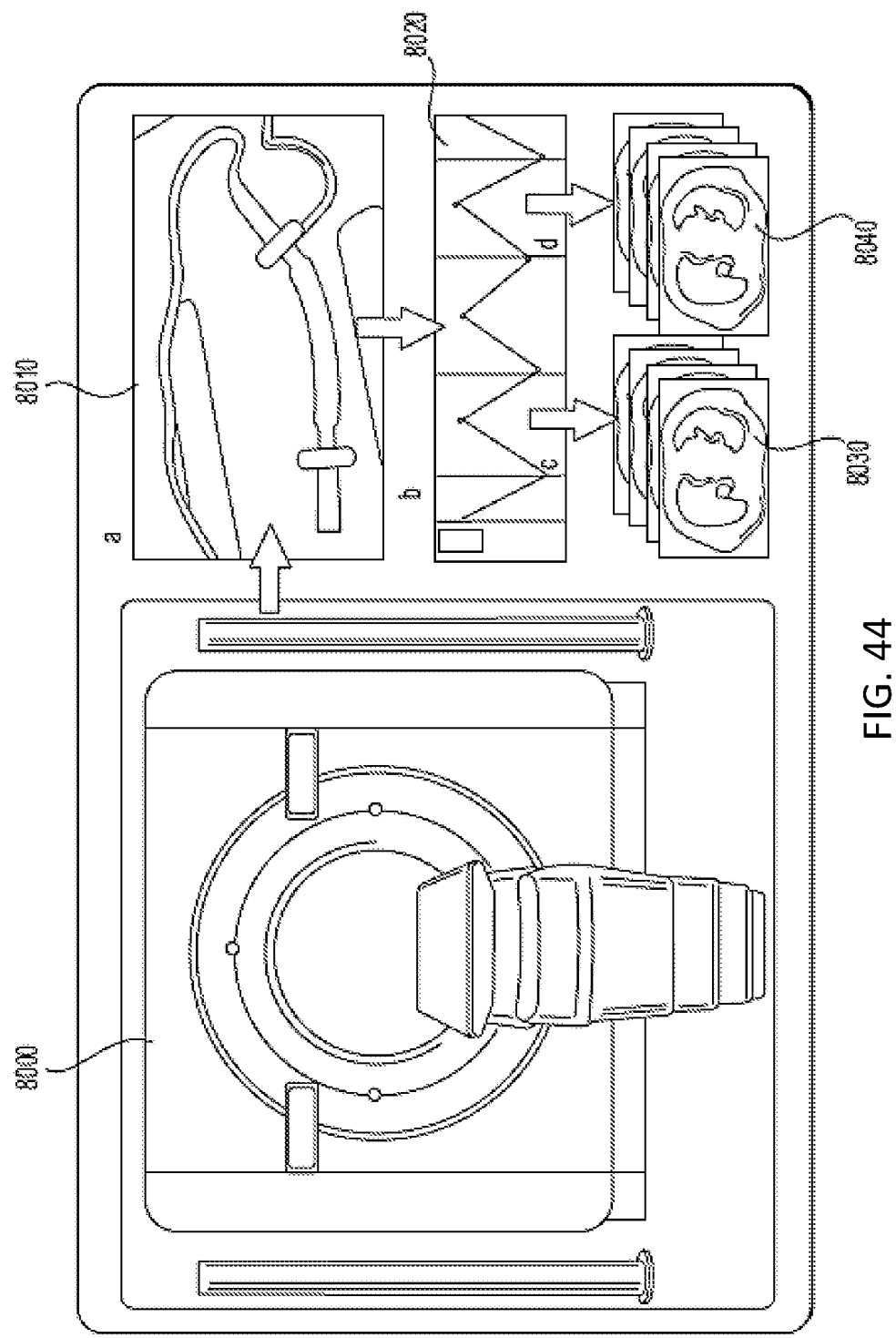
FIG. 44 illustrates a CT scan and methods in accordance with one embodiment of the invention.

Some biopsy procedures can be affected by the breathing process of a patient, for example when performing a lung biopsy. In some procedures, it is difficult for the clinician to obtain a sample during the correct breathing phase. The use of tracking markers 720 coupled to a bone of the patient cannot alone compensate for the breathing induced movement of the target biopsy region. Some embodiments include a method of performing a lung biopsy with breathing correction using the system 1. Currently, for radiation treatment of lung tumors, breathing is monitored during CT scan acquisition using a "bellows" belt (see for example CT scanner 8000 in FIG. 44, with bellows image 8010. The bellows monitors the phase of breathing, and when the clinician tells the patient to hold their breath, CT scan of the patient 18 is performed. The bellows output 8010 shows the phase in which the CT was taken. Later, targeted radiation bursts can be applied when the lung is in the right position as monitored by the bellows during the treatment phase. A CT scan is taken while the bellows monitors the breathing phase and when the patient held their breath during the CT scan. Later, radiation bursts are applied instantaneously when that same phase is reached without requiring the patient 18 to hold their breath again.

Figure 45:
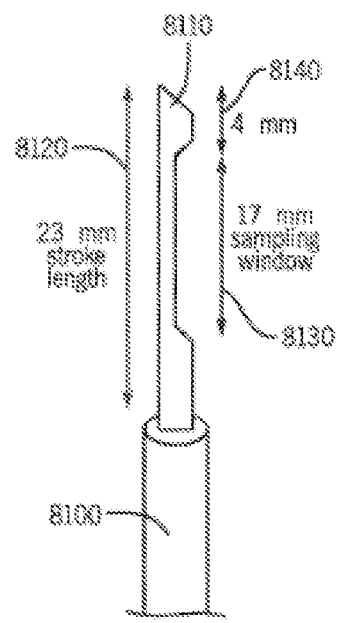
FIG. 45 illustrates a biopsy tool in accordance with one embodiment of the invention.

Some embodiments include a method of performing a lung biopsy with breathing correction using the system 1. In some embodiments, a tracking fixture 690 is attached to the patient 18 near biopsy site and bellows belt on the patient's 18 waist. In some embodiments, a CT scan of the patient 18 is performed with the patient holding their breath, and while monitoring the breathing phase. In some embodiments, a clinician locates the target (for example, a tumor) on the CT volume, and configures the robot 15 to the target using at least one of the embodiments as described earlier. In some embodiments, the robot 15 calibrates according to at least one embodiment described earlier. In some embodiments, the robot 15 moves into position above the biopsy site based the location of at least one tracking marker 720, 730. In some embodiments, the bellows belt remains in place, whereas in other embodiments, the markers 720, 730 on the patient 18 can track the breathing phase. In some embodiments, based on the bellows or tracking markers 720, 730, the computer 100 of the computing device within platform can use robotic guidance software to send a trigger during the calibrated breathing phase to deploy a biopsy gun to rapidly extract a biopsy of the target (such as a tumor). In some embodiments, a conventional biopsy gun (or tool, such as biopsy gun tip 8100 in FIG. 45) could be mounted in the robot's end-effectuator 30 and activated by a conventional mechanism (such as for example, by a toggled digital output port). For example, as shown, the biopsy gun tip 8100 can comprise a biopsy needle 8110 including a stroke length 8120, a sampling window 8130 and a biopsy tip 8140. In some embodiments, the biopsy needle 8110 in the biopsy gun tip 8100 can be mounted to the end-effectuator 30. In some embodiments, the biopsy needle 8110 can be inserted (under guidance by the robot 15) at least partially into the superficial tissues near the target (for example, the moving lung tumor). In some embodiments, the biopsy gun tip 8100 can fire as directed by a software trigger, requiring only a small penetration to retrieve the biopsy.

Deep brain stimulation ("DBS") requires electrodes to be placed precisely at targets in the brain. Current technology allows CT and MRI scans to be merged for visualizing the brain anatomy relative to the bony anatomy (skull). It is therefore possible to plan trajectories for electrodes using a 3D combined CT/MRI volume, or from CT or MRI alone. Some embodiments include robot 15 electrode placement for asleep deep brain stimulation using the system 1 where the acquired volume can then be used to calibrate the robot 15 and move the robot 15 into position to hold a guide 50 for electrode implantation.

In some embodiments, a Mayfield frame 6700 modified including one possible configuration for active and radio-opaque markers (shown in FIG. 34 in accordance with one embodiment of the invention) can be used for electrode placement for asleep deep brain stimulation. In some embodiments, the active markers 720 do not need to be attached at the time of the scan as long as their eventual position is unambiguously fixed. In some embodiments, the radio-opaque markers 730 can be removed after the scan as long as the relative position of the active markers 720 remains unchanged from the time of the scan. In some embodiments, the marker 730 can be a ceramic or metallic sphere, and for MRI, a suitable marker is a spherical vitamin E capsule. In some embodiments, the end-effectuator 30 can include an interface for feeding in a conventional electrode cannula and securing the electrode housing to the skull of the patient 18 (for example, using a Medtronic StimLoc® lead anchoring device to the skull). StimLoc® is a trademark of Medtronic, Inc., and its affiliated companies.

Figure 46:
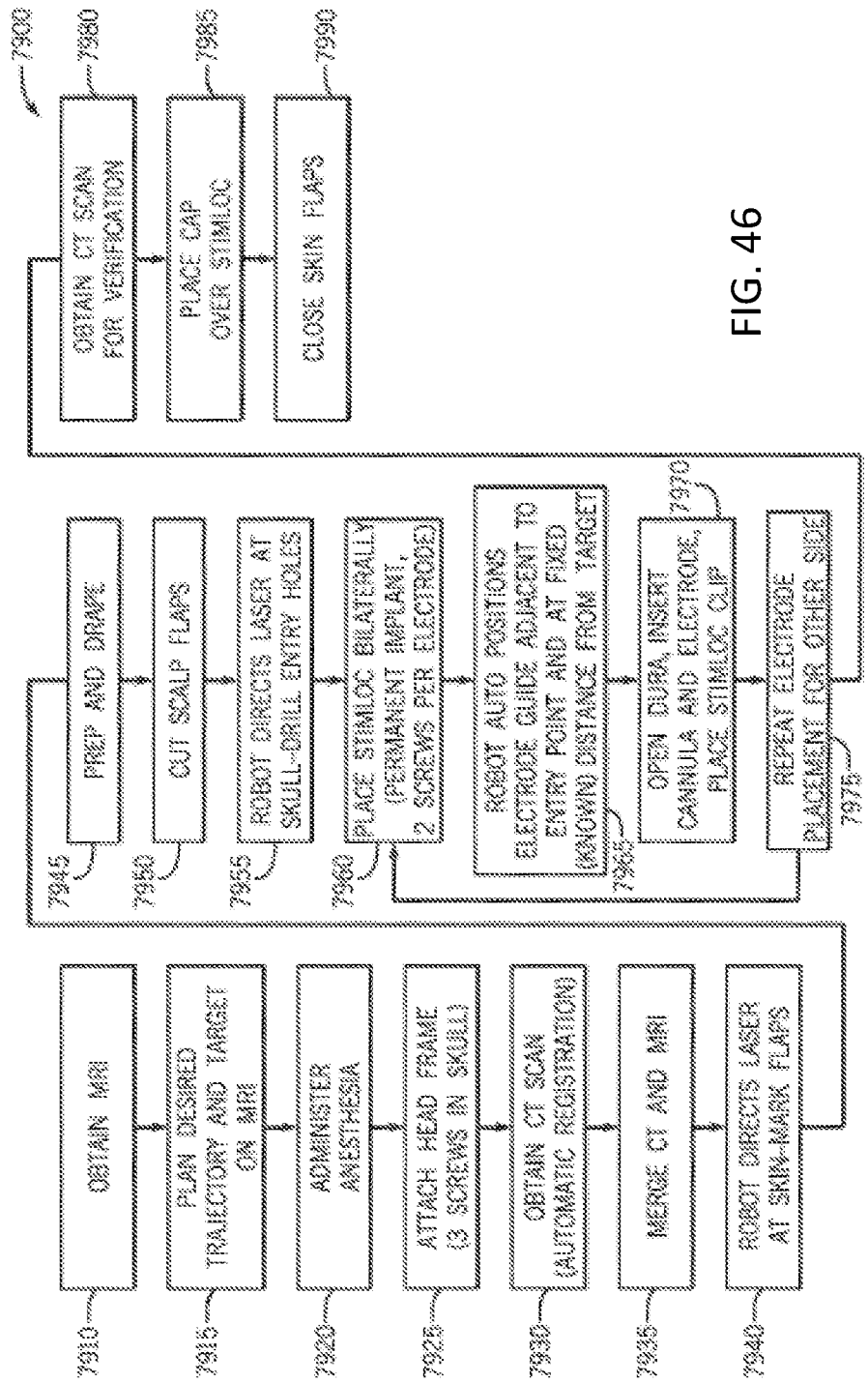
FIG. 46 illustrates a deep brain stimulation electrode placement method performed by the robot system in accordance with one embodiment of the invention.
Figure 47:
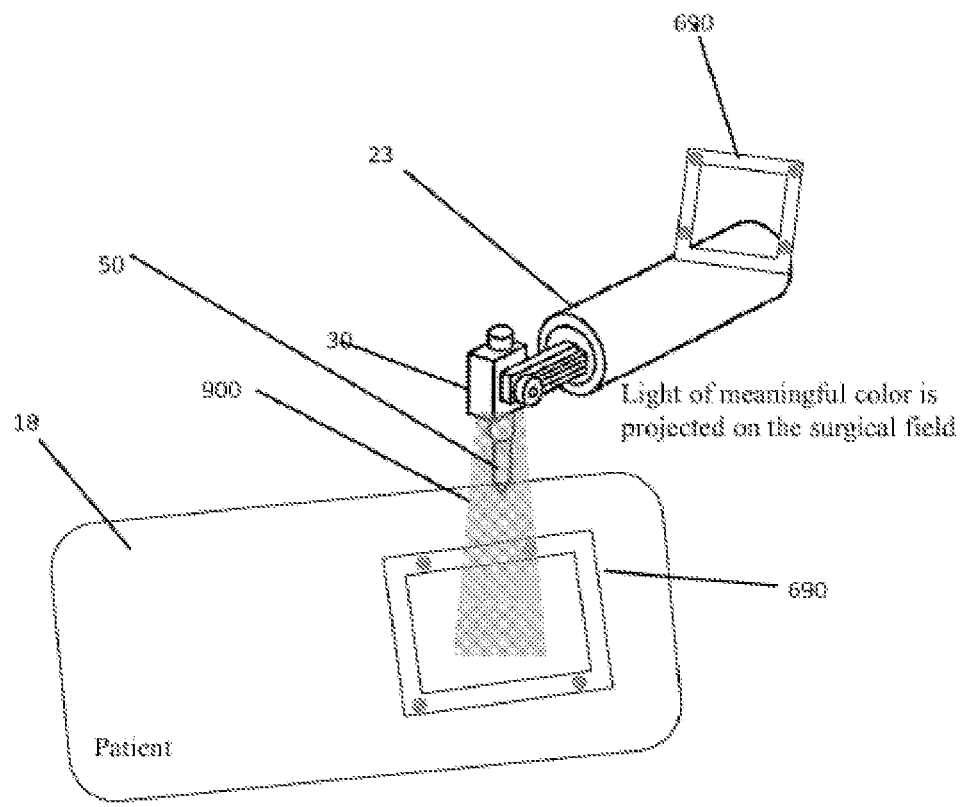
FIG. 47 illustrates a partial view of a surgical robot system including a visual indicator comprising lights projected on the surgical field in accordance with one embodiment of the invention.

In some embodiments, the system 1 can perform the method steps 7910-7990 as outlined in FIG. 46 for DBS electrode placement. As show, in some embodiments, the patient 18 can receive an MRI 7910, and the target and trajectory can be planned 7915. Surgery can be initiated under general anesthesia 7920, and the head frame (as shown in FIG. 34) can be attached to the patient 18 with three screws in the skull 7925. In some embodiments, a CT scan can be performed 7930, and the previously obtained MRI 7910 can be merged with the CT scan 7935. During the CT scan, software can automatically register the anatomy relative to the markers 720, 730 that are mounted on the head holder. In some embodiments, the robot 15 can direct a laser at the skin of the patient 18 to mark flaps 7940. In some embodiments, the skin of the patient 18 can be prepared and draped 7945, and scalp flaps can be prepared 7950. As shown, in some embodiments, the robot 15 can laser drill entry holes 7955, and the StimLoc can be secured bilaterally 7960 (permanent implant, 2 screws per electrode). In some embodiments, the robot 15 can auto-position a conventional electrode guide adjacent to entry point at a fixed (known) distance from target 7965. In some embodiments, the dura can be opened, a cannula and electrode inserted, and a StimLoc clip can be positioned 7970. In some embodiments, steps 7965, 7970 are repeated for the other side of the patient's skull 7975. In some embodiments, a verification CT scan is performed 7980, a cap is placed over the StimLoc, and the flaps are closed.

In some embodiments, the robot system 1 includes at least one mounted camera. For example, FIG. 48 illustrates a perspective view of a robot system including a camera arm in accordance with one embodiment of the invention. In some embodiments, to overcome issues with line of sight, it is possible to mount cameras for tracking the patient 18 and robot 15 on an arm 8210 extending from the robot. As shown in FIG. 48, in some embodiments, the arm 8210 is coupled to a camera arm 8200 via a joint 8210a, and the arm 8210 is coupled to the system 1 via joint 8210b. In some embodiments, the camera arm 8200 can be positioned above a patient (for example, above a patient 18 lying on a bed or stretcher as shown in FIG. 48). In this position, in some embodiments, it might be less likely for the surgeon to block the camera when the system 1 is in use (for example, during a surgery and/or patient examination). Further, in some embodiments, the joints 8210a, 8210b can be used to sense the current position of the cameras (i.e. the position of the camera arm 8200). Moreover, in some embodiments, the exact position of the end-effectuator 30 in the camera's coordinate system can be calculated based on monitored counts on each robot axis 66, 68, 70, 64, and in some embodiments, the cameras 8200 would therefore only have to track markers 720 on the patient 18.

Figure 49A:
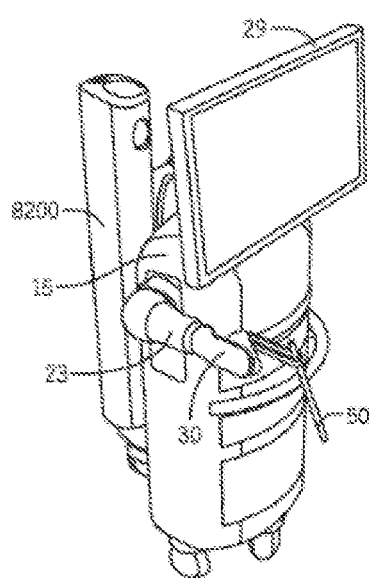
FIGS. 49A-49B illustrate front-side and rear-side perspective views, respectively, of a robot system including a camera arm in a stored position in accordance with one embodiment of the invention.
Figure 49B:
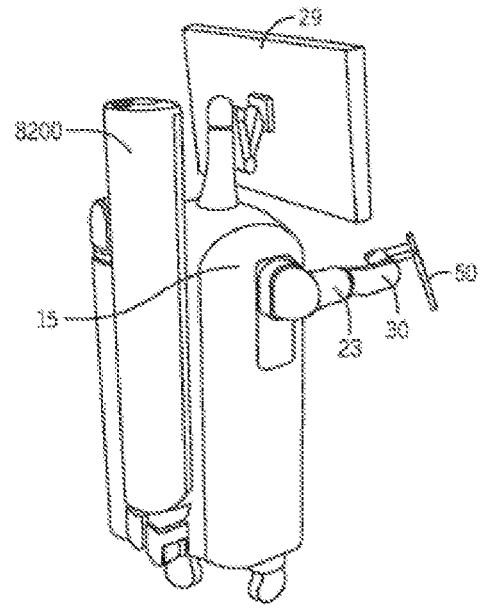

Some embodiments include an arm 8210 and camera arm 8200 that can fold into a compact configuration for transportation of the robot system 1. For example, FIG. 49A illustrates a front-side perspective view of a robot system including a camera arm in a stored position, and FIG. 49B illustrates a rear-side perspective view of a robot system including a camera arm in a stored position in accordance with one embodiment of the invention.

Some embodiments can include methods for prostate 8330 immobilization with tracking for imaged-guided therapy. In some embodiments, to enable the insertion of a needle (7405, 7410, 7600, 8110 for example) into the prostate 8330 utilizing 3D image guidance, a 3D scan of the prostate 8330 relative to reference markers 720, 730 or other tracking system is needed. However, the prostate 8330 is relatively mobile and can shift with movement of the patient 18. In some embodiments, it may be possible to immobilize the prostate 8330 while also positioning and securing tracking markers 720 in close proximity to improve tracking and image guidance in the prostate 8330.

Figure 50:
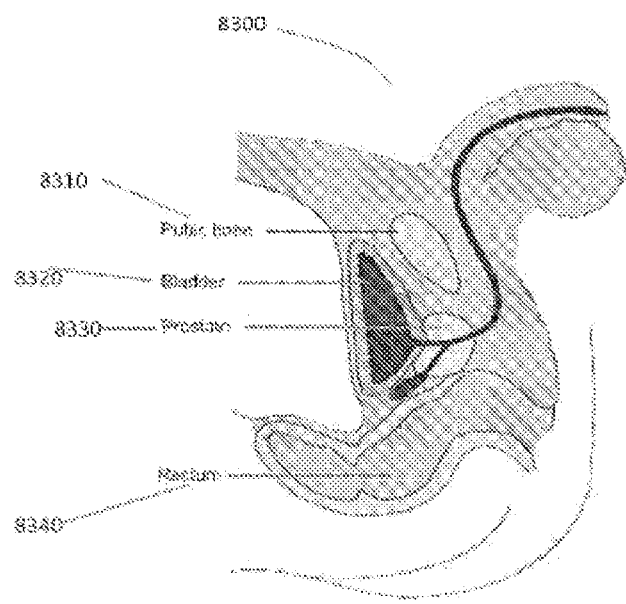
FIG. 50 shows a lateral illustration of a patient lying supine, showing the normal relative positions of the prostate, rectum, bladder, and pubic bone.
Figures 51A, 51B:
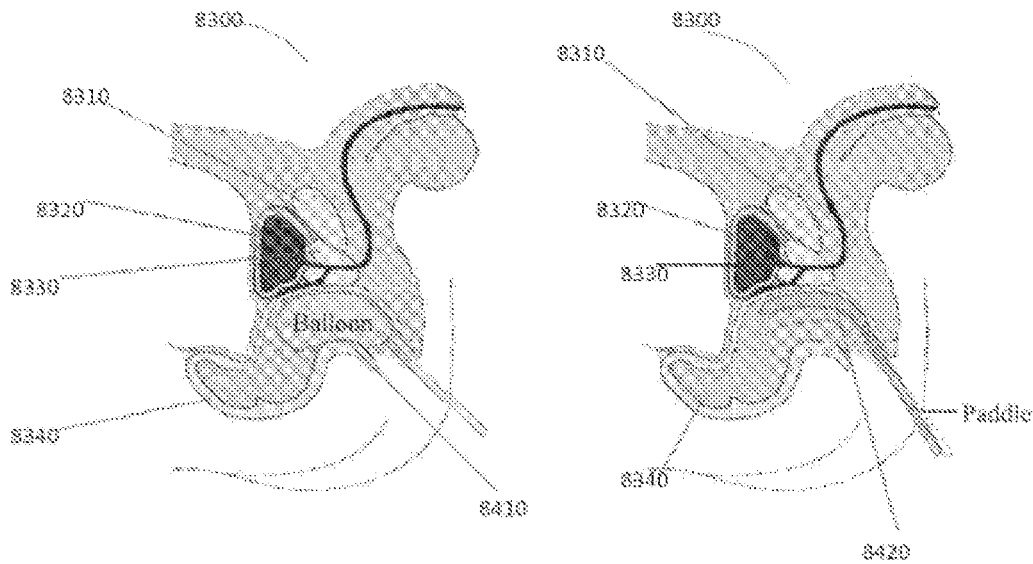
FIGS. 51A-51B show lateral illustrations of a patient lying supine, showing how inflation of a balloon and shifting of a paddle in the rectum, respectively, can cause anterior displacement of the prostate toward the pubic bone, and a controllable amount of compression against the pubic bone in accordance with one embodiment of the invention.

The prostate 8330 is anatomically positioned adjacent to the bladder 8320, the pubic bone 8310, and the rectum 8340 (see for example FIG. 50 showing a lateral illustration of a patient lying supine, depicting the normal relative positions of the prostate 8330, rectum 8340, bladder 8320, and pubic bone 8310). This position facilitates entrapment of the prostate 8330, especially when it is enlarged, against the bladder 8320 and pubic bone 8310 via anterior displacement applied within the rectum 8340. In some embodiments, displacement could be applied using a balloon 8410, a paddle 8420, or a combination of the two elements. For example, FIG. 51A shows a lateral illustration of a patient lying supine, showing how inflation of a balloon can cause anterior displacement of the prostate 8330 toward the pubic bone 8310, and a controllable amount of compression against the pubic bone 8310 in accordance with one embodiment of the invention. Further, FIG. 51B shows a lateral illustration of a patient lying supine, showing how shifting of a paddle in the rectum 8340 can cause anterior displacement of the prostate 8330 toward the pubic bone 8310, and a controllable amount of compression against the pubic bone 8310 in accordance with one embodiment of the invention.

In some embodiments, the balloon 8410 has the advantage that it can be inserted into the rectum 8340 un-inflated, and then when inflated. In some embodiments, it will displace the wall of the rectum 8340 and prostate 8330 laterally toward the pubic bone 8310. In some embodiments, a paddle 8420 can cause lateral displacement of the rectal wall and prostate 8330 if a pivot point near the anus is used.

Figure 52:
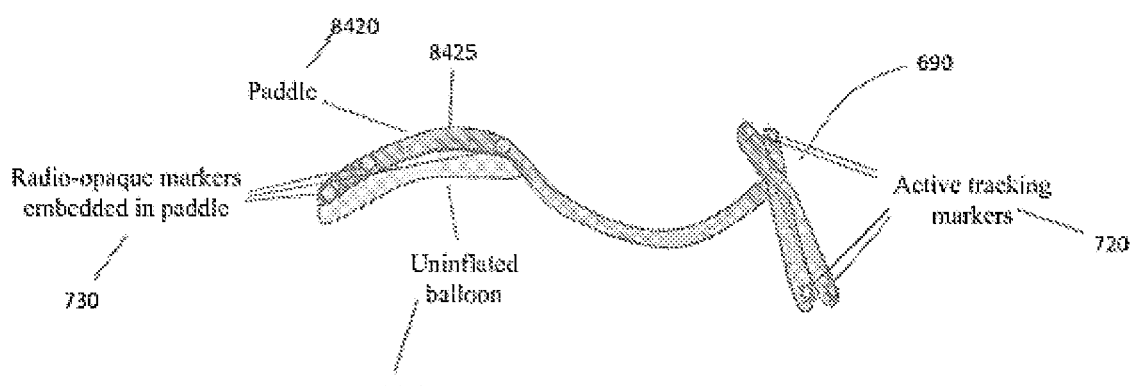
FIG. 52 shows a sketch of a targeting fixture and immobilization device to be used for tracking the prostate during image-guided surgical procedures in accordance with one embodiment of the invention.
Figure 53:
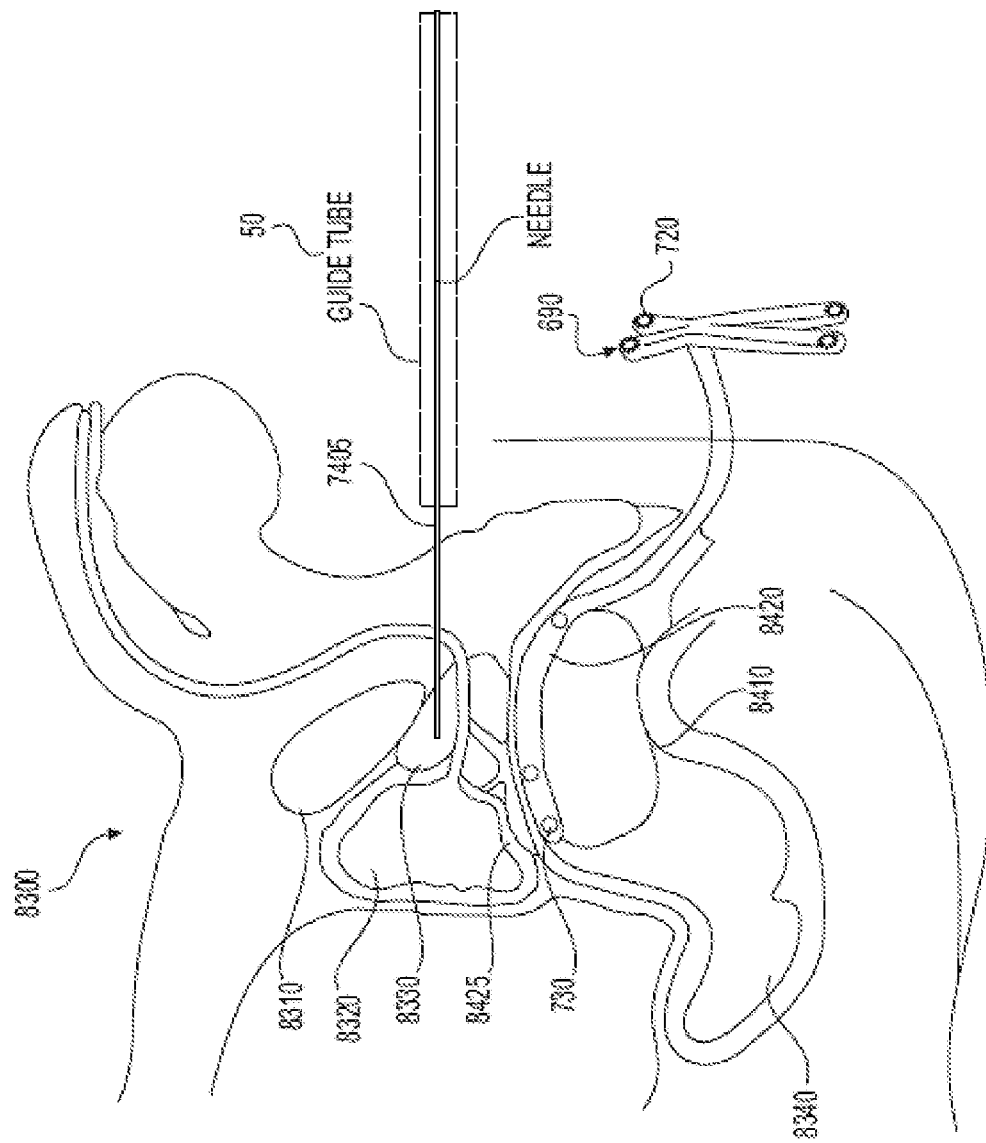
FIG. 53 shows an illustration of the device as illustrated in FIG. 52, in place in the rectum with prostate compressed and immobilized and tracking markers visible protruding caudal to the rectum in accordance with one embodiment of the invention.

In some embodiments, it is possible to configure a device consisting of a balloon 8410 and paddle 8420 such that fiducials are embedded in the device, with these fiducials being detectable on the 3D medical image (for instance, such as MRI). For example, FIG. 52 shows a sketch of a targeting fixture and immobilization device to be used for tracking the prostate 8330 during image-guided surgical procedures in accordance with one embodiment of the invention. As shown, active tracking markers 720 can be rigidly interconnected to the paddle element 8420 such that these tracking markers 720 protrude from the rectum 8340 and are visible to tracking cameras (for example, 8200) during the medical procedure. For example, FIG. 53 shows an illustration of the device as illustrated in FIG. 52, in place in the rectum 8340 with prostate 8330 compressed and immobilized and tracking markers visible protruding caudal to the rectum 8340 in accordance with one embodiment of the invention.

In some embodiments, in addition to applying lateral force from the side of the rectum 8340, it is also possible to apply lateral force from the side of the abdomen of the patient 18. In some embodiments, this secondary lateral force, used in conjunction with the force from the rectal wall, may assist in keeping the prostate 8330 immobilized. Additionally, it can serve as a support to which the tracking markers 720 are attached, and can serve as a support to which the rectal paddle/balloon 8420, 8410 can be attached for better stabilization. In some embodiments, the abdominal support can consist of a piece that presses from anterior toward posterior/inferior to press against the top of the bladder 8320 region. For example, conventional straps or pieces that encircle the legs can provide additional support. Since the abdominal shape and leg shape varies among patients, some customization would be beneficial. In some embodiments, adjustable straps and supports made of thermoplastic material could be utilized for customization. In some embodiments, commercially available thermoplastic supports (for example, from Aquaplast Inc) can be used. In some embodiments, the supports are formed by first dipping the support material in hot water to soften it, then applying the support to the patient's skin and molding it. After removing the support material from the hot water, the temperature is low enough that it does not burn the skin, but is warm enough that the support material remains soft for 1-5 minutes. In some embodiments, when the support cools, it maintains the skin contours against which it has been formed. In some embodiments, this type of support could be made for immobilizing the prostate 8330 shaped like moldable briefs. In this instance, the support would be dipped in hot water and then external straps and/or manual pressure would be applied to force the support device to press down toward the prostate 8330. Further, in some embodiments, the support could be manufactured in two halves, formed so that it is molded while two halves are tied together, and then removed (untied) when cool (so that it can later be reattached in the same configuration during the procedure).

In some embodiments, the combination of the elements as described above (including balloon 8410 and/or paddle 8420, enables real-time tracking of the prostate 8330, and manual or robotically assisted insertion of needles (for example, 7405, 7410, 7600, 8110) into the prostate 8330 based on targeting under image guidance. In some embodiments, the procedure can include the conventional abdominal support device as described above. The device would be prepared by dipping in hot water until soft, then applying to the patient such that gentle pressure is maintained from anterior to posterior/inferior against the bladder 8320 region and prostate 8330. In some embodiments, under palpation, the tracking device (paddle 8420 with coupled fixture 690 including markers 720 illustrated in FIG. 52) would be inserted into the rectum 8340 with the paddle 8420 and radio-opaque markers 730 adjacent to the prostate 8330. In this instance, gentle pressure can be manually applied to the protruding handle by the surgeon to maintain the position of the interior paddle 8420. In some embodiments, the balloon 8410 is inflated to maintain gentle compression against the prostate 8330, and to immobilize the prostate 8330 against the pubic bone 8310. In some embodiments, if the conventional abdominal device is used, the abdominal device is interconnected to the rectal device at this point for additional stability. In some embodiments, an MRI is obtained. During the MRI, the active tracking markers 720 are not attached since they are metallic. In some embodiments, sockets or other conventional quick-connect mechanical device are present in the locations where the markers 720 or marker tree (fixture 690) will later be inserted. In some embodiments, the MRI captures an image of the prostate 8330, and the radio-opaque markers 730 embedded in the handle 8425. In some embodiments, the MRI can be captured with the patient's legs down to allow the patient 18 to fit into the gantry of the scanner. In some embodiments, the patient 18 is positioned on the procedure table with legs raised. Tracking markers 730 are snapped into the sockets on the protruding handle or the marker tree 690 with markers 720 is otherwise fastened. In some embodiments, registration of the markers 730, 720 is achieved by software (for example, using one or more modules of the software using the computing device), which automatically detects the positions of the radio-opaque markers 730 on the medical image. In some embodiments, the known relative positions of the active tracking markers 720 and the radio-opaque marker 730 fiducials synchronizes the coordinate systems of the anatomy of the patient 18, tracking system and software, and robot 15. In some embodiments, the surgeon plans trajectories for needle 7405 insertion into the prostate 8330 on the medical image, and the robot 15 moves the guide tube 50 to the desired 3D location for a needle 7405 of known length to be inserted to the desired depth.

Figure 54:
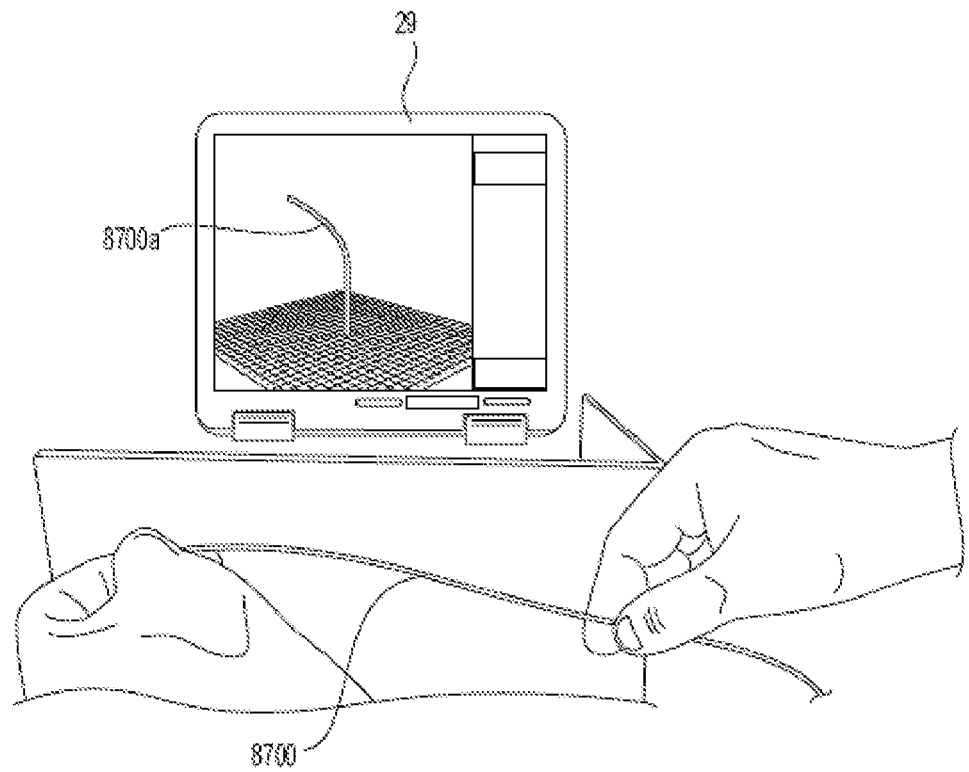
FIG. 54 illustrates a demonstration of a fibre Bragg grating ("FBG") interrogation technology with a flexible fiber optic cable in accordance with one embodiment of the invention.
Figure 55:
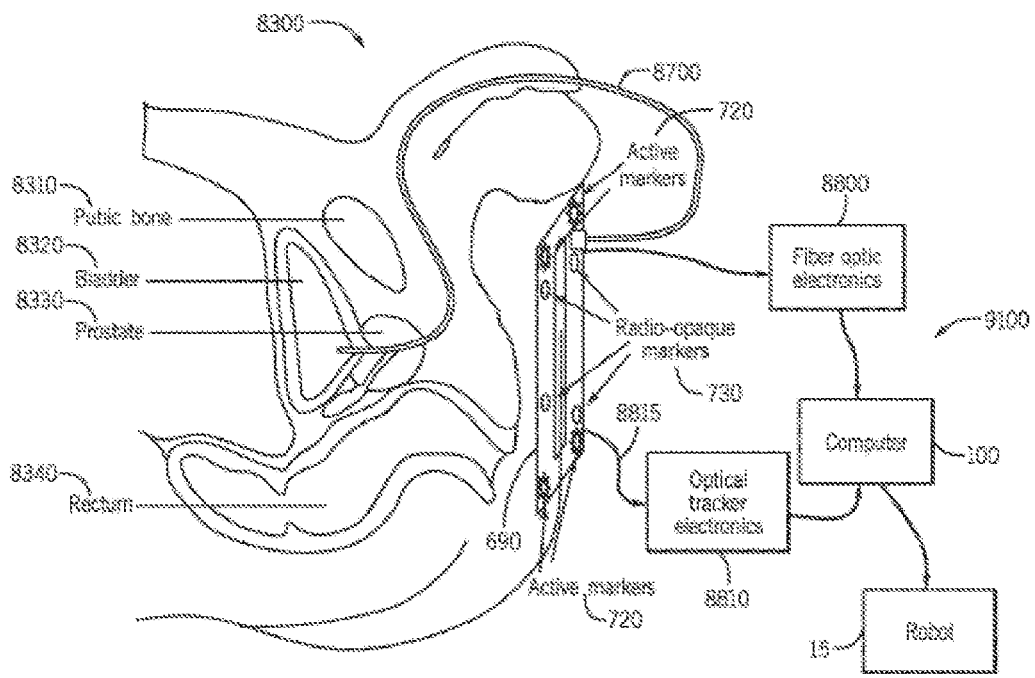
FIG. 55 illustrates a tracker attached to the surface of the skin of a patient and rigidly interconnected to a fiber optic probe to allow accurate tracking of the prostate in accordance with one embodiment of the invention.

Some embodiments can use a dual mode prostate 8330 tracking for image-guided therapy. For example, in some embodiments, it is possible to accurately track the prostate 8330 using a combination of two tracking modalities, including fiber optic tracking. For this alternate method to be used, an optical tracker (fiber optic probe 8700) would first be applied externally. This probe 8700 would be registered to the 3D medical image (for example, using an MRI scan) in substantially the same way as previously described, such as for the spine tracking using CT imaging. In some embodiments, after registering and calibrating so that the coordinate systems of the medical image and cameras 8200 are synchronized, a means of updating and correcting for movement of the prostate 8330 can be used. In some embodiments, the probe 8700 can comprise a fiber optic sensor with a Bragg grating. For example, FIG. 54. illustrates a demonstration of a fibre Bragg grating ("FBG") interrogation technology with a flexible fiber optic cable in accordance with one embodiment of the invention. As shown the technology is available from Technobis Fibre Technologies, Uitgeest, Holland. As the fiber optic cable is bent by hand, the system accurately senses the position to which the cable deforms. As depicted in FIG. 55, in some embodiments, the probe 8700 could be inserted into the urethra with the tip of the sensor positioned at the prostate 8330. Since the prostate 8330 surrounds the urethra, a sensor such as probe 8700 positioned in the urethra should show very accurately how the prostate 8330 moves. As shown, the probe 8700 can be coupled with the fixture 690 including markers 720, 730, and coupled to the computer 100 with optical tracker electronics 8810 and fiber optic electronics 800 coupled to the computer 100, coupled to the robot 15.

Figure 56:
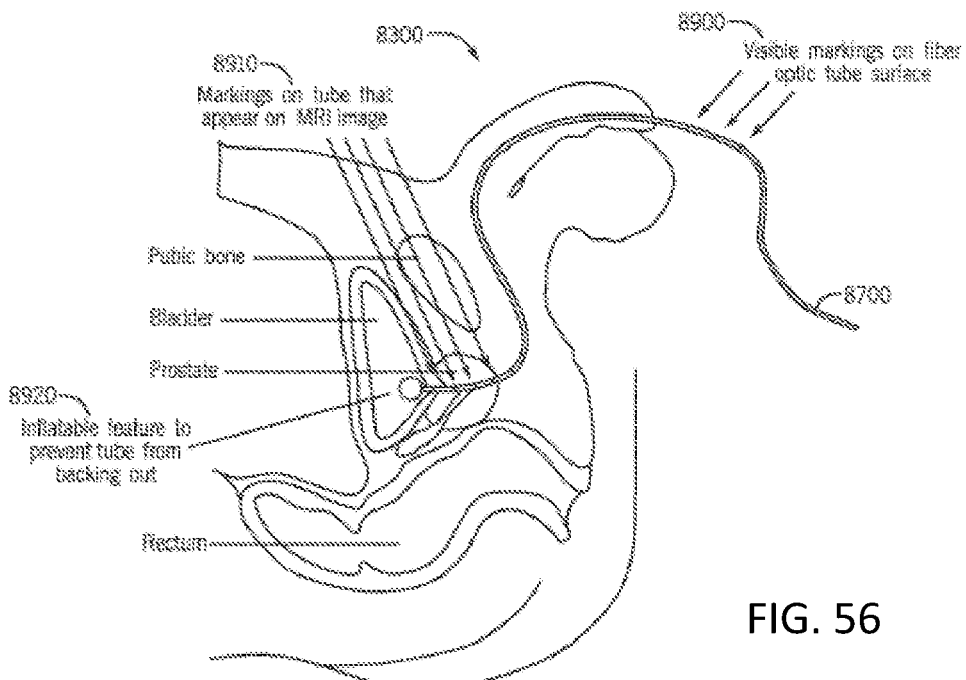
FIG. 56 illustrates the fiber optic probe as depicted in FIG. 55 with optically visible and MRI visible markings in accordance with one embodiment of the invention.

In some embodiments, markings 8910 (gradations) capable of being visualized on MRI can be placed on the outer shaft of the probe 8700 (see for example, FIG. 56). In some embodiments, if the MRI is obtained while the probe 8700 is in position in the urethra, it is possible to determine which point or points along the length of the probe 8700 represent key landmarks within the prostate 8330 (e.g., distal entry, proximal exit, midpoint). In some embodiments, these points can then be tracked by the fiber optic electronics 8800 during the procedure. In some embodiments, the points can then be used to adjust the coordinate system of the prostate 8330 so that the local coordinate system remains properly synchronized with the coordinate system of the optical tracking system even if the surrounding anatomy (specifically the anatomy to which the tracking markers 720, 730 are attached) shifts relative to the prostate 8330. In other words, the position of the tracking markers 720, 740 on the patient's skin surface gives an approximate estimate of where the prostate 8330 is currently located, and the fiber optic probe 8700 (which is rigidly interconnected to the tracking fixture 690) corrects this position to substantially improve accuracy and account for shifting of the prostate 8330.

Figure 57:
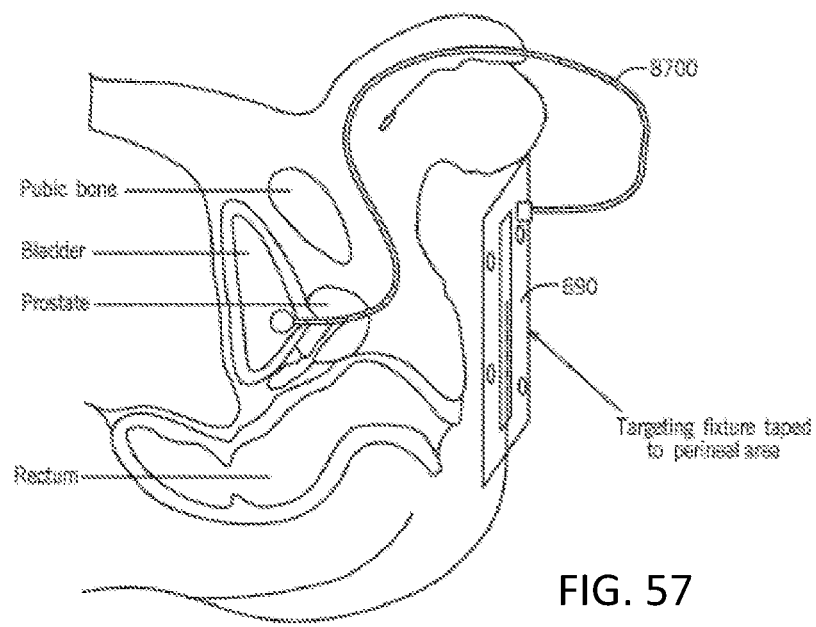
FIGS. 57-60 illustrate various embodiments of a fiber optic probe tracking system to allow accurate tracking of the prostate for image-guided therapy in accordance with one embodiment of the invention.

In some embodiments, image-guided therapy can be performed using one or more of the embodiments as described. For example, in some embodiments, the fiber optic probe as depicted in FIG. 55 can include optically visible 8900 and MRI visible 8910. In some embodiments, the probe 8700 is inserted into the penis and advanced until the tip passes into the bladder 8320 (shown in FIG. 56). In some embodiments, the marking 8900, 8910 will provide information about what section of the fiber optic is positioned within the prostate 8330. In some embodiments, the depth of insertion is recorded based on visible markings 8900 on the proximal end that has not entered the penis is recorded. In some embodiments, this information can be used to check whether the probe 8700 has moved, or to reposition the probe 8700 if it is intentionally moved. In some embodiments, the proximal end may be secured (taped) to the penis to prevent advancement or withdrawal with patient 18 movement. In some embodiments, the distal end may have a feature to prevent it from easily sliding back out of the bladder 8320. For example, as shown in FIG. 57, some embodiments include a probe 8700 that comprises an inflatable tip 8920. In some embodiments, the inflatable tip 8920 can be enlarged or flared in the area near the tip. In some embodiments the tip 8920 comprises a balloon that is inflatable after the tip has passed into the bladder 8320, whereas in other embodiments, the tip 8920 comprises conventional soft wings that deploy after the tip has passed into the bladder 8320. As shown in FIG. 57, in some embodiments, a targeting fixture 690 is attached to the patient 18 in the region of the perineum (or abdomen or other suitable surface). The targeting fixture has embedded radio-opaque fiducial markers 730 that will show up on the MRI (or other 3D scan), and is equipped with a conventional quick-connect interface that will later accept an attachment with active tracking markers 720. These tracking markers 720 do not need to be present yet, especially if they are not MRI compatible. The targeting fixture 690 can be rigidly interconnected with the proximal end of the fiber optic probe 8700.

Figure 58:
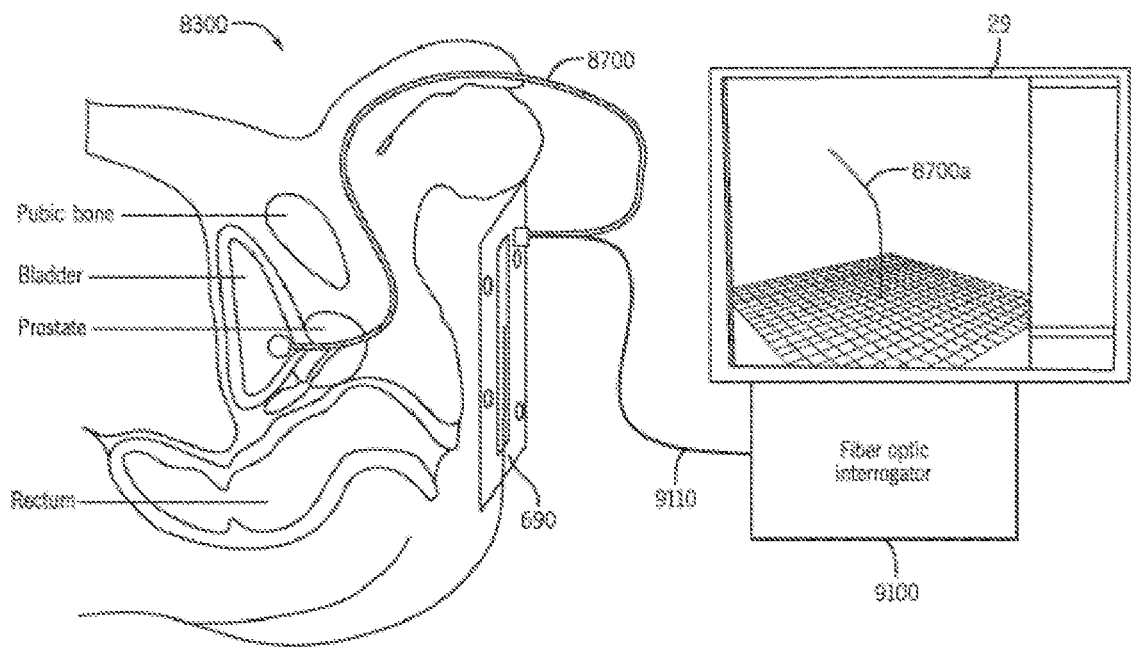

In some embodiments, the patient 18 is positioned outside or in the gantry of the MRI scanner before scanning. In some embodiments, the fiber optic tracking system 9100 is briefly activated to record position of the fiber optic probe 8700 along its entire length for later reference (see FIG. 58). Once recorded, the electronic interface (8800) for the fiber optic tracking system 9100 may be disconnected and removed from the MRI area. In some embodiments, an MRI scan is obtained. The scan must visualize the prostate 8330, the radio-opaque fiducials 730 on the targeting fixture 690, and the markings 8910 that are present along the urethral tube that will be tracked with fiber optic probe 8700. In some embodiments, the position of the prostate 8330 along the fiber optic probe 8700 at the time of the scan is recorded from the radio-opaque markings 8910 on its surface.

Figure 59:
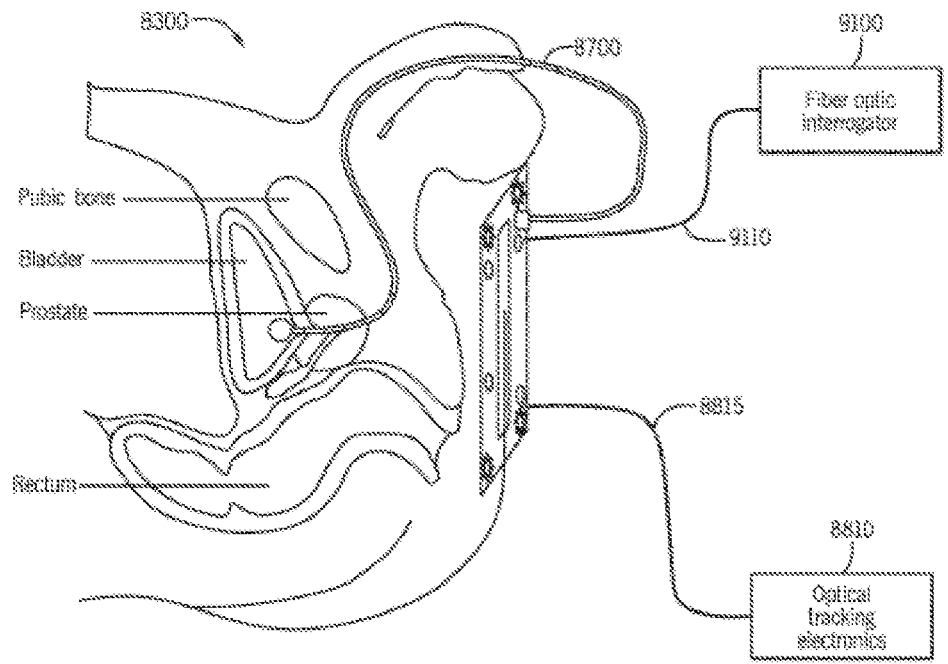

In some embodiments, the patient is positioned on the procedure table, and optical tracking markers 720 are snapped into the targeting fixture (see FIG. 59) and activated. In some embodiments, registration of the markers 720 is achieved by software (for example by one or more modules within the device), which automatically detects the positions of the radio-opaque markers 730 on the medical image. The known relative positions of the active tracking markers 720 and the radio-opaque fiducials 730 synchronizes the coordinate systems of the anatomy, tracking system, and robot 15. The fiber optic tracking system 9100 is activated.

Figure 60:
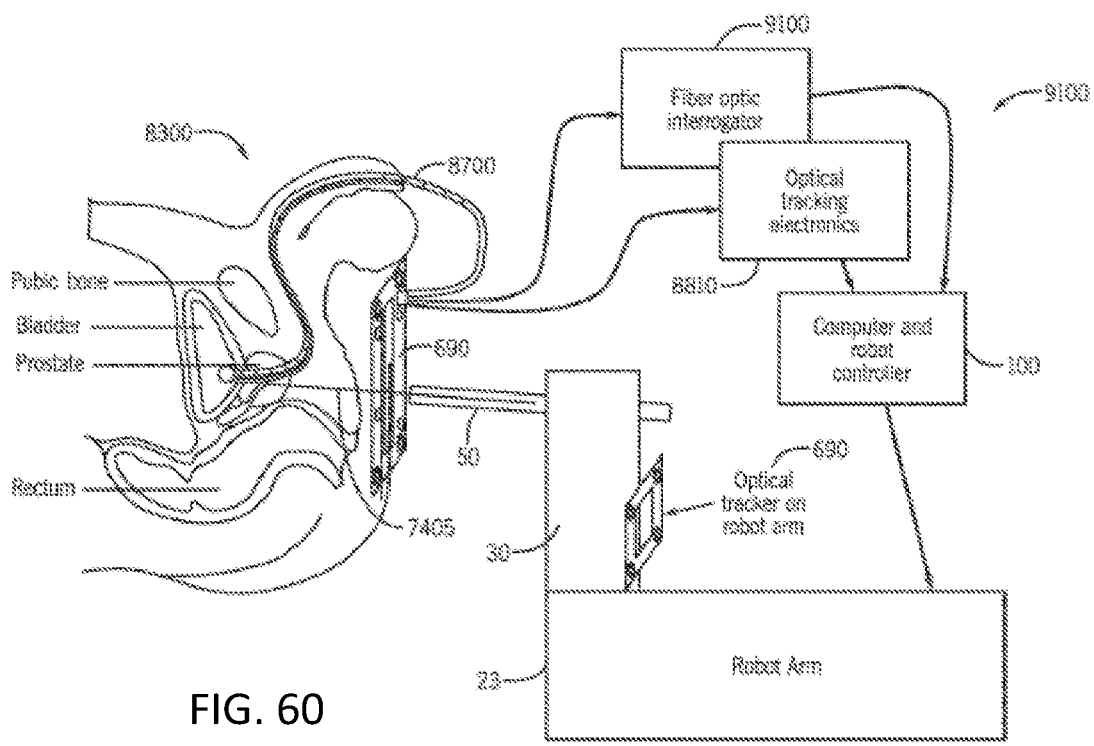

In some embodiments, the offset of the prostate 8330 from the position recorded on the MRI scan is determined as the offset of the prostate 8330 in the optically sensed position of the probe 8700 relative to the position at the time of the MRI scan. In some embodiments, the surgeon plans trajectories for insertion of the needle 7405 into the prostate 8330 (from the medical image), and the robot 15 moves the guide tube 50 to the desired 3D location for a needle 7405 to be inserted to the desired depth (see FIG. 60). In some embodiments, an offset necessary to ensure that the correct region of the prostate 8330 is targeted, is determined from the probe 8700 sensed offset, and the position of the guide tube 50.

In some other embodiments, the probe 8700 could be inserted down the esophagus to track movement of the stomach, intestines, or any portion of the digestive system. In some embodiments, it could be inserted into a blood vessel to track the position of major vessels inside the body. In some embodiments, it could be inserted through the urethra into the bladder, ureters, or kidney. In all cases, it would help localize internal points for better targeting for therapy.

In some further embodiments, the probe 8700 could be combined with a conventional catheter for other uses. For example, fluid could be injected or withdrawn through a hollow conventional catheter that is attached along its length to the probe 8700. Further, in some embodiments, a conventional balloon catheter could also be utilized. The balloon could be temporarily inflated to secure a portion of the probe 8700 within the urethra, or other position inside the body, ensuring that the probe 8700 does not move forward or backward once positioned where desired.

A number of technologies for real-time 3D visualization of deforming soft tissue and bony anatomy without the radiation are available and/or are in development. In some embodiments, the surgical robot 15 can use these technologies during surgery, or other image-guided therapy. In some embodiments, the use of real-time 3D visualization, automated non-linear path planning and automated steering and advancement of flexible catheters or wires (for example wires 7405, 7410, 8600, or 8110) in a non-linear path becomes increasingly important.

In some embodiments, it may be possible to visualize soft tissues in real time by combining MRI (magnetic resonance imaging) and ultrasound or contrast enhanced ultrasound ("CEUS"). For example, in some embodiments, an MRI scan and a baseline ultrasound scan would be obtained of the anatomy of interest. In some embodiments, landmarks visualized on the ultrasound would be correlated to the MRI (for example, borders of organs, blood vessels, bone, etc.). In some embodiments, a discrete set of key landmarks could be correlated such that the movement of other points of interest between these landmarks could be interpolated. In some embodiments, a computerized geometric model (with its unmoved baseline position corresponding to the anatomy seen on the MRI) would be created. Then, when movements of the landmark points are detected on ultrasound, the positions of the corresponding tissues visualized on the model can be adjusted. In some embodiments, the ultrasound would be allowed to run continuously, providing real-time data on the positions of the landmarks. In some embodiments, changes in landmark position would be used to update the model in real time, providing an accurate 3D representation of the soft tissues without exposure to radiation. In some embodiments, optical tracking markers 720 attached to the conventional ultrasound probes could provide data on the movement of the probes relative to the anatomy, which would affect the model calibration. In some embodiments, for accurate 3D positions of the points on the soft tissues, it may be necessary to utilize several conventional ultrasound probes locked in a rigid orientation relative to each other. In other embodiments, the ultrasound probes can be synchronized so that their relative positions are known or can be extracted. In some embodiments, optical markers 720 on multiple conventional ultrasound probes would allow registration of the multiple ultrasound probe orientations in the same coordinate system. In some further embodiments of the invention, other methods for assessing distance to tissues of interest, such as electrical conductivity, capacitance, or inductance of the tissues as mild electrical current is applied.

In the modeling approach described above for visualizing soft tissues, it should be recognized that tracking a large number of landmarks helps ensure that the model is accurate. However, there is a trade-off that tracking a large number of landmarks may slow down the process, and disallow real-time updating or require a lengthy registration process. In some embodiments, as fewer landmarks are tracked, tissue modeling to predict deformation of the non-tracked parts of the model becomes increasingly important. In some embodiments, for tissue modeling, the elasticity and other mechanical qualities of the tissues are needed. It may be possible to assess the status of the tissues through a mechanism such as spectroscopy, where absorbance of light passed through tissue might provide information on the composition of tissues, electrical conductivity, DEXA scan, MRI scan, CT scan or other means. This information could be provided to the computer model to allow better estimation of soft tissue deformation.

Another possible mechanism for visualizing soft tissues can include injecting a conventional liquid tracer into the patient 18 that causes different tissues to become temporarily detectable by an external scan. For example, the tracer could comprise a radioactive isotope that is attracted more to certain types of cells than others. Then, when the patient is placed near an array of conventional radiation sensors, the sensors could detect the concentrations of the isotope in different spatial locations.

Some embodiments include a mechanism to allow the user to control the advancement and direction of a flexible catheter or wire (for example wire 7405, 7410, 7600, or 8110) through an interface with the robot 15. In some embodiments, this mechanism can snap or lock into the robot's end-effectuator 30. In some embodiments, the guide tube 50 on the robot's end-effectuator 30 provides accurately controlled orientation and position of the catheter or wire at the point where it enters the patient. In some embodiments, the mechanism would then allow the user to control the rate and amount of advancement of the tube 50, the rate and amount of rotation of the tube 50, and activation of steering RF energy (for example, as described earlier with regard to steerable needle 7600 in FIG. 40). In some embodiments, based on assumptions about the condition of the soft tissues, and locations of obstacles such as blood vessels, nerves, or organs between entry into the patient and the target, a non-linear path is planned by the software with parameters under the user's control. For example, in some embodiments, the method can include a command sequence such as "advance 5 mm, activate steering toward an azimuth of +35°, continue advancing 5 mm while rotating at 1 per second," etc. In some embodiments, during advancement of the catheter or wire 7600 (or other wire 7405, 7410, or 8110), the real-time location of the tip is tracked using LPS or other visualization means. In some embodiments, the path plan is recalculated based on divergence from the expected path and advancement continues. In some embodiments, this advancing/turning snap-in mechanism can also be used with beveled needles, taking advantage of the direction of the bevel, and the beveled face deflection force that moves the needle laterally away from the face when advanced. In some embodiments, software would plan which direction the bevel should be oriented during different phases of needle advancement.

In some embodiments, a mechanism similar to the one described above can also be used for automatic hole preparation and insertion of screws. For example, in some embodiments, the end-effectuator 30 could have a conventional mechanism that would allow a tool to be retrieved from a conventional tool repository located somewhere outside the surgical field 17 In some embodiments, features on the tool holder would allow easy automated engagement and disengagement of the tool. In some embodiments, after retrieving the tool, the end effectuator 30 would move to the planned screw location and drill a pilot hole by rotating the assembly at an optimal drilling speed while advancing. In some embodiments, the system 1 would then guide the robot 15 to replace the drill in the repository, and retrieve a driver with appropriately sized screw. In some embodiments, the screw would then be automatically positioned and inserted. In some embodiments, during insertion of the screw, thrust and torque should be coordinated to provide good bite of the screw into bone. That is, the appropriate amount of forward thrust should be applied during rotation so the screw will not strip the hole.

Some embodiments of the method also include algorithms for automatically positioning conventional screws. For example, in some embodiments, different considerations may dictate the decision of where the screw should be placed. In some embodiments, it may be desirable to place the screw into the bone such that the screw is surrounded by the thickest, strongest bone. In some embodiments, algorithms can be used to locate the best quality bone from CT or DEXA scans, and to find an optimized trajectory such that the width of bone around the screw is thickest, or remains within cortical instead of cancellous bone for the greatest proportion. In some embodiments, it may be desirable to place the screw into the bone at an entry point that is most perpendicular to the screw, or is at a "valley" instead of a peak or slope on the bony articulations. In some embodiments, by placing the screw in this way, it is less likely to skive or rotate during insertion and therefore likely to end up in a more accurate inserted location. In some embodiments, algorithms can be used to assess the surface and find the best entry point to guide the screw to the target, while penetrating the bone perpendicular to the bone surface. In other embodiments, it may be desirable to place screws in a multi-level case such that all the screw heads line up in a straight line or along a predictable curve. In some embodiments, by aligning screw heads in this way, the amount by which the surgeon must bend the interconnecting rod is minimized, reducing the time of the procedure, and reducing weakening of the metal rod due to repeated bending. In some embodiments, algorithms can be used that keep track of anticipated head locations as they are planned, and suggest adjustments to trajectories that provide comparable bony purchase, but better rod alignment.

Some embodiments of the invention can use an LPS system that uses time-of-flight of RF signals from an emitter to an array of receivers to localize the position of the emitter. In some embodiments, it may be possible to improve the accuracy of the LPS system by combining it with other modalities. For example, in some embodiments, it may be possible use a magnetic field, ultrasound scan, laser scan, CT, MRI or other means to assess the density and position of tissues and other media in the region where the RF will travel. Since RF travels at different rates through different media (air, tissue, metal, etc.), knowledge of the spatial orientation of the media through which the RF will travel will improve the accuracy of the time-of-flight calculations.

In some embodiments, an enhancement to the robot 15 could include inserting a conventional ultrasound probe into the guide tube 50. In some embodiments, the ultrasound probe could be used as the guide tube 50 penetrates through soft tissue to help visualize what is ahead. As the guide tube 50 advances, penetrating soft tissue and approaching bone, the ultrasound probe would be able to detect contours of the bone being approached. In some embodiments, this information could be used as a visual reference to verify that the actual anatomy being approached is the same as the anatomy currently being shown on the 3D re-sliced medical image over which the robot is navigating. For example, in some embodiments, if a small protrusion of bone is being approached dead center on the probe/guide tube 50 as it is pushed forward, the region in the center of the ultrasound field representing the raised bone should show a short distance to bone, while the regions toward the perimeter should show a longer distance to bone. In some embodiments, if the position of the bony articulation on the re-sliced medical image does not appear to be lined up with the 2D ultrasound view of where the probe is approaching, this misalignment could be used to adjust the registration of the robot 15 relative to the medical image. Similarly, in some embodiments, if the distance of the probe tip to bone does not match the distance perceived on the medical image, the registration could also be adjusted. In some embodiments, where the guide tube 50 is approaching something other than bone, this method may also be useful for indicating when relative movement of internal soft tissues, organs, blood vessels, and nerves occurs.

Figure 61:
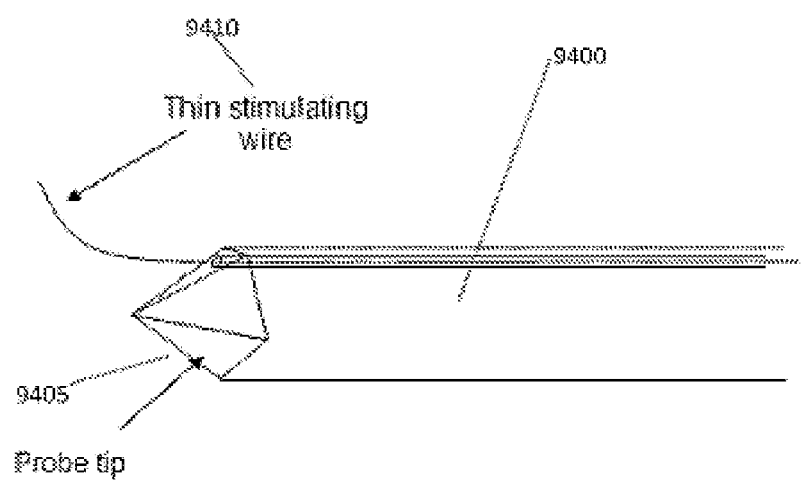
FIG. 61 illustrates one embodiment of a nerve sensing probe.

Some embodiments can include a nerve sensing probe. For example, in some embodiments, for sensing whether a penetrating probe is near a nerve, an electromyography ("EMG") response to applied current could be used, enabling the ability of the robot 15 to steer around nerves. For example, as shown in FIG. 61, a probe 9400 could be used, with 1 or more cannulation offset from the probe's 9400 central axis that would enable a thin wire 9410 to extend from the tip 9405, ahead and to one side of the tip 9405. A beveled tip 9405 (or a conical or rounded tip) could be used.

In some embodiments, the probe 9400 could be advanced manually or automatically and stopped, then the stimulating wire 9410 could be extended and current applied. In some embodiments, the EMG could be checked to verify whether a nerve is in proximity. In some embodiments, the simulating wire 9410 could be retracted, and probe 9400 rotated so that the portal for the stimulating wire 9410 is positioned at a different azimuth index. In some embodiments, the probe 9400 could again be extended to check for the presence of nerves in a different region ahead. In some embodiments, if a nerve is encountered, it would be known which direction the nerve is located, and which direction the probe 9400 would need to be steered to avoid it. In some embodiments, instead of a single wire 9410 extending and checking for a nerve, multiple wires 9410 could simultaneously be extended from several portals around the probe 9400. In some embodiments, the wires 9410 could be activated in sequence, checking for EMG signals and identifying which wire 9410 caused a response to identify the direction to avoid or steer. In some embodiments, it could be necessary to fully retract the stimulating wires 9410 before attempting to further advance the probe 9400 to avoid blocking progress of the probe 9400. In some embodiments, the stimulating wires 9410 would have a small enough diameter so as to be able to penetrate a nerve without causing nerve damage.

As noted elsewhere in this application, the robot 15 executed trajectories for paths into a patient 18 are planned using software (for example, at least one module of the software running on the computing device including computer 100) where the desired vectors are defined relative to radio opaque markers 730 on the image and therefore relative to active markers 720 on the targeting fixture 690. In some embodiments, these trajectories can be planned at any time after the image is acquired, before or after registration is performed. In some embodiments, it is possible that this trajectory planning can be done on another computerized device. For example, in some embodiments, a conventional portable device (such as a tablet computer, or a laptop computer, or a smartphone computer) could be used. In some embodiments, the 3D image volume would be transferred to the portable device, and the user would then plan and save the desired trajectories. In some embodiments, when robotic control is needed, this same image volume could be loaded on the console that controls the robot 15 and the trajectory plan could be transferred from the portable device. In some embodiments, using this algorithm, it would therefore be possible for a series of patients 18 to each to have a targeting fixture 690 applied and an imaging scan, such as a CT scan. In some embodiments, the 3D volume for each patient 18 could be exported to different portable devices, and the same or different surgeons could plan trajectories for each patient 18. In some embodiments, the same or different robot 15 could then move from room to room. In some embodiments, in each room, the robot 15 would be sterilized (or have sterile draping applied, and would receive the scan and trajectory plan. The robot 15 would then execute the plan, and then move to the next room to repeat the process. Similarly, the portion of the registration process in which the 3D image volume is searched for radio-opaque markers 730 could be performed on the portable device. Then, in some embodiments, when the robot 15 arrives, the registration information and the trajectories are both transferred to the robot 15 console. In some embodiments, by following this procedure, the time of computation of the image search algorithm on the robot 15 console is eliminated, increasing efficiency of the overall process when the robot 15 is required in multiple rooms.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

What is claimed is:

1. A surgical robot system comprising:
a robot base having a display and a computer;
a robot arm coupled to the robot base, wherein movement of the robot arm is electronically controlled by the robot base; and
a first end-effectuator, coupled to the robot arm, containing a post and a targeting fixture attached to the post;
wherein the display is configured to indicate a location of the first end-effectuator in relation to at least one of the robot base and the robot arm, and
wherein the first end-effectuator is configured to be removable from the robot arm and the robot arm is configured to receive a second end-effectuator,
wherein optical markers are mounted on an x-axis of the robot base so that the computer is configured to calculate the orientation and position of the first end effectuator based on a position of the optical markers on the robot base and the targeting fixture,
wherein the robot arm is configured to independently move the first or second end effectuator along the x, y, and z axes and configured for selective rotation about one of the x, y, and z axes, and wherein the robot arm does not provide six degrees of freedom,
wherein movements of the robot arm in the x, y, and z axes are independent of one another and adapted to move in a cartesian positioning system.

2. The surgical robot system of claim 1, further comprising one or more cameras for tracking the targeting fixture.

3. The surgical robot system of claim 2, wherein the first and second end-effectuators are configured to snap-in at an end of the robot arm.

4. The surgical robot system of claim 1, wherein the first and second end effectuators each contain identification circuitry and wherein the computer is configured to apply a stored calibration setting in response to recognizing the identification circuitry.

5. The surgical robot system of claim 4, wherein the targeting fixture comprises one or more active markers.

6. The surgical robot system of claim 1, wherein the display is configured to show positioning of the first end-effectuator in relation to a patient.

7. The surgical robot system of claim 1, further comprising a surgical instrument connected to the first end-effectuator, and wherein the display is configured to show a graphical representation of the surgical instrument relative to a patient.

* * * * *